(12) United States Patent
Beadle et al.

(10) Patent No.: US 7,619,096 B2
(45) Date of Patent: Nov. 17, 2009

(54) 3-AMINOPYRROLIDINES AS INHIBITORS OF MONOAMINE UPTAKE

(75) Inventors: Christopher David Beadle, Basingstoke (GB); Manuel Javier Cases-Thomas, Basingstoke (GB); Barry Peter Clark, Basingstoke (GB); Peter Thaddeus Gallagher, Basingstoke (GB); John Joseph Masters, Fishers, IN (US); Graham Henry Timms, Basingstoke (GB); Magnus Wilhelm Walter, Basingstoke (GB); Maria Ann Whatton, Basingstoke (GB); Virginia Ann Wood, Basingstoke (GB); Jeremy Gilmore, Basingstoke (GB)

(73) Assignee: Eli Lilly and Company, Indianapolis, IN (US)

( * ) Notice: Subject to any disclaimer, the term of this patent is extended or adjusted under 35 U.S.C. 154(b) by 424 days.

(21) Appl. No.: 10/558,626

(22) PCT Filed: May 11, 2004

(86) PCT No.: PCT/US2004/013004

§ 371 (c)(1),
(2), (4) Date: Nov. 29, 2005

(87) PCT Pub. No.: WO2005/000811

PCT Pub. Date: Jan. 6, 2005

(65) Prior Publication Data

US 2006/0270713 A1    Nov. 30, 2006

Related U.S. Application Data

(60) Provisional application No. 60/510,867, filed on Oct. 14, 2003, provisional application No. 60/524,450, filed on Nov. 24, 2003, provisional application No. 60/524,781, filed on Nov. 25, 2003.

(30) Foreign Application Priority Data

Jun. 11, 2003    (GB) ................. 0313463.2

(51) Int. Cl.
C07D 207/00    (2006.01)
A61K 31/40    (2006.01)
C07D 295/00    (2006.01)
A01N 43/36    (2006.01)

(52) U.S. Cl. ...................... 548/557; 514/343

(58) Field of Classification Search ................. 514/359; 548/557, 560, 568, 579
See application file for complete search history.

(56) References Cited

U.S. PATENT DOCUMENTS 6,353,008 B1 * 3/2002 Hertel et al. ................. 514/343
6,906,072 B1 * 6/2005 Yamamoto et al. ..... 514/252.13

FOREIGN PATENT DOCUMENTS

| EP | 1 125 922 A1 | 8/2001 |
|---|---|---|
| WO | WO 01 53258 A1 * | 7/2001 |
| WO | WO 01/66521 | 9/2001 |
| WO | WO 03/024928 A2 | 3/2003 |
| WO | WO 2004/000808 A2 | 12/2003 |
| WO | WO 2004/030668 A2 | 4/2004 |
| WO | WO 2004/052858 | 6/2004 |

OTHER PUBLICATIONS

Thomas Ryckmans, et al., "First Dual NK1 Antagonists-Serotonin Reuptake Inhibitors: synthesis and SAR of a New Class of Potential Antidepressants" Bioorganic & Medicinal Chemistry Letters, 12(2), 2002, 261-264.
Sternfeld F, et al.;"Synthesis and 1-5 Serotonergic Activity of 3-A2-(Pyrrolidin-1-YL)Ethyluin Doles: Potent Agonists for the H5-HTID Receptor with High Selectivity Over the H5-HT1B Receptor" Journal of Medicinal Chemistry, 42(4), 1999, 677-690.
International Search Report.

* cited by examiner

*Primary Examiner*—Johann R Richter
*Assistant Examiner*—Andriae M Holt
(74) *Attorney, Agent, or Firm*—Tonya L. Combs; Charles E. Cohen; Thomas E. Jackson

(57) ABSTRACT

The present invention provides compounds of formula (I)

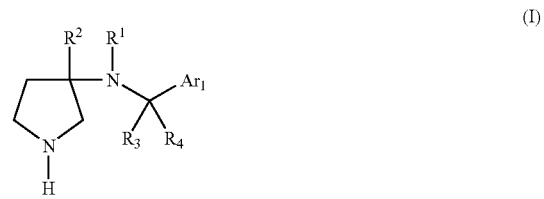

and pharmaceutically acceptable salts thereof, which are useful for the inhibition of the uptake of one or more physiologically active monoamines (serotonin, norepinephrine, and dopamine).

5 Claims, No Drawings

3-AMINOPYRROLIDINES AS INHIBITORS OF MONOAMINE UPTAKE

This application is a national stage application for PCT/US04/13004 filed under 35 U.S.C. 371, filed May 11, 2004.

This is the national phase application, under 35 USC 371, for PCT/US2004/013004, filed May 11, 2004, which claims the benefit GB application 0313463.2, filed Jun. 11, 2003, U.S. provisional application 60/510,867, filed Oct. 14, 2003, U.S. provisional application 60/524,450, filed Nov. 24, 2003, and U.S. provisional application 60/524,781, filed Nov. 25, 2003.

The present invention is directed to compounds which inhibit the uptake of one or more physiologically active monoamines selected from serotonin (also called 5-hydroxytryptamine or 5-HT), norepinephrine (also called noradrenaline) and dopamine. There is a large body of scientific evidence pointing to the physiological role of these monoamines as neurotransmitters. Consequently, compounds which are capable of inhibiting the uptake of one or more of these monoamines find utility in the treatment of disorders of the central and/or peripheral nervous system.

It is known that the 3-aryloxy-3-substituted-1-aminopropane class of compounds have demonstrated particular diversity in their ability to inhibit the uptake of monoamines. Fluoxetine (N-methyl 3-((4-trifluoromethylphenyl)oxy)-3-phenyl-1-aminopropane hydrochloride), for example, is a selective serotonin uptake inhibitor that has found great market acceptance in the treatment of depression and has also been approved for the treatment of a number of other disorders. Atomoxetine ((−)-N-methyl 3-((2-methylphenyl)oxy)-3-phenyl-1-aminopropane hydrochloride), is a selective norepinephrine uptake inhibitor that is approved for the treatment of attention deficit/hyperactivity disorder. Duloxetine ((+)-N-methyl 3-(1-naphthalenyloxy)-3-(2-thienyl)-1-aminopropane hydrochloride), is a dual serotonin and norepinephrine uptake inhibitor that is in clinical development for the treatment of depression and stress urinary incontinence.

WO 01/53258 discloses the compound 3-[(phenylmethyl)-(3S)-3-pyrrolidinylamino]-propanenitrile (which may also be named (3S)-3-[N-(2-cyanoethyl)-N-benzylamino]pyrrolidine)

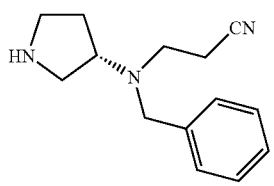

as an intermediate in the synthesis of nitrogenous cyclic compounds which are useful as calcium antagonists.

WO02/24649 discloses a generic class of substituted amino-aza-cycloalkanes as inhibitors of the plasmodium falciparum protease plasmepsin II or related aspartic proteases.

WO91/09844 discloses a generic class of 3-amino-aza-cycloalkanes/alkenes (including the specific compound cis-3-(2-methoxybenzylamino)-2-phenylpyrrolidine) as substance P antagonists.

WO93/01170 discloses another generic class of 3-amino-aza-cycloalkanes/alkenes as substance P antagonists.

WO94/13291 discloses a generic class of cyclic secondary amine derivatives as calcium channel antagonists.

U.S. Pat. No. 4,254,135 discloses 3-amino-pyrrolidines substituted in the 4-position with a hydroxy, loweralkyloxy or phenylcarbonyloxy substituent as being useful in the treatment of depression.

It would be advantageous to provide further compounds which are capable of inhibiting the uptake of one or more monoamines selected from serotonin, norepinephrine and dopamine. Preferably, such compounds would exhibit one or more of the following characteristics when compared with known monoamine uptake inhibitors —(i) improved potency in their inhibition of one or more of these monoamines, (ii) improved selectivity in their inhibition of one or more of these monoamines and (iii) improved pharmacokinetic or pharmacodynamic properties (such as bioavailability, minimal interaction with metabolic enzymes such as CYP2D6 and acid stability).

Accordingly, the present invention provides a compound of formula (I)

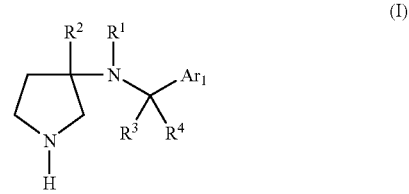

wherein $R^1$ is $C_1$-$C_6$ alkyl (optionally substituted with 1, 2 or 3 halo substituents and/or with 1 substituent selected from —S—($C_1$-$C_3$ alkyl), —O—($C_1$-$C_3$ alkyl) (optionally substituted with 1, 2 or 3 F atoms), —O—($C_3$-$C_6$ cycloalkyl), —$SO_2$—($C_1$-$C_3$ alkyl), —CN, —COO—($C_1$-$C_2$ alkyl) and —OH); $C_2$-$C_6$ alkenyl; —(CH2)$_q$—$Ar_2$; or a group of formula (i) or (ii)

$R^2$, $R^3$ and $R^4$ are each independently selected from hydrogen or $C_1$-$C_2$ alkyl;

$R^5$, $R^6$, $R^7$ and $R^8$ are at each occurrence independently selected from hydrogen or $C_1$-$C_2$ alkyl;

—X— is a bond, —$CH_2$—, —CH═CH—, —O—, —S—, or —$SO_2$—;

—Y— is a bond, —$CH_2$— or —O—;

—Z is hydrogen, —OH or —O—($C_1$-$C_3$ alkyl);

p is 0, 1 or 2;

q is 0, 1 or 2;

r is 0 or 1;

s is 0,1,2 or 3;

t is 0, 1, 2, 3 or 4;

$Ar_1$ is selected from:

(i) a phenyl group or a 5- or 6-membered monocyclic heteroaromatic group each of which is optionally substituted with 1, 2, 3, 4 or 5 substituents (depending on the number of available substitution positions) each independently selected from halo, cyano, $C_1$-$C_4$alkyl (optionally substituted with 1, 2 or 3 F atoms), —O—($C_1$-$C_4$ alkyl) (optionally substituted with 1, 2 or 3 F atoms) and —S—($C_1$-$C_4$ alkyl) (optionally substituted with 1, 2 or 3 F atoms) and/or with 1 substituent selected from pyridinyl, pyrazolyl, phenyl (optionally substituted with 1, 2 or 3 halo substituents), benzyl (optionally substituted with 1, 2 or 3 halo substituents) and phenoxy (optionally substituted with 1, 2 or 3 halo substituents) with the proviso that only $C_1$-$C_4$alkyl may be a substituent for the H of any —NH— moiety present within a 5- or 6-membered monocyclic heteroaromatic group; of (ii) a naphthyl group or an 8-, 9- or 10-membered bicyclic heteroaromatic group each of which is optionally substituted with 1, 2, 3, 4, 5 or 6 substituents (depending on the number of available substitution positions) each independently selected from halo, cyano, $C_1$-$C_4$alkyl (optionally substituted with 1, 2 or 3 F atoms), —O—($C_1$-$C_4$ alkyl) (optionally substituted with 1, 2 or 3 F atoms) and —S—($C_1$-$C_4$ alkyl) (optionally substituted with 1, 2 or 3 F atoms) with the proviso that only $C_1$-$C_4$alkyl may be a substituent for the H of any —NH— moiety present within an 8-, 9- or 10-membered bicyclic heteroaromatic group; and $Ar_2$ is selected from (i) a phenyl group or a 5- or 6-membered monocyclic heteroaromatic group each of which is optionally substituted with 1, 2, 3, 4 or 5 substituents (depending on the number of available substitution positions) each independently selected from halo, cyano, $C_1$-C4alkyl (optionally substituted with 1, 2 or 3 F atoms), —O—($C_1$-$C_4$ alkyl) (optionally substituted with 1, 2 or 3 F atoms) and —S—($C_1$-$C_4$ alkyl) (optionally substituted with 1, 2 or 3 F atoms) with the proviso that only $C_1$-$C_4$alkyl may be a substituent for the H of any —NH— moiety present within a 5- or 6-membered monocyclic heteroaromatic group; or (ii) a naphthyl group or an 8-, 9- or 10-membered bicyclic heteroaromatic group each of which is optionally substituted with 1, 2, 3, 4, 5 or 6 substituents (depending on the number of available substitution positions) each independently selected from halo, cyano, $C_1$-$C_4$alkyl (optionally substituted with 1, 2 or 3 F atoms), —O—($C_1$-$C_4$ alkyl) (optionally substituted with 1, 2 or 3 F atoms) and —S—($C_1$-$C_4$ alkyl) (optionally substituted with 1, 2 or 3 F atoms) with the proviso that only $C_1$-$C_4$alkyl may be a substituent for the H of any —NH— moiety present within an 8-, 9- or 10-membered bicyclic heteroaromatic group;

and pharmaceutically acceptable salts thereof; provided that:
(a) the cyclic portion of the group of formula (i) must contain at least three carbon atoms and not more than seven ring atoms;
(b) when —X— is —CH=CH—, then the cyclic portion of the group of formula (i) must contain at least five carbon atoms; and
(c) when —Z is —OH or —O—($C_1$-$C_3$ alkyl), then —X— is —$CH_2$—;
(d) when —Y— is —O— then p cannot be 0; and
(e) the compound 3-[(phenylmethyl)-(3S)-3-pyrrolidinylamino]-propanenitrile is excluded.

For the avoidance of doubt relating to the term "and/or", when $R^1$ is $C_1$-$C_6$ alkyl, it is substituted with 0, 1, 2 or 3 halo substituents and with 0 or 1 substituent selected from —S—($C_1$-$C_3$ alkyl), —O—($C_1$-$C_3$ alkyl) (optionally substituted with 1, 2 or 3 F atoms), —O—($C_3$-$C_6$ cycloalkyl), —$SO_2$—($C_1$-$C_3$ alkyl), —CN, —COO—($C_1$-$C_2$ alkyl) and —OH.

Similarly, when $Ar_1$ is a phenyl group or a 5- or 6-membered monocyclic heteroaromatic group, each is substituted with 0, 1, 2, 3, 4 or 5 substituents (depending on the number of available substitution positions) each independently selected from halo, cyano, $C_1$-$C_4$alkyl (optionally substituted with 1, 2 or 3 F atoms), —O—($C_1$-$C_4$ alkyl) (optionally substituted with 1, 2 or 3 F atoms) and —S—($C_1$-$C_4$ alkyl) (optionally substituted with 1, 2 or 3 F atoms) and with 0 or 1 substituent selected from pyridinyl, pyrazolyl, phenyl (optionally substituted with 1, 2 or 3 halo substituents), benzyl (optionally substituted with 1, 2 or 3 halo substituents) and phenoxy (optionally substituted with 1, 2 or 3 halo substituents) with the proviso that only $C_1$-$C_4$alkyl may be a substituent for the H of any —NH— moiety present within a 5- or 6-membered monocyclic heteroaromatic group.

For the avoidance of doubt, when p=0, the group of formula (ii) becomes

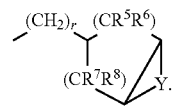

In the present specification the term "$C_1$-$C_6$ alkyl" means a monovalent unsubstituted saturated straight-chain or branched-chain hydrocarbon radical having from 1 to 6 carbon atoms.

In the present specification the term "$C_2$-$C_6$ alkenyl" means a monovalent unsubstituted unsaturated straight-chain or branched-chain hydrocarbon radical having from 2 to 6 carbon atoms and containing at least one carbon-carbon double bond.

In the present specification the term "$C_3$-$C_6$ cycloalkyl" means a monovalent unsubstituted saturated cyclic hydrocarbon radical having from 3 to 6 carbon atoms.

In the present specification the term "$C_1$-$C_6$ alkylene" means a divalent unsubstituted saturated straight-chain or branched-chain hydrocarbon radical having from 1 to 6 carbon atoms. This term is not limited to divalent radicals wherein the radical carbon atoms are located at the termini of the hydrocarbon chain, for example

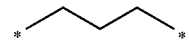

but also include divalent radicals wherein the radical carbon atoms are located within the hydrocarbon chain, for example

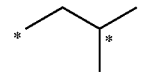

In the present specification the term "halo" or "halogen" means F, Cl, Br or I.

In the present specification the term "$C_1$-$C_4$ difluoroalkyl" means a monovalent unsubstituted saturated straight-chain or branched-chain hydrocarbon radical having from 1 to 4 carbon atoms wherein two hydrogen atoms are substituted with two fluoro atoms. Preferably the two fluoro atoms are attached to the same carbon atom.

In the present specification the term "$C_1$-$C_4$ trifluoroalkyl" means a monovalent unsubstituted saturated straight-chain or branched-chain hydrocarbon radical having from 1 to 4 carbon atoms wherein three hydrogen atoms are substituted with three fluoro atoms. Preferably the three fluoro atoms are attached to the same carbon atom.

In the present specification the term "benzyl" means a monovalent unsubstituted phenyl radical linked to the point of substitution by a —CH$_2$— group.

In the present specification the term "phenoxy" means a monovalent unsubstituted phenyl radical linked to the point of substitution by an O atom.

In the present specification the term "5- or 6-membered monocyclic heteroaromatic group" means a monocyclic aromatic group with a total of 5 or 6 atoms in the ring wherein from 1 to 4 of those atoms are each independently selected from N, O and S. Preferred groups have 1 or 2 atoms in the ring which are each independently selected from N, O and S. Examples of 5-membered monocyclic heteroaromatic groups include pyrrolyl (also called azolyl), furanyl, thienyl, pyrazolyl (also called 1H-pyrazolyl and 1,2-diazolyl), imidazolyl, oxazolyl (also called 1,3-oxazolyl), isoxazolyl (also called 1,2-oxazolyl), thiazolyl (also called 1,3-thiazolyl), isothiazolyl (also called 1,2-thiazolyl), triazolyl, oxadiazolyl, thiadiazolyl, tetrazolyl, oxatriazolyl and thiatriazolyl. Examples of 6-membered monocyclic heteroaromatic groups include pyridinyl, pyrimidyl, pyrazinyl, pyridazinyl and triazinyl.

"Pyrrolyl" as used herein includes pyrrol-1-yl, pyrrol-2-yl and pyrrol-3-yl.

"Furanyl" (also called "furyl") as used herein includes furan-2-yl and furan-3-yl (also called 2-furyl and 3-furyl). Furan-2-yl is preferred.

"Thienyl" (also called "thiophenyl") as used herein includes thien-2-yl and thien-3-yl (also called 2-thiophenyl and 3-thiophenyl).

"Pyrazolyl" as used herein includes pyrazol-1-yl, pyrazol-3-yl, pyrazol-4-yl and pyrazol-5-yl (also called 1-pyrazole, 3-pyrazole, 4-pyrazole and 5-pyrazole). Pyrazol-1-yl is preferred.

"Imidazolyl" as used herein includes imidazol-1-yl, imidazol-2-yl, imidazol-4-yl and imidazol-5-yl.

"Oxazolyl" as used herein includes oxazol-2-yl, oxazol-4-yl and oxazol-5-yl.

"Isoxazolyl" as used herein includes isoxazol-3-yl, isoxazol-4-yl, and isoxazol-5-yl.

"Thiazolyl" as used herein includes thiazol-2-yl, thiazol-4-yl and thiazol-5-yl (also called 2-thiazolyl, 4-thiazolyl and 5-thiazolyl).

"Isothiazolyl" as used herein includes isothiazol-3-yl, isothiazol-4-yl, and isothiazol-5-yl.

"Triazolyl" as used herein includes 1,2,3-triazol-1-yl, 1,2,3-triazol-4-yl, 1,2,3-triazol-5-yl, 1,2,4-triazol-1-yl, 1,2,4-triazol-3-yl and 1,2,4-triazol-5-yl.

"Oxadiazolyl" as used herein includes 1,2,3-oxadiazol-4-yl, 1,2,3-oxadiazol-5-yl, 1,2,4-oxadiazol -3-yl, 1,2,4-oxadiazol-5-yl, 1,2,5-oxadiazol-3-yl and 1,3,4-oxadiazol-2-yl.

"Thiadiazolyl" as used herein includes 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl (also called furazan-3-yl) and 1,3,4-thiadiazol-2-yl.

"Tetrazolyl" as used herein includes tetrazol-1-yl and tetrazol-5-yl.

"Oxatriazolyl" as used herein includes 1,2,3,4-oxatriazol-5-yl and 1,2,3,5-oxatriazol-4-yl.

"Thiatriazolyl" as used herein includes 1,2,3,4-thiatriazol-5-yl and 1,2,3,5-thiatriazol-4-yl.

"Pyridinyl" (also called "pyridyl") as used herein includes pyridin-2-yl, pyridin-3-yl and pyridin-4-yl (also called 2-pyridyl, 3-pyridyl and 4-pyridyl).

"Pyrimidyl" as used herein includes pyrimid-2-yl, pyrimid-4-yl, pyrimid-5-yl and pyrimid-6-yl.

"Pyridazinyl" as used herein includes pyridazin-3-yl and pyridazin-4-yl.

"Pyrazinyl" as used herein includes pyrazin-2-yl and pyrazin-3-yl.

"Triazinyl" as used herein includes 1,3,5-triazin-2-yl, 1,2,4-triazin-3-yl, 1,2,4-triazin-5-yl, 1,2,4-triazin-6-yl, 1,2,3-triazin-4-yl and 1,2,3-triazin-5-yl.

In the present specification the term "8-, 9- or 10-membered bicyclic heteroaromatic group" means a fused bicyclic aromatic group with a total of 8, 9 or 10 atoms in the ring system wherein from 1 to 4 of those atoms are each independently selected from N, O and S. Preferred groups have from 1 to 3 atoms in the ring system which are each independently selected from N, O and S. Suitable 8-membered bicyclic heteroaromatic groups include imidazo[2,1-b][1,3]thiazolyl, thieno[3,2-b]thienyl, thieno[2,3-d][1,3]thiazolyl and thieno[2,3-d]imidazolyl. Suitable 9-membered bicyclic heteroaromatic groups include indolyl, isoindolyl, benzofuranyl (also called benzo[b]furanyl), isobenzofuranyl (also called benzo[c]furanyl), benzothienyl (also called benzo[b]thienyl), isobenzothienyl (also called benzo[c]thienyl), indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl and imidazo[1,2-a]pyridine. Suitable 10-membered bicyclic heteroaromatic groups include quinolinyl, isoquinolinyl, cinnolinyl, quinazolinyl, quinoxalinyl, 1,5-naphthyridyl, 1,6-naphthyridyl, 1,7-naphthyridyl and 1,8-naphthyridyl.

"Imidazo[2,1-b][1,3]thiazolyl" as used herein includes imidazo[2,1-b][1,3]thiazoi-2-yl, imidazo[2,1-b][1,3]thiazol-3-yl, imidazo[2,1-b][1,3]thiazol-5-yl and imidazo[2,1-b][1,3]thiazol-6-yl.

"Thieno[3,2-b]thienyl" as used herein includes thieno[3,2-b]thien-2-yl, thieno[3,2-b]thien-3-yl, thieno[3,2-b]thien-5-yl and thieno[3,2-b]thien-6-yl.

"Thieno[2,3-d][1,3]thiazolyl" as used herein includes thieno[2,3-d][1,3]thiazol-2-yl, thieno[2,3-d][1,3]thiazol-5-yl and thieno[2,3-d][1,3]thiazol-6-yl.

"Thieno[2,3-d]imidazolyl" as used herein includes thieno[2,3-d]imidazol-2-yl, thieno[2,3-d]imidazol-4-yl and thieno[2,3-d]imidazol-5-yl.

"Indolyl" as used herein includes indol-1-yl, indol-2-yl, indol-3-yl,-indol-4-yl, indol-5-yl, indol-6-yl and indol-7-yl.

"Isoindolyl" as used herein includes isoindol-1-yl, isoindol-2-yl, isoindol-3-yl, isoindol-4-yl, isoindol-5-yl, isoindol-6-yl and isoindol-7-yl.

"Benzofuranyl" as used herein includes benzofuran-2-yl, benzofuran-3-yl, benzofuran-4-yl, benzofuran-5-yl, benzofuran-6-yl and benzofuran-7-yl.

"Isobenzofuranyl" as used herein includes isobenzofuran-1-yl, isobenzofuran-3-yl, isobenzofuran-4-yl, isobenzofuran-5-yl, isobenzofuran-6-yl and isobenzofuran-7-yl.

"Benzothienyl" (also called "benzothiophenyl") as used herein includes benzothien-2-yl, benzothien-3-yl, benzothien-4-yl, benzothien-5-yl, benzothien-6-yl and benzothien-7-yl (also called 2-benzo[b]thiophenyl, 3-benzo[b]thiophenyl, 4-benzo[b]thiophenyl, 5-benzo[b]thiophenyl, 6-benzo[b]thiophenyl and -7-benzo[b]thiophenyl).

"Isobenzothienyl" as used herein includes isobenzothien-1-yl, isobenzothien-3-yl, isobenzothien-4-yl, isobenzothien-5-yl, isobenzothien-6-yl and isobenzothien-7-yl.

"Indazolyl" as used herein includes indazol-1-yl, indazol-3-yl, indazol-4-yl, indazol-5-yl, indazol-6-yl and indazol-7-yl.

"Benzimidazolyl" as used herein includes benzimidazol-1-yl, benzimidazol-2-yl, benzimidazol-4-yl, benzimidazol-5-yl, benzimidazol-6-yl and benzimidazol-7-yl.

"1,3-Benzoxazolyl" as used herein includes 1,3-benzoxazol-2-yl, 1,3-benzoxazol-4-yl, 1,3-benzoxazol-5-yl, 1,3-benzoxazol-6-yl and 1,3-benzoxazol-7-yl.

"1,2-Benzisoxazolyl" as used herein includes 1,2-benzisoxazol-3-yl, 1,2-benzisoxazol-4-yl, 1,2-benzisoxazol-5-yl, 1,2-benzisoxazol-6-yl and 1,2-benzisoxazol-7-yl.

"2,1-Benzisoxazolyl" as used herein includes 2,1-benzisoxazol-3-yl, 2,1-benzisoxazol-4-yl, 2,1-benzisoxazol-5-yl, 2,1-benzisoxazol-6-yl and 2,1-benzisoxazol-7-yl.

"1,3-Benzothiazolyl" as used herein includes 1,3-benzothiazol-2-yl, 1,3-benzothiazol-4-yl, 1,3-benzothiazol-5-yl, 1,3-benzothiazol-6-yl and 1,3-benzothiazol-7-yl.

"1,2-Benzoisothiazolyl" as used herein includes 1,2-benzisothiazol-3-yl, 1,2-benzisothiazol-4-yl, 1,2-benzisothiazol-5-yl, 1,2-benzisothiazol-6-yl and 1,2-benzisothiazol-7-yl.

"2,1-Benzoisothiazolyl" as used herein includes 2,1-benzisothiazol-3-yl, 2,1-benzisothiazol-4-yl, 2,1-benzisothiazol-5-yl, 2,1-benzisothiazol-6-yl and 2,1-benzisothiazol-7-yl.

"Benzotriazolyl" as used herein includes benzotriazol-1-yl, benzotriazol4-yl, benzotriazol-5-yl, benzotriazol-6-yl and benzotriazol-7-yl.

"1,2,3-Benzoxadiazolyl" as used herein includes 1,2,3-benzoxadiazol-4-yl, 1,2,3-benzoxadiazol-5-yl, 1,2,3-benzoxadiazol-6-yl and 1,2,3-benzoxadiazol-7-yl.

"2,1,3-Benzoxadiazolyl" as used herein includes 2,1,3-benzoxadiazol-4-yl, 2,1,3-benzoxadiazol-5-yl, 2,1,3-benzoxadiazol-6-yl and 2,1,3-benzoxadiazol-7-yl.

"1,2,3-Benzothiadiazolyl" as used herein includes 1,2,3-benzothiadiazol-4-yl, 1,2,3-benzothiadiazol-5-yl, 1,2,3-benzothiadiazol-6-yl and 1,2,3-benzothiadiazol-7-yl.

"2,1,3-Benzothiadiazolyl" as used herein includes 2,1,3-benzothiadiazol-4-yl, 2,1,3-benzothiadiazol-5-yl, 2,1,3-benzothiadiazol-6-yl and 2,1,3-benzothiadiazol-7-yl.

"Thienopyridinyl" as used herein includes thieno[2,3-b]pyridinyl, thieno[2,3-c]pyridinyl, thieno[3,2-c]pyridinyl and thieno[3,2-b]pyridinyl.

"Purinyl" as used herein includes purin-2-yl, purin-6-yl, purin-7-yl and purin-8-yl.

"Imidazo[1,2-a]pyridinyl" as used herein includes imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl and imidazo[1,2-a]pyridin-7-yl.

"Quinolinyl" as used herein includes quinolin-2-yl, quinolin-3-yl, quinolin-4-yl, quinolin-5-yl, quinolin-6-yl, quinolin-7-yl and quinolin-8-yl.

"Isoquinolinyl" as used herein includes isoquinolin-1-yl, isoquinolin-3-yl, isoquinolin-4-yl, isoquinolin-5-yl, isoquinolin-6-yl, isoquinolin-7-yl and isoquinolin-8-yl.

"Cinnolinyl" as used herein includes cinnolin-3-yl, cinnolin-4-yl, cinnolin-5-yl, cinnolin-6-yl, cinnolin-7-yl and cinnolin-8-yl.

"Quinazolinyl" as used herein includes quinazolin-2-yl, quinazolin-4-yl, quinazolin-5-yl, quinazolin-6-yl, quinazolin-7-yl and quinazolin-8-yl.

"1,4-Naphthyridyl" as used herein includes 1,4-naphthyrid-2-yl, 1,4-naphthyrid-3-yl, 1,4-naphthyrid-5-yl, 1,4-naphthyrid-6-yl, 1,4-naphthyrid-7-yl and 1,4-naphthyrid-8-yl.

"1,5-Naphthyridyl" as used herein includes 1,5-naphthyrid-2-yl, 1,5-naphthyrid-3-yl, 1,5-naphthyrid-4-yl, 1,5-naphthyrid-6-yl, 1,5-naphthyrid-7-yl and 1,5-naphthyrid-8-yl.

"1,6-Naphthyridyl" as used herein includes 1,6-naphthyrid-2-yl, 1,6-naphthyrid-3-yl, 1,6-naphthyrid-4-yl, 1,6-naphthyrid-5-yl, 1,6-naphthyrid-7-yl and 1,6-naphthyrid-8-yl.

"1,7-Naphthyridyl" as used herein includes 1,7-naphthyrid-2-yl, 1,7-naphthyrid-3-yl, 1,7-naphthyrid-4-yl, 1,7-naphthyrid-5-yl, 1,7-naphthyrid-6-yl and 1,7-naphthyrid-8-yl.

"1,8-Naphthyridyl" as used herein includes 1,8-naphthyrid-2-yl, 1,8-naphthyrid-3-yl, 1,8-naphthyrid-4-yl, 1,8-naphthyrid-5-yl, 1,8-naphthyrid-6-yl and 1,8-naphthyrid-7-yl.

In the present specification the term "naphthyl" includes 1-naphthyl, and 2-naphthyl. 1-naphthyl is preferred.

In the above definitions, similar terms specifying different numbers of C atoms take an analogous meaning. For example the terms "$C_1$-$C_4$ alkyl" and "$C_1$-$C_3$ alkyl" mean a monovalent unsubstituted saturated straight-chain or branched-chain hydrocarbon radical having from 1 to 4 and 1 to 3 carbon atoms respectively. The term "$C_1$-$C_4$ alkyl" includes methyl, ethyl, n-propyl, iso-propyl, n-butyl, iso-butyl, sec-butyl, and tert-butyl. The term "$C_1$-$C_3$ alkyl" includes methyl, ethyl, n-propyl and iso-propyl.

It will be appreciated that when s is 2 or 3, then each $R^5$ and/or each $R^6$ can be different. In the same way when t is 2 or 3, then each $R^7$ and/or each $R^8$ can be different.

In a preferred embodiment of the present invention, $Ar_1$ is phenyl, pyridinyl, thiazolyl, benzothiophenyl or naphthyl; wherein said phenyl, pyridinyl or thiazolyl group may be substituted with 1, 2 or 3 substituents each independently selected from halo, cyano, $C_1$-$C_4$ alkyl (optionally substituted with 1, 2 or 3 F atoms), —O—($C_1$-$C_4$ alkyl) (optionally substituted with 1, 2 or 3 F atoms) and —S—($C_1$-$C_4$ alkyl) (optionally substituted with 1, 2 or 3 F atoms) and/or with 1 substituent selected from pyridinyl, pyrazolyl, phenyl (optionally substituted with 1, 2 or 3 halo substituents) and phenoxy (optionally substituted with 1, 2 or 3 halo substituents); and wherein said benzothiophenyl or naphthyl group may be optionally substituted with 1, 2 or 3 substituents each independently selected from halo, cyano, $C_1$-$C_4$ alkyl (optionally substituted with 1, 2 or 3 F atoms), —O—($C_1$-$C_4$ alkyl) (optionally substituted with 1, 2 or 3 F atoms), and —S—($C_1$-$C_4$ alkyl) (optionally substituted with 1, 2 or 3 F atoms); and $Ar_2$ is naphthyl, pyridinyl, thiazolyl, furanyl, thiophenyl, benzothiophenyl, or phenyl, wherein said naphthyl, pyridinyl, thiazolyl, furanyl, thiophenyl, benzothiophenyl, or phenyl may be substituted with 1, 2 or 3 substituents each independently selected from halo, $C_1$-$C_4$ alkyl (optionally substituted with 1, 2 or 3 F atoms) and —O—($C_1$-$C_4$ alkyl) (optionally substituted with 1, 2 or 3 F atoms).

In a preferred embodiment of the present invention, when R1 is a group of formula (i) and r is 0, Z is H.

In a preferred embodiment of the present invention $R^1$ is $C_1$-$C_6$ alkyl, $C_2$-$C_6$ alkenyl, —$(CH_2)_m$—$CF_3$, —$(CH_2)_n$—S—($C_1$-$C_3$ alkyl), —$CH_2$—COO—($C_1$-$C_2$ alkyl), —($C_1$-$C_5$ alkylene)—O—($C_1$-$C_3$ alkyl), —($C_1$-$C_5$ alkylene)—O—($C_3$-$C_6$ cycloalkyl), —($C_1$-$C_5$ alkylene)—$SO_2$—($C_1$-$C_3$ alkyl), —($C_1$-$C_5$ alkylene)—$OCF_3$, —($C_1$-$C_6$ alkylene)—OH, —($C_1$-$C_5$ alkylene)—CN, —$(CH_2)_q$—$Ar_2$ or a group of formula (ia), (ib) or (ii)

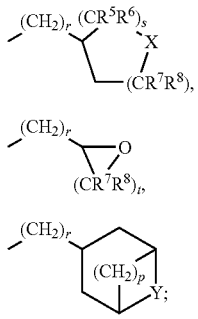

R², R³, R⁴, R⁵, R⁶, R⁷, R⁸, —X—, —Y—, p, q, r and s have the values defined above;

m is 1, 2 or 3;
n is 1, 2 or 3;
t is 2, 3 or 4;
$Ar_1$ is phenyl, pyridinyl, thiazolyl or naphthyl; wherein said phenyl, pyridinyl or thiazolyl group may be substituted with 1, 2 or 3 substituents each independently selected from halo, trifluoromethyl, cyano, $C_1$-$C_4$ alkyl, —O—($C_1$-$C_4$ alkyl), —O—($C_1$-$C_4$ difluoroalkyl), —O—($C_1$-$C_4$ trifluoroalkyl), —S—($C_1$-$C_4$ alkyl), —S—($C_1$-$C_2$ trifluoroalkyl) and/or with 1 substituent selected from pyridinyl, pyrazolyl, phenyl (optionally substituted with 1, 2 or 3 halo substituents) and phenoxy (optionally substituted with 1, 2 or 3 halo substituents); and wherein said naphthyl group may be optionally substituted with 1, 2 or 3 substituents each independently selected from halo, trifluoromethyl, cyano, $C_1$-$C_4$ alkyl, —O—($C_1$-$C_4$ alkyl), —O—($C_1$-$C_4$ difluoroalkyl), —O—($C_1$-$C_4$ trifluoroalkyl), —S—($C_1$-$C_4$ alkyl), —S—($C_1$-$C_2$ trifluoroalkyl);
$Ar_2$ is naphthyl, pyridinyl, thiazolyl, furanyl, thiophenyl, benzothiophenyl, or phenyl, wherein said naphthyl, pyridinyl, thiazolyl, furanyl, thiophenyl, benzothiophenyl, or phenyl may be substituted with 1, 2 or 3 substituents each independently selected from halo, $C_1$-$C_4$ alkyl, trifluoromethyl and —O—($C_1$-$C_4$ alkyl).

In a preferred embodiment of the present invention $R^2$ is hydrogen. In another preferred embodiment of the present invention $R^3$ and $R^4$ are hydrogen. More preferably $R^2$, $R^3$ and $R^4$ are hydrogen.

In a preferred embodiment of the present invention each $R^5$ and $R^6$ is hydrogen. In another preferred embodiment of the present invention each $R^7$ and $R^8$ is hydrogen. More preferably $R^5$, $R^6$, $R^7$ and $R^8$ are hydrogen.

In a preferred embodiment of the present invention $R^1$ is $C_1$-$C_6$ alkyl. More preferably $R^1$ is n-propyl, 1-methylethyl, 2-methylpropyl, or 3,3-dimethylpropyl.

In another preferred embodiment of the present invention $R^1$ is —($C_4$-$C_5$ alkylene)—OH. More preferably $R^1$ is 2,2-dimethyl-2-hydroxyethyl or 3,3-dimethyl-3-hydroxypropyl.

In another preferred embodiment of the present invention $R^1$ is a group of formula (i) and each $R^5$ and $R^6$ is hydrogen. More preferably each $R^5$, $R^6$, $R^7$ and $R^8$ is hydrogen.

In another preferred embodiment of the present invention $R^1$ is a group of formula (ii) and each $R^5$ and $R^6$ is hydrogen. More preferably each $R^5$, $R^6$, $R^7$ and $R^8$ is hydrogen.

In another preferred embodiment of the present invention $R^1$ is a group of formula (i), r is 0, s is 2, t is 2, —Z is hydrogen and —X— is —O—, —S— or —SO₂—. More preferably $R^1$ is a group of formula (i), r is 0, s is 2, t is 1 or 2, —Z is hydrogen and —X— is —O—.

In another preferred embodiment of the present invention $R^1$ is a group of formula (i), r is 0, s is 1, 2 or 3, t is 1, —Z is hydrogen and —X— is —$CH_2$—.

In another preferred embodiment of the present invention $R^1$ is a group of formula (i), r is 1, s is 0, 1, 2 or 3, t is 1, —Z is hydrogen and —X— is —$CH_2$—.

In another preferred embodiment of the present invention $R^1$ is a group of the formula (ia). More preferably $R^1$ is a group of the formula (ia) and each $R^5$, $R^6$, $R^7$ and $R^8$ is hydrogen.

In another preferred embodiment of the present invention $R^1$ is a group of the formula (ib). More preferably $R^1$ is a group of the formula (ib), r is 1, t is 3, and each $R^7$ and $R^8$ is hydrogen.

In another preferred embodiment of the present invention $R^1$ is —$(CH_2)_m$—$CF_3$. More preferably $R^1$ is —$(CH_2)_m$—$CF_3$ and m is 1, 2, or 3.

In another preferred embodiment of the present invention $R^1$ is —$(CH_2)_n$—S—($C_1$-$C_3$ alkyl). More preferably $R^1$ is —$(CH_2)_3$—S—$CH_3$.

In another preferred embodiment of the present invention $R^1$ is —$CH_2$—COO—($C_1$-$C_2$ alkyl). More preferably $R^1$ is —$CH_2$—$COOCH_3$.

In another preferred embodiment of the present invention $R^1$ is —($C_1$-$C_5$ alkylene)—O—($C_1$-$C_3$ alkyl). More preferably $R^1$ is —($C_3$-$C_4$ alkylene)—$OCH_3$.

In another preferred embodiment of the present invention $R^1$ is —($C_1$-$C_5$ alkylene)—O—($C_3$-$C_6$ cycloalkyl). More preferably $R^1$ is —$CH_2$—$CH_2$—O—cyclobutyl.

In another preferred embodiment of the present invention $R^1$ is —($C_1$-$C_5$ alkylene)—$SO_2$—($C_1$-$C_3$ alkyl).

In another preferred embodiment of the present invention $R^1$ is —($C_1$-$C_5$ alkylene)—$OCF_3$. More preferably $R^1$ is —$CH_2$—$CH_2$—$OCF_3$.

In another preferred embodiment of the present invention $R^1$ is —($C_1$-$C_5$ alkylene)—CN. More preferably $R^1$ is —($C_2$-$C_4$ alkylene)—CN. Most preferably $R^1$ is —$CH_2$—$CH_2$—CN or —$CH_2$—$C(CH_3)_2$—CN.

In another preferred embodiment of the present invention $R^1$ is —$(CH_2)_q$—$Ar_2$, and q is 1. More preferably $R^1$ is —$(CH_2)_q$—$Ar_2$, q is 1 and —$Ar_2$ is pyridiniyl, phenyl or phenyl substituted with 1, 2 or 3 substituents each independently selected from halo, trifluoromethyl or $C_1$-$C_4$ alkyl.

In another preferred embodiment of the present invention —$Ar_1$ is phenyl; phenyl substituted with 1, 2 or 3 substituents each independently selected from halo, trifluoromethyl and $C_1$-$C_4$ alkyl and/or with 1 substituent selected from phenyl, phenyl substituted with 1, 2 or 3 halo substituents, pyridinyl, pyrazolyl, phenoxy and phenoxy substituted with 1, 2 or 3 halo substituents; pyridinyl, or pyridinyl substituted with 1, 2 or 3 substituents each independently selected from halo, trifluoromethyl and $C_1$-$C_4$ alkyl and/or with 1 substituent selected from phenyl and phenyl substituted with 1, 2 or 3 halo substituents. More preferably —$Ar_1$ is phenyl or phenyl substituted with 1, 2 or 3 substituents each independently selected from halo, trifluoromethyl and $C_1$-$C_4$ alkyl and/or with 1 substituent selected from phenyl, phenyl substituted with 1, 2 or 3 halo substituents, pyridinyl, pyrazolyl, phenoxy and phenoxy substituted with 1, 2 or 3 halo substituents. Most preferably —$Ar_1$ is phenyl substituted with 1 or 2 substituents each independently selected from halo, trifluoromethyl and $C_1$-$C_4$ alkyl and/or with 1 substituent selected from phenyl, phenyl substituted with 1, 2 or 3 halo substituents, pyridinyl, pyrazolyl, phenoxy and phenoxy substituted with 1, 2 or 3 halo substituents. Suitable —$Ar_1$ groups include, for example, 2-methylthiophenyl, 2-methylphenyl, 2-fluorophenyl, 2-chlorophenyl, 2-isopropoxyphenyl, 2-trifluoromethylphenyl, 2-difluoromethoxyphenyl, 2-methoxyphenyl, 2-ethoxyphenyl, 2-(1,1'-biphenyl), 2-phenoxyphenyl, 2-benzylphenyl, 3-trifluoromethoxyphenyl, 3-chlorophenyl, 3-trifluoromethylphenyl, 3-methylphenyl, 3-trifluorothiomethoxyphenyl, 3-methoxyphenyl, 4-trifluoromethylphenyl, 4-chlorophenyl, 4-fluorophenyl, 3,5-dichlorophenyl, 3,5-dimethylphenyl, 3-trifluoromethyl-5-fluorophenyl, 3,5-difluorophenyl, 2,3-dichlorophenyl, 2,3-dimethylphenyl, 2-chloro-3-trifluoromethylphenyl, 2-chloro-3-methylphenyl, 2-methyl-3-chlorophenyl, 2,4-dichlorophenyl, 2,4-dimethyl, 2,4-difluorophenyl, 2-chloro-4-fluorophenyl, 2-trifluoromethyl-4-fluorophenyl, 2-fluoro-4-trifluoromethylphenyl, 2-methyl-4-chlorophenyl, 2-methoxy-4-fluorophenyl, 2-trifluoromethyl-5-fluorophenyl, 2,5-dimethylphenyl, 4-fluoro-[1,1'-biphenyl]-2-yl, 2-chloro-5-fluorophenyl, 2-(trifluoromethyl)-6-fluorophenyl, 2-chloro-6-fluorophenyl, 3,4-dichlorophenyl, and 3-chloro-4-fluorophenyl. In general when —Ar$_1$ is phenyl substituted with pyridinyl, 3-pyridinyl is preferred.

In another preferred embodiment of the present invention —Ar$_1$ is pyridinyl or pyridinyl substituted with 1, 2 or 3 substituents each independently selected from halo, trifluoromethyl and C$_1$-C$_4$ alkyl and/or with 1 substituent selected from phenyl and phenyl substituted with 1, 2 or 3 halo substituents. More preferably —Ar$_1$ is pyridinyl substituted with 1 or 2 substituents each independently selected from halo, trifluoromethyl and C$_1$-C$_4$ alkyl and/or with 1 substituent selected from phenyl and phenyl substituted with 1, 2 or 3 halo substituents. Suitable —Ar$_1$ groups include, for example, 3-phenyl-2-pyridinyl. In general when —Ar$_1$ is a substituted pyridinyl, substituted 2-pyridinyl is preferred.

Illustrative of the present invention are the compounds identified below or their pharmaceutically acceptable salts:

1: (3S)-N-(1-Methylethyl)-N-{[3,5-dichlorophenyl]-methyl}pyrrolidin-3-amine,
2: (3S)-N-(1-Methylethyl)-N-{[2-(methylthio)phenyl]methyl}-pyrrolidin-3-amine,
3: (3S)-N-(1-Methylethyl)-N-{[2-trifluoromethyl)oxy]-phenyl}methyl)pyrrolidin-3-amine,
4: (3S)-N-[(3,5-Dimethylphenyl)methyl]-N-(1-methylethyl)-pyrrolidin-3-amine,
5: (3S)-N-[(3-Chlorophenyl)methyl]-N-(1-methylethyl)-pyrrolidin-3-amine,
6: (3S)-N-[(2,3-Dichlorophenyl)methyl]-N-(1-methylethyl)-pyrrolidin-3-amine,
7: (3S)-N-[(2,3-Dimethylphenyl)methyl]-N-(1-methylethyl)-pyrrolidin-3-amine,
8: (3S)-N-[(2,4-Dichlorophenyl)methyl]-N-(1-methylethyl)-pyrrolidin-3-amine,
9: (3S)-N-(Cyclohexylmethyl)-N-[(2-methylphenyl)methyl]-pyrrolidin-3-amine,
10: (3S)-N-(Cyclohexylmethyl)-N-{[2-(methylthio)phenyl]-methyl}pyrrolidin-3-amine,
11: (3S)-N-(Cyclohexylmethyl)-N-[(2-fluorophenyl)methyl]-pyrrolidin-3-amine,
12: (3S)-N-(Cyclohexylmethyl)-N-(naphthalene-1-ylmethyl)-pyrrolidin-3-amine,
13: (3S)-N-[(2-Chlorophenyl)methyl]-N-(cyclohexylmethyl)-pyrrolidin-3-amine,
14: (3S)-N-(Cyclohexylmethyl)-N-({2-[1-(methylethyl)oxy]-phenyl}methyl)pyrrolidin-3-amine,
15: (3S)-N-Cyclopentyl-N-[(2,4-dichlorophenyl)methyl]-pyrrolidin-3-amine,
16: (3S)-N-Cyclopentyl-N-{[2-(trifluoromethyl)phenyl]methyl}-pyrrolidin-3-amine,
17: (3S)-N-Cyclopentyl-N-[(3-chlorophenyl)methyl]-pyrrolidin-3-amine,
18: (3S)-N-Cyclopentyl-N-[(2-chlorophenyl)methyl]-pyrrolidin-3-amine,
19: (3S)-N-Cyclopentyl-N-{[4-(trifluoromethyl)phenyl]methyl}-pyrrolidin-3-amine,
20: (3S)-N-Cyclopentyl-N-{[2-(methylthio)phenyl]methyl}-pyrrolidin-3-amine,
21: (3S)-N-Cyclopentyl-N-{[3-(trifluoromethyl)phenyl]methyl}-pyrrolidin-3-amine,
22: (3S)-N-Cyclopentyl-N-{[5-fluoro-2-(trifluoromethyl)-phenyl]methyl}-pyrrolidin-3-amine,
23: (3S)-N-Cyclopentyl-N-{[2-(difluoromethoxy)phenyl]methyl}-pyrrolidin-3-amine,
24: (3S)-N-Cyclopentyl-N-{[5-fluoro-2-(trifluoromethyl)-phenyl]methyl}-pyrrolidin-3-amine,
25: (3S)-N-Cyclopentyl-N-[(2,4-dimethylphenyl)methyl]-pyrrolidin-3-amine,
26: (3S)-N-Cyclopentyl-N-[(3,5-dimethylphenyl)methyl]-pyrrolidin-3-amine,
27: (3S)-N-Cyclopentyl-N-[(2,5-dimethylphenyl)methyl]-pyrrolidin-3-amine,
28: (3S)-N-Cyclopentyl-N-[(2,4-difluorophenyl)methyl]-pyrrolidin-3-amine,
29: (3S)-N-Cyclopentyl-N-{[5-fluoro-3-(trifluoromethyl)-phenyl]methyl}-pyrrolidin-3-amine,
30: (3S)-N-Cyclopentyl-N-[(3-methylphenyl)methyl]-pyrrolidin-3-amine,
31: (3S)-N-Cyclopentyl-N-[(2,3-dimethylphenyl)methyl]-pyrrolidin-3-amine,
32: (3S)-N-Cyclopentyl-N-[(2,3-dichlorophenyl)methyl]-pyrrolidin-3-amine,
33: (3S)-N-Cyclopentyl-N-[(2-chloro-6-fluorophenyl)methyl]-pyrrolidin-3-amine,
34: (3S)-N-Cyclopentyl-N-[(3,5-difluorophenyl)methyl]-pyrrolidin-3-amine,
35: (3S)-N-Cyclopentyl-N-[(3,5-dichlorophenyl)methyl]-pyrrolidin-3-amine,
36: (3S)-N-Cyclopentyl-N-{[2-chloro-3-(trifluoromethyl)-phenyl]methyl}-pyrrolidin-3-amine,
37: (3S)-N-[2-Chlorophenyl)methyl]-N-propylpyrrolidin-3-amine,
38: (3S)-N-Propyl-N-{[2-(trifluoromethyl)phenyl]methyl}-pyrrolidin-3-amine,
39: (3S)-N-{5-Fluoro-2-(trifluoromethyl)phenyl]methyl}-N-propylpyrrolidin-3-amine,
40: (3S)-N-Cyclobutyl-N-{[5-fluoro-2-(trifluoromethyl)-phenyl]methyl}-pyrrolidin-3-amine,
41: (3S)-N-Cyclobutyl-N-[(2,3-dichlorophenyl)methyl]-pyrrolidin-3-amine,
42: (3S)-N-Cyclohexyl-N-[(3-methylphenyl)methyl]-pyrrolidin-3-amine,
43: (3S)-N-Cyclohexyl-N-{[2-(methylthio)phenyl]methyl}-pyrrolidin-3-amine,
44: (3S)-N-Cyclohexyl-N-{[2-(trifluoromethyl)phenyl]methyl}-pyrrolidin-3-amine,
45: (3S)-N-Cyclohexyl-N-{[3-(trifluoromethylthio)phenyl]methyl}-pyrrolidin-3-amine,
46: (3S)-N-Cyclohexyl-N-[(2,4-dichlorophenyl)methyl]-pyrrolidin-3-amine,
47: (3S)-N-Cyclohexyl-N-[(3,5-dichlorophenyl)methyl]-pyrrolidin-3-amine,
48: (3S)-N-Cyclohexyl-N-[(2,3-dichlorophenyl)methyl]-pyrrolidin-3-amine,
49: (3S)-N-[(2,4-Dichlorophenyl)methyl]-N-(2-methoxy-1-methylethyl)pyrrolidin-3-amine,
50: (3S)-N-[(2-Chloro-4-fluorophenyl)methyl]-N-(2-methoxy-1-methylethyl)pyrrolidin-3-amine, 51: (3S)-N-[(3,5-Dichlorophenyl)methyl]-N-(2-methoxy-1-methylethyl)pyrrolidin-3-amine,
52: (3S)-N-[(2,3-Dichlorophenyl)methyl]-N-(2-methylpropyl)-pyrrolidin-3-amine,
53: (3S)-N-{[2-Chloro-4-fluorophenyl]methyl}-N-(1-methylethyl)pyrrolidin-3-amine,
54: (3S)-N-{[4-Fluoro-2-(trifluoromethyl)phenyl]methyl}-N-(1-methylethyl)-pyrrolidin-3-amine,
55: (3S)-N-{[2-Fluoro-4-(trifluoromethyl)phenyl]methyl}-N-(1-methylethyl)-pyrrolidin-3-amine,
56: (3S)-N-[(3,4-Dichlorophenyl)methyl]-N-(1-methylethyl)-pyrrolidin-3-amine,
57: (3S)-N-[(3,5-Dichlorophenyl)methyl]-N-(1-methylethyl)-pyrrolidin-3-amine,
58: (3S)-N-[(4-Chlorophenyl)methyl]-N-(1-methylethyl)-pyrrolidin-3-amine,
59: (3S)-N-[(3-Methoxyphenyl)methyl]-N-(1-methylethyl)-pyrrolidin-3-amine,
60: (3S)-N-[(3-Cyano-4-fluorophenyl)methyl]-N-(1-methylethyl)-pyrrolidin-3-amine,
61: (3S)-N-[(2,3-Dimethylphenyl)methyl]-N-(1-methylethyl)-pyrrolidin-3-amine,
62: (3S)-N-{[(2-Chloro-3-(trifluoromethyl)phenyl]methyl}-N-(1-methylethyl)-pyrrolidin-3-amine,
63: (3S)-N-[(2-Chloro-6-fluorophenyl)methyl]-N-(1-methylethyl)-pyrrolidin-3-amine,
64: (3S)-N-[(2,4-Chlorophenyl)methyl]-N-(1-methylethyl)-pyrrolidin-3-amine,
65: (3S)-N-{[2-(4-Fluorophenoxy)phenyl]methyl}-N-(1-methylethyl)-pyrrolidin-3-amine,
66: (3S)-N-{[2-(3,4-Difluorophenoxy)phenyl]methyl}-N-(1-methylethyl)-pyrrolidin-3-amine,
67: (3S)-N-{(4'-Fluoro-[1,1'-biphenyl]-2-yl)methyl}-N-(1-methylethyl)-pyrrolidin-3-amine,
68: (3S)-N-{[4-Fluoro-2-(trifluoromethyl)phenyl]methyl}-N-propylpyrrolidin-3-amine,
69: (3S)-N-Butyl-N-{[4-fluoro-2-(trifluoromethyl)phenyl]methyl}pyrrolidin-3-amine,
70: (3S)-N-Cyclopropylmethyl-N-{[4-fluoro-2-(trifluoromethyl)phenyl]-methyl}pyrrolidin-3-amine,
71: (3S)-N-[(3,5-Dichlorophenyl)methyl]-N-propylpyrrolidin-3-amine,
72: (3S)-N-Butyl-N-[(3,5-dichlorophenyl)methyl]pyrrolidin-3-amine,
73: (3S)-N-Cyclopropylmethyl-N-[(3,5-dichlorophenyl)-methyl]pyrrolidin-3-amine,
74: (3S)-N-[(2,4-Dichlorophenyl)methyl]-N-propylpyrrolidin-3-amine,
75: (3S)-N-Butyl-N-[(2,4-dichlorophenyl)methyl]pyrrolidin-3-amine,
76: (3S)-N-Cyclopropylmethyl-N-[(2,4-dichlorophenyl)-methyl]pyrrolidin-3-amine,
77: (3S)-N-[(2-Chloro-4-fluorophenyl)methyl]-N-propylpyrrolidin-3-amine,
78: (3S)-N-Butyl-N-[(2-chloro-4-fluorophenyl)methyl]-pyrrolidin-3-amine,
79: (3S)-N-[(2-Chloro-4-fluorophenyl)methyl]-N-(cyclopropylmethyl)pyrrolidin-3-amine,
80: (3S)-N-{[4-Fluoro-2-(trifluoromethyl)phenyl]methyl}-N-(tetrahydro-2H-thiopyran-4-yl)pyrrolidin-3-amine,
81: (3S)-N-[(2,4-Dichlorophenyl)methyl]-N-(tetrahydro-2H-thiopyran-4-yl)pyrrolidin-3-amine,
82: (3S)-N-[(2,4-Dichlorophenyl)methyl]-N-(1,1-dioxidotetrahydro-2H-thiopyran-4-yl)pyrrolidin-3-amine,
83: (3S)-N-{[5-Fluoro-2-(trifluoromethyl)phenyl]methyl}-N-(tetrahydro-2H-pyran-4-yl)pyrrolidin-3-amine,
84: (3S)-N-{[2-(Trifluoromethyl)phenyl]methyl}-N-(tetrahydro-2H-pyran-4-yl)pyrrolidin-3-amine,
85: (3S)-N-[(2,4-Dichlorophenyl)methyl]-N-(tetrahydro-2H-pyran-4-yl)pyrrolidin-3-amine,
86: (3S)-N-[(3,5-Dichlorophenyl)methyl]-N-(tetrahydro-2H-pyran-4-yl)pyrrolidin-3-amine,
87: (3S)-N-[(2-Chloro-4-fluorophenyl)methyl]-N-(tetrahydro-2H-pyran-4-yl)pyrrolidin-3-amine,
88: (3S)-N-[(4-Chloro-2-methylphenyl)methyl]-N-(tetrahydro-2H-pyran-4-yl)pyrrolidin-3-amine,
89: (3S)-N-[(2,3-Dichlorophenyl)methyl]-N-(tetrahydro-2H-pyran-4-yl)pyrrolidin-3-amine,
90: (3S)-N-[(2-Chloro-6-fluorophenyl)methyl]-N-(tetrahydro-2H-pyran-4-yl)pyrrolidin-3-amine,
91: (3S)-N-{[4-Fluoro-2-(trifluoromethyl)phenyl]methyl}-N-(tetrahydro-2H-pyran-4-yl)pyrrolidin-3-amine,
92: (3S)-N-([1,1'-Biphenyl]-2-ylmethyl)-N-(tetrahydro-2H-pyran-4-yl)pyrrolidin-3-amine,
93: (3S)-N-{(4-Fluoro-[1,1'-biphenyl]-2-yl)methyl}-N-(tetrahydro-2H-pyran-4-yl)pyrrolidin-3-amine,
94: (3S)-N-[(2-Chlorophenyl)methyl]-N-(tetrahydro-2H-pyran-4-yl)pyrrolidin-3-amine,
95: (3S)-N-[(2-Chloro-5-fluorophenyl)methyl]-N-(tetrahydro-2H-pyran-4-yl)pyrrolidin-3-amine,
96: (3S)-N-[(4-Fluorophenyl)methyl]-N-(tetrahydro-2H-pyran-4-yl)pyrrolidin-3-amine,
97: (3S)-N-{[5-Fluoro-2-(trifluoromethyl)phenyl]methyl}-N-(tetrahydro-2H-pyran-4-yl)pyrrolidin-3-amine,
98: (3S)-N-(1-Methylethyl)-N-{[2-(trifluoromethyl)-5-fluorophenyl]methyl}pyrrolidin-3-amine,
99: (3S)-N-(1-Methylethyl)-N-{[3-(trifluoromethyl)phenyl]-methyl}pyrrolidin-3-amine,
100: (3S)-N-(1-Methylethyl)-N-{[4-(trifluoromethyl)phenyl]-methyl}pyrrolidin-3-amine,
101: (3S)-N-([1,1'-Biphenyl]-2-ylmethyl)-N-(1-methylethyl)-pyrrolidin-3-amine,
102: (3S)-N-(1-Methylethyl)-N-{[2-phenyloxy)phenyl]methyl}-pyrrolidin-3-amine,
103: (3S)-N-(1-Methylethyl)-N-{[2-(phenylmethyl)phenyl]-methyl}pyrrolidin-3-amine,
104: (3S)-N-[[(2,4-Dichlorophenyl)methyl]-N-(2,2,2-trifluoroethyl)amino]pyrrolidin-3-amine,
105: (3S)-N-[[(3,5-Dichlorophenyl)methyl]-N-(2,2,2-trifluoroethyl)amino]pyrrolidin-3-amine,
106: (3S)-N-[{[2-(Trifluoromethyl)phenyl]methyl}-N-(2,2,2-trifluoroethyl)amino]pyrrolidin-3-amine,
107: (3S)-N-[[(2,3-Dichlorophenyl)methyl]-N-(2,2,2-trifluoroethyl)amino]pyrrolidin-3-amine,
108: (3S)-N-[[(2-Chloro-3-methylphenyl)methyl]-N-(2,2,2-trifluoroethyl)amino]pyrrolidin-3-amine,
109: Methyl ((3S)-pyrrolidin-3-yl {[2-(trifluoromethyl)phenyl]-methyl}amino)acetate,
110: (3S)-N-[(2-Chlorophenyl)methyl]-N-(2-methylpropyl)-pyrrolidin-3-amine,
111: (3S)-N-{[2-(Methoxy)phenyl]methyl}-N-(2-methylpropyl)pyrrolidin-3-amine,
112: (3S)-N-{[2-(Ethyloxy)phenyl]methyl}-N-(2-methylpropyl)pyrrolidin-3-amine,
113: (3S)-N-[(2-Methylphenyl)methyl]-N-(2-methylpropyl)-pyrrolidin-3-amine,
114: (3S)-N-(2-Methylpropyl)-N-(phenylmethyl)pyrrolidin-3-amine,
115: (3S)-N-(2-Methylpropyl)-N-[(naphthalen-1-yl)methyl]-pyrrolidin-3-amine,
116: (3S)-N-{[4-Fluoro-2-(methoxy)phenyl]methyl}-N-(2-methylpropyl)pyrrolidin-3-amine, 117: (3S)-N-(2-Methylpropyl)-N-{[2-(phenyloxy)phenyl]methyl}-pyrrolidin-3-amine,
118: (3S)-N-{[2-Chloro-3-(trifluoromethyl)phenyl]methyl}-N-(2-methylpropyl)pyrrolidin-3-amine,
119: (3S)-N-[(2-Chloro-4-fluorophenyl)methyl]-N-(2-methylpropyl)pyrrolidin-3-amine,
120: (3S)-N-[(2,4-Dichlorophenyl)methyl]-N-(2-methylpropyl)-pyrrolidin-3amine,
121: (3R)-N-{[2-Chloro-3-(trifluoromethyl)phenyl]methyl}-N-(2-methylpropyl)pyrrolidin-3-amine,
122: (3R)-N-[(2-Chloro-3-methylphenyl)methyl]-N-(2-methylpropyl)pyrrolidin-3-amine,
123: (3R)-N-[(2-Chloro-4-fluorophenyl)methyl]-N-(2-methylpropyl)pyrrolidin-3-amine,
124: (3S)-N-{[3-Fluoro-2-(trifluoromethyl)phenyl]methyl}-N-(2-methylpropyl)pyrrolidin-3-amine,
125: (3R)-N-{[4-Fluoro-2-(trifluoromethyl)phenyl]methyl}-N-(2-methylpropyl)pyrrolidin-3-amine,
126: (3S)-N-(2-Methylpropyl)-N-{[2-(methylthio)phenyl]methyl}-pyrrolidin-3-amine,
127: (3R)-N-(2-Methylpropyl)-N-{[2-(methylthio)phenyl]methyl}-pyrrolidin-3-amine,
128: (3S)-N-[(2-Chloro-3-methylphenyl)methyl]-N-(2-methylpropyl)-pyrrolidin-3-amine,
129: (3S)-N-[(3,5-Dichlorophenyl)methyl]-N-(2-methylpropyl)-pyrrolidin-3-amine,
130: (3S)-N-[(3-Chloro-2-methylphenyl)methyl]-N-(2-methylpropyl)-pyrrolidin-3-amine,
131: (3S)-N-(3,3-Dimethylbutyl)-N-{[2-(trifluoromethyl)-phenyl]methyl}pyrrolidin-3-amine,
132: (3S)-N-(1-Methylethyl)-N-{[2-(trifluoromethyl)-phenyl]methyl}pyrrolidin-3-amine,
133: (3S)-N-(2-methylpropyl)-N-{[2-(trifluoromethyl)phenyl]-methyl}pyrrolidin-3-amine,
134: (3R)-N-(2-Methylpropyl)-N-{[2-(trifluoromethyl)phenyl]-methyl}pyrrolidin-3-amine,
135: (3S)-N-Ethyl-N-{[2-(trifluoromethyl)phenyl]methyl}-pyrrolidin-3-amine,
136: (3S)-N-Propyl-N-{[2-(trifluoromethyl)phenyl]methyl}-pyrrolidin-3-amine,
137: (3S)-N-(Cyclohexylmethyl)-N-{[2-(trifluoromethyl)-phenyl]methyl}pyrrolidin-3-amine,
138: (3S)-N-(Cyclopropylmethyl)-N-{[2-(trifluoromethyl)-phenyl]methyl}pyrrolidin-3-amine,
139: (3S)-N-(2-Phenylethyl)-N-{[2-(trifluoromethyl)phenyl]-methyl}pyrrolidin-3-amine,
140: (3S)-N-Butyl-N-{[2-(trifluoromethyl)phenyl]methyl}-pyrrolidin-3-amine,
141: (3S)-N-(2-Ethylbutyl)-N-{[2-(trifluoromethyl)phenyl]-methyl}pyrrolidin-3-amine,
142: (3S)-N-(2-Methylprop-2-enyl)-N-{[2-(trifluoromethyl)-phenyl]methyl}pyrrolidin-3-amine,
143: (3S)-N-{[2-(Trifluoromethyl)phenyl]methyl}-N-(3,3,3-trifluoropropyl)pyrrolidin-3-amine,
144: (3S)-N-(4,4,4-Trifluorobutyl)-N-{[2-(trifluoromethyl)-phenyl]methyl}pyrrolidin-3-amine,
145: (3S)-N-(Furan-2-ylmethyl)-N-{[2-(trifluoromethyl)phenyl]-methyl}pyrrolidin-3-amine,
146: (3S)-N-(3-Methylbutyl)-N-{[2-(trifluoromethyl)phenyl]-methyl}pyrrolidin-3-amine,
147: (3S)-N-[3-(Methylthio)propyl]-N-{[2-(trifluoromethyl)-phenyl]methyl}pyrrolidin-3-amine,
148: (3S)-N-(2,2-Dimethylpropyl)-N-{[2-(trifluoromethyl)-phenyl]methyl}pyrrolidin-3-amine,
149: N-(Phenylmethyl)-N-[(3S)-pyrrolidin-3-yl]-N-{[2-(trifluoromethyl)phenyl]methyl}amine,
150: (3S)-N-[(4-Fluorophenyl)methyl]-N-{[2-(trifluoromethyl)-phenyl]methyl}pyrrolidin-3-amine,
151: (3S)-N-{[2-(Ethyloxy)phenyl]methyl}-N-{[2-(trifluoromethyl)phenyl]methyl}pyrrolidin-3-amine,
152: (3S)-N-[(2-Chlorophenyl)methyl]-N-{[2-(trifluoromethyl)-phenyl]methyl}pyrrolidin-3-amine,
153: (3S)-N-[(2-Fluorophenyl)methyl]-N-{[2-(trifluoromethyl)-phenyl]methyl}pyrrolidin-3-amine,
154: (3S)-N-{[2-(Methyloxy)phenyl]methyl}-N-{[2-(trifluoromethyl)phenyl]methyl}pyrrolidin-3-amine,
155: (3S)-N,N-bis {[2-(Trifluoromethyl)phenyl]methyl}-pyrrolidin-3-amine,
156: (3S)-N-(2-Ethylbutyl)-N-{[2-(trifluoromethyl)-phenyl]methyl}pyrrolidin-3-amine,
157: (3S)-N-{[2-(Trifluoromethyl)phenyl]methyl}-N-(3,3,3-trifluoropropyl)pyrrolidin-3-amine,
158: (3S)-N-(4,4,4-Trifluorobutyl)-N-{[2-(trifluoromethyl)-phenyl]methyl}pyrrolidin-3-amine,
159: (3S)-N-Ethyl-N-{[2-(trifluoromethyl)-phenyl]methyl}-pyrrolidin-3-amine,
160: (3S)-N,N-bis-[(2-Chloro-4-fluorophenyl)methyl]-pyrrolidin-3-amine,
161: (3S)-N,N-bis-[(2,4-Dichlorophenyl)methyl]-pyrrolidin-3-amine,
162: 1-{[(3,5-Dichlorophenyl)methyl][(3S)-pyrrolidin-3-yl]amino}-2-methylpropan-2-ol,
163: 1-{[(2,4-Dichlorophenyl)methyl][(3S)-pyrrolidin-3-yl]amino}-2-methylpropan-2-ol,
164: 1-{{[4-Fluoro-2-(trifluoromethyl)phenyl]methyl}[(3S)-pyrrolidin-3-yl]amino}-2-methylpropan-2-ol,
165: 1-{[(2-Chloro-4-fluorophenyl)methyl][(3S)-pyrrolidin-3-yl]amino}-2-methylpropan-2-ol,
166: 1-{[(2-Chloro-6-fluorophenyl)methyl][(3S)-pyrrolidin-3-yl]amino}-2-methylpropan-2-ol,
167: 1-{[(2-Phenyl-5-fluorophenyl)methyl][(3S)-pyrrolidin-3-yl]amino}-2-methylpropan-2-ol,
168: 1-{{[2-(Trifluoromethyl)phenyl]methyl}[(3S)-pyrrolidin-3-yl]amino}-2-methylpropan-2-ol,
169: N-(2-Methylpropyl)-N-(4-methylbenzyl)-pyrrolidin-3-amine,
170: N-(2-Methylpropyl)-N-(4-chlorobenzyl)-pyrrolidin-3-amine,
171: N-(2-Methylpropyl)-N-(4-methoxybenzyl)-pyrrolidin-3-amine,
172: N-(2-Methylpropyl)-N-(3,4-dichlorobenzyl)-pyrrolidin-3-amine,
173: N-(2-Methylpropyl)-N-(2-trifluoromethylbenzyl)-pyrrolidin-3-amine,
174: N-Cyclohexylmethyl-N-benzyl-pyrrolidin-3-amine,
175: N-Cyclohexylmethyl-N-(4-methoxybenzyl)-pyrrolidin-3-amine,
176: N-Cyclohexylmethyl-N-(4-methylbenzyl)-pyrrolidin-3-amine,
177: N-Cyclohexylmethyl-N-(3,4-dichlorobenzyl)-pyrrolidin-3-amine,
178: N-Cyclopropylmethyl-N-(4-chlorobenzyl)-pyrrolidin-3-amine,
179: N-Cyclopropylmethyl-N-(4-methoxybenzyl)-pyrrolidin-3-amine,
180: N-Cyclopropylmethyl-N-(3,4-dichlorobenzyl)-pyrrolidin-3-amine,
181: N-Cyclopropylmethyl-N-(2-trifluoromethylbenzyl)-pyrrolidin-3-amine,
182: N-Butyl-N-benzyl,-pyrrolidin-3-amine,
183: N-Butyl-N-(4-chlorobenzyl)-pyrrolidin-3-amine,
184: N-Butyl-N-(4-methoxybenzyl)-pyrrolidin-3-amine,
185: N-Butyl-N-(4-methylbenzyl)-pyrrolidin-3-amine, 186: N-Butyl-N-(3,4-dichlorobenzyl)-pyrrolidin-3-amine,
187: N-Butyl-N-(2-trifluoromethylbenzyl)-pyrrolidin-3-amine,
188: (3S)-N-[(3R)-Tetrahydrofuran-3-yl]-N-{[2-(trifluoromethyl)phenyl]methyl}pyrrolidin-3-amine,
189: (3S)-N-[(3S)-Tetrahydrofuran-3-yl]-N-{[2-(trifluoromethyl)phenyl]methyl}pyrrolidin-3-amine,
190: (3S)-N-([1,1'-Biphenyl]-2-ylmethyl)-N-[(3R)-tetrahydrofuran-3-yl]pyrrolidin-3-amine,
191: (3S)-N-([1,1'-Biphenyl]-2-ylmethyl)-N-[(3S)-tetrahydrofuran-3-yl]pyrrolidin-3-amine,
192: (3S)-N-[(2-Chloro-6-fluorophenyl)methyl]-N-[(3R)-tetrahydrofuran-3-yl]pyrrolidin-3-amine,
193: (3S)-N-[(2-Chloro-6-fluorophenyl)methyl]-N-[(3S)-tetrahydrofuran-3-yl]pyrrolidin-3-amine,
194: (3S)-N-[(Tetrahydrofuran-3-yl)methyl]-N-{[2-(trifluoromethyl)phenyl]methyl}pyrrolidin-3-amine,
195: (3S)-N-(2-Methylpropyl)-N-{[3-phenylpyrid-2-yl]methyl}-pyrrolidin-3-amine,
196: (3S)-N-(Cyclohexyl)-N-{[2-(3-phenyl)pyridyl]methyl}-pyrrolidin-3-amine,
197: (3S)-N-(2-Methylpropyl)-N-{[2-(3-pyridyl)-phenyl]methyl}pyrrolidin-3-amine,
198: (3S)-N-(2-Methylpropyl)-N-{[2-(1-pyrazolyl)phenyl]methyl}pyrrolidine-3-amine,
199: (3S)-N-Propyl-N-{[2-(trifluoromethyl)phenyl]methyl}-pyrrolidin-3-amine,
200: (3S)-N-{5-fluoro-2-(trifluoromethyl)phenyl]methyl}-N-propylpyrrolidin-3-amine,
201: (3S)-N-Pyridin-3-ylmethyl)-N-{[2-(trifluoromethyl)phenyl]methyl}pyrrolidin-3-amine,
202: (3S)-N-[(4-Fluoro[1,1'-biphenyl]-2-methyl]-N-(pyridin-2-ylmethyl) pyrrolidin-3-amine,
203: (3S)-N-[(4-Fluoro[1,1'-biphenyl]-2-methyl]-N-(pyridin-3-ylmethyl) pyrrolidin-3-amine,
204: (3S)-N-[(2-Chloro-6-fluorophenyl)methyl]-N-(pyridin-2-ylmethyl)pyrrolidine-3-amine,
205: (3S)-N-[(2-Chloro-6-fluorophenyl)methyl]-N-(pyridin-4-ylmethyl)pyrrolidine-3-amine,
206: (3S)-N-[(2-Chloro-6-fluorophenyl)methyl]-N-(pyridin-3-ylmethyl)pyrrolidine-3-amine, and
207: (3S)-N-(Pyridin-2-ylmethyl)-N-{[2-(trifluoromethyl)phenyl]methyl}pyrrolidin-3-amine.

The present invention includes pharmaceutically acceptable salts of the compounds of formula (I). Suitable salts include acid addition salts, including salts formed with inorganic acids (for example hydrochloric, hydrobromic, nitric, sulphuric or phosphoric acid) or with organic acids, such as organic carboxylic acids (for example acetic, fumaric, pyruvic, lactobionic, glycolic, oxalic, maleic, hydroxymaleic, malic, citric, salicylic, o-acetoxybenzoic or tartaric acid), or organic sulphonic acids (for example toluene-p-sulphonic, naphthalenesulfonic, bisethanesulphonic or methanesulphonic acid). Particularly preferred are salts formed with phosphoric, fumaric, L-tartaric, D-tartaric or naphthalenesulfonic acid. Most preferred are salts formed with L-tartaric or D-tartaric acid.

It will be appreciated that certain compounds of formula (I) may possess one or more chiral centres. Where a structural formula does not specify the stereochemistry at one or more chiral centres, it encompasses all possible stereoisomers and all possible mixtures of stereoisomers (including, but not limited to, racemic mixtures), which may result from stereoisomerism at each of the one or more chiral centers. For example, the carbon atom at the three position of the pyrrolidine ring can give rise to two enantiomers of formulae (Ia) and (Ib):

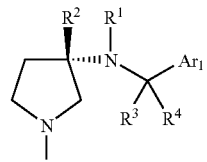

(Ia)

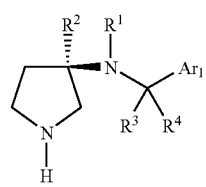

(Ib)

wherein $R^1$, $R^2$, $R^3$, $R^4$ and $Ar_1$ have the values defined in formula (I) above, with the proviso's therein. Said isomers are also an aspect of the present invention. Preferred compounds of the invention are those of formula (Ia).

As mentioned above, the compounds of the present invention and their pharmaceutically acceptable salts inhibit the uptake of one or more of the monoamine neurotransmitters serotonin, dopamine and norepinephrine. In view of these properties, the compounds of the present invention and their pharmaceutically acceptable salts are indicated for use in treating disorders which are caused by or linked to decreased neurotransmission of one or more of these monoamines. Such disorders include disorders of the central and/or peripheral nervous system.

One preferred group of compounds of the present invention selectively inhibit the reuptake of serotonin and norepinephrine over dopamine. Preferably said group of compounds of the present invention selectively inhibit the serotonin and norepinephrine transporters relative to the dopamine transporter by a factor of at least five, and even more preferably by a factor of at least ten. Compounds of the present invention with this pharmacological profile are particularly useful for the treatment of depression, eating disorders (including bulimia and anorexia nervosa), inflammatory bowel disorders, functional bowel disorders, dyspepsia, Crohn's disease, iletis, ischemic bowel disease, ulcerative colitis, gastroesophageal reflux for functional bowel disorders, irritable bowel syndrome, obesity, insterstitial cystitis, urethral syndrome, gastric motility disorders, substance abuse (including alcoholism, tobacco abuse, symptoms caused by withdrawal or partial withdrawal from the use of tobacco or nicotine and drug addiction including cocaine abuse), pain (including inflammatory pain, neuropathic pain, non-neuropathic non-inflammatory pain, persistent pain, persistent pain of inflammatory and/or neuropathic origin, headache and migraine), incontinence (including stress urinary incontinence and urge incontinence), dementia of ageing, senile dementia, Alzheimer's, memory loss, Parkinsonism, attention-deficit disorder (including attention-deficit hyperactivity disorder), anxiety, social phobia, disruptive behavior disorders, impulsive control disorders, borderline personality disorder, chronic fatigue syndrome, panic disorders, obsessive compulsive disorder, post-trainiatic stress disorder, schizophrenia, gastrointestinal disorders, cardiovascular disorders, hot flushes/flashes emesis, sleep disorders, cognitive disorders, psychotic disorders, brain trauma, premenstrual syndrome or late luteal syndrome, sexual dysfunction (including premature ejaculation and erectile difficulty), autism, mutism and trichotilomania. They are more particularly useful for the treatment of depression, incontinence (particularly stress urinary incontinence) and pain (particularly persistent pain). They are most particularly useful for the treatment of persistent pain.

For clinical purposes, pain may be divided into two categories: acute pain and persistent pain. Acute pain is provoked by noxious stimulation produced by injury and/or disease of skin, deep somatic structures or viscera, or abnormal function of muscle or viscera that does not produce actual tissue damage. On the other hand, persistent pain can be defined as pain that persists beyond the usual course of an acute disease or a reasonable time for an injury to heal or that is associated with a chronic pathologic process that causes continuous pain or the pain recurs at intervals for months or years. If pain is still present after a cure should have been achieved, it is considered persistent pain. For the purpose of the present invention, persistent pain can be chronic non-remitting or recurrent. The difference in definition between acute and persistent pain is not merely semantic but has an important clinical relevance. For example, a simple fracture of the wrist usually remains painful for a week to 10 days. If the pain is still present beyond the typical course of treatment, it is likely that the patient is developing reflex sympathetic dystrophy, a persistent pain syndrome that requires immediate effective therapy. Early and effective intervention potentially prevents the undue disability and suffering, and avoids the potential development of a condition that becomes refractory to therapy.

Acute and persistent pain differ in etiology, mechanisms, pathophysiology, symptomatology, diagnosis, therapy, and physiological responses. In contrast to the transitory nature of acute pain, persistent pain is caused by chronic pathologic processes in somatic structures or viscera, by prolonged and sometimes permanent dysfunction of the peripheral or central nervous system, or both. Also, persistent pain can sometimes be attributed to psychologic mechanisms and/or environmental factors.

More specifically, persistent pain can be segmented into neuropathic pain (e.g. diabetic neuropathy, infectious neuropathic pain associated with AIDS, non-surgical carpal tunnel syndromes, post-herpetic neuralgia, cervical, thoracic and lumbosacral radiculopathies, stroke-related central pains, trigeminal neuralgia and complex regional pain syndromes I and II), inflammatory pain (e.g. polymyalgia, rheumatoid arthritis and osteoarthritis), non-neuropathic non-inflammatory pain, and non-neuropathic non-inflammatory chronic pain (NNNICP) (e.g. chronic fatigue syndrome, chronic back pain without radiculopathy, fibromyalgia, chronic tension type headaches, inflammatory bowel disorders, irritable bowel syndrome, whiplash injuries, chronic pelvic pain, temporomandibular joint disorder (TMJD) and failed back).

Current therapies for persistent pain include opiates, barbiturate-like drugs such as thiopental sodium and surgical procedures such as neurectomy, rhizotomy, cordotomy, and cordectomy.

Another preferred group of compounds of the present invention selectively inhibit the reuptake of norepinephrine over serotonin and dopamine. Preferably said group of compounds of the present invention selectively inhibit the norepinephrine transporter relative to the serotonin and dopamine transporters by a factor of at least five, and even more preferably by a factor of at least ten. Compounds of the present invention with this pharmacological profile are particularly useful for the treatment of addictive disorder and withdrawal syndrome, an adjustment disorder (including depressed mood, anxiety, mixed anxiety and depressed mood, disturbance of conduct, and mixed disturbance of conduct and mood), an age-associated learning and mental disorder (including Alzheimer's disease), alcohol addiction, anorexia nervosa, apathy, an attention-deficit disorder (ADD) due to general medical conditions, attention-deficit hyperactivity disorder (ADHD) including the predominantly inattentive type of ADHD and the predominantly hyperactive-impulsive type of ADHD, bipolar disorder, bulimia nervosa, chronic fatigue syndrome, chronic or acute stress, cognitive disorders (discussed in more detail below but including mild cognitive impairment (MCI) and cognitive impairment associated with schizophrenia (CIAS)), communication disorders (including stuttering, expressive language disorder, mixed receptive-expressive language disorder, phonological disorder and communication disorder not otherwise specified), conduct disorder, cyclothymic disorder, dementia of the Alzheimers type (DAT), depression (including adolescent depression and minor depression), dysthymic disorder, emotional dysregulation (including emotional dysregulation associated with ADHD, borderline personality disorder, bipolar disorder, schizophrenia, schizoaffective disorder and intermittent explosive disorder), fibromyalgia and other somatoform disorders (including somatization disorder, conversion disorder, pain disorder, hypochondriasis, body dysmorphic disorder, undifferentiated somatoform disorder, and somatoform NOS), generalized anxiety disorder (GAD), hot flashes or vasomotor symptoms, hypotensive states including orthostatic hypotension, impulse control disorders (including intermittent explosive disorder, kleptomania, pyromania, pathological gambling, trichotillomania and impulse-control disorder not otherwise specified), incontinence (i.e., stress incontinence, genuine stress incontinence, and mixed incontinence), an inhalation disorder, an intoxication disorder, learning disabilities (including developmental speech and language disorders (such as developmental articulation disorder, developmental expressive language disorder and developmental receptive language disorder), learning disorders (such as reading disorder, mathematics disorder, disorder of written expression and learning disorder not otherwise specified) and motor skills disorders (such as developmental coordination disorder)), mania, migraine headaches, nicotine addiction, obesity (i. e., reducing the weight of obese or overweight patients), obsessive compulsive disorders and related spectrum disorders, oppositional defiant disorder, pain including chronic pain, neuropathic pain and antinociceptive pain, panic disorder, peripheral neuropathy, post-traumatic stress disorder, personality change due to a general medical condition (including labile type, disinhibited type, aggressive type, apathetic type, paranoid type, combined type and unspecified type), pervasive developmental disorders (including autistic disorder, Asperger's disorder, Rett's disorder, childhood disintegrative disorder, and pervasive developmental disorder not otherwise specified), premenstrual dysphoric disorder (i.e., premenstrual syndrome and late luteal phase dysphoric disorder), psoriasis, a psychoactive substance use disorder, a psychotic disorder (including schizophrenia, schizoaffective and schizophreniform disorders), seasonal affective disorder, selective serotonin reuptake inhibition (SSRI) "poop out" syndrome (i.e., wherein a patient who fails to maintain a satisfactory response to SSRI therapy after an initial period of satisfactory response), a sleep disorder (such as narcolepsy and enuresis), social phobia (including social anxiety disorder), a specific developmental disorder, TIC disorders (e.g., Tourette's Disease), tobacco addiction and vascular dementia. They are most particularly useful for the treatment of ADHD and schizophrenia.

The term "cognitive disorders" (also variously referred to as "cognitive failure," "cognitive insufficiency," "cognitive deficit," "cognitive impairment," "cognitive dysfunction," and the like) refers to the dysfunction, diminution, or loss of one or more cognitive functions, the processes by which knowledge is acquired, retained, and used. Cognitive dysfunction includes cognitive changes associated with ageing ("age-associated memory impairment"), as well as changes due to other causes. Cognitive impairment is most commonly due to a delirium or dementia, but can also occur in association with a number of other medical or neuropsychiatric disorders. More focal cognitive deficits are diagnosed using the criteria disclosed in the *Diagnostic and Statistical Manual of Mental Disorders*, Fourth Edition, Text Revision (DSM-IV-TR™, 2000), American Psychiatric Association, Washington, D.C., as either amnestic disorders (affecting memory) or cognitive disorder not otherwise specified (NOS), which includes executive dysfunction, visuospatial/visuocontructional impairment, attentional deficits, disorientation, etc. These more focal cognitive disorders also have a wide variety of causes, some of which are of unknown etiology.

A delerium is characterized by a disturbance of consciousness with a reduced ability to focus, sustain, or shift attention and a change in cognition that develops over a short period of time. Delirium is very common, and occurs on average in about a fifth of general hospital inpatients, and is even more common in nursing home patients and those with terminal illnesses. The disorders included in the "Delirium" section of the DSM-IV-TR™ are listed according to presumed etiology: Delirium Due to a General Medical Condition, Substance-Induced Delirium (i.e., due to a drug of abuse, a medication, or toxin exposure), Delirium Due to Multiple Etiologies, or Delirium Not Otherwise Specified (if the etiology is indeterminate). As disclosed by Wise et al. ((2002) Delirium (Confusional States), In Wise and Rundell, Eds., *The American Psychiatric Publishing Textbook of Consultation-Liaison Psychiatry, Psychiatry in the Medically Ill*, Second Edition, American Psychiatric Publishing, Inc., Washington, D.C., Chapter 15, pp. 257-272, Table 15-4), exemplary etiological bases of delirium include, but are not limited to, infection, withdrawal from alcohol and drugs, acute metabolic conditions, trauma of various types, CNS pathologies, hypoxia, vitamin deficiencies, endocrinopathies, acute vascular conditions, toxins or drugs, and heavy metals.

A dementia is a chronic condition, usually with a more gradual deterioration of memory and other intellectual functioning and other cognitive skills severe enough to interfere with the ability to perform activities of daily living. Although dementia may occur at any age, it primarily affects the elderly, presenting in more than 15% of persons over 65 years of age and in as many as 40% of persons over 80 years old. Dementia due to Alzheimer's disease is particularly common. Non-Alzheimer's cognitive impairments and/or dementias include, for example, those caused by or associated with: vascular diseases; Parkinson's disease; Lewy body disease (diffuse Lewy body disease); HIV/AIDS; mild cognitive impairments; mild nuerocognitive disorders; age-associated memory impairments; neurologic and/or psychiatric conditions including epilepsy and epilepsy treatments; brain tumors, cysts, lesions, or other inflammatory brain diseases; multiple sclerosis; Down's syndrome; Rett's syndrome; progressive supranuclear palsy; frontal lobe dementia syndromes; schizophrenia and related psychiatric disorders; antipsychotic medications; traumatic brain injury (closed head injury), dementia pugilistica, and other head traumas; normal-pressure hydrocephalus; surgery (including coronary artery by-pass graft surgery) and anaesthesia, electroconvulsive shock therapy, and cancer and cancer therapies.

The dementias are also listed in the "Dementia" section of the DSM-IV-TR™ according to presumed etiology: Dementia of the Alzheimer's Type, Vascular Dementia, Dementia Due to Other General Medical Conditions (e.g., human immunodeficiency virus [HIV] disease, head trauma, Parkinson's disease, Huntington's disease), Substance-Induced Persisting Dementia (i.e., due to a drug of abuse, a medication, or toxin exposure), Dementia Due to Multiple Etiologies, or Dementia Not Otherwise Specified (if the etiology is indeterminate). As disclosed by Gray and Cummings ((2002) Dementia, In Wise and Rundell, Eds., *The American Psychiatric Publishing Textbook of Consultation-Liaison Psychiatry, Psychiatry in the Medically Ill*, Second Edition, American Psychiatric Publishing, Inc., Washington, D.C., Chapter 16, pp. 273-306, Table 16-1), exemplary etiological bases of principal dementia syndromes include, but are not limited to, degenerative disorders (cortical and subcortical), vascular disorders, myelinoclastic disorders, traumatic conditions, neoplastic disorders, hydrocephalic disorders, inflammatory conditions, infections, toxic conditions, metabolic disorders, and psychiatric disorders.

An amnestic disorder is characterized by memory impairment in the absence of other significant accompanying cognitive impairments. The disorders in the "Amnestic Disorders" section of the DSM-IV-TR™ are also listed according to presumed etiology: Amnestic Disorder Due to a General Medical Condition, Substance-Induced Persisting Amnestic Disorder, or Amnestic Disorder Not Otherwise Specified.

Cognitive Disorder Not Otherwise Specified in the DSM-IV-TR™ covers presentations that are characterized by cognitive dysfunction presumed to be due to either a general medical condition or substance use that do not meet criteria for any of the disorders listed elsewhere in the section of the DSM-IV-TR™ entitled "Delirium, Dementia, and Amnestic and Other Cognitive Disorders."

Dementia, amnestic disorders, and cognitive disorders NOS occur in patients with a wide variety of other disorders including, but not limited to, Huntington's disease (chorea); Pick's disease; spinocerebellar ataxias (types 1-1); corticobasalganglionic degeneration; neuroacanthocytosis; dentatorubropallidoluysian atropy (DRPLA); systemic lupus erythematosus; heavy metal intoxication; alcoholic dementia (Wernicke's encephalopathy); fetal alcohol syndrome; single or multiples strokes, including small vessels (Binswanger's dementia: subcortical arteriosclerotic encephalopathy) and large vessels (multi-infarct dementia); anoxic encephalopathy; tumors; birth anoxia; premature birth; inborn errors of metabolism; neurofibromatosis (Type I); tuberous sclerosis; Hallervorden Spatz disease; Wilson's disease; post-infectious sequelae (e.g., tuberculosis, viral encephalitis, bacterial meningitis); subdural hematoma; subcortical dementia; Creutzfeldt-Jakob disease; Gerstmann-Sträussler-Scheinker disease; general paresis; and syphilis.

As discussed in detail above, cognitive failure may present in patients suffering from a number of disorders, including dementia or delirium, or due to a wide variety of other causes. The compounds of the present invention are useful for the treatment or prevention of cognitive failure associated with, or due to, the disorders or etiologies discussed above, including disorders formally classified in the DSM-IV-TR™. For the convenience of the reader, the DSM-IV-TR™ code numbers or descriptions are supplied below. "ICD-9-CM codes" refers to codes for, e.g., selected general medical conditions and medication-induced disorders contained in the *International Classification of Diseases*, $9^h$ Revision, Clinical Modification.

| | |
|---|---|
| Delirium Due to a General Medical Condition | 293.0 |
| Substance-Induced Delirium, including: | |
| Substance Intoxication Delirium: | |
| Code [Specific Substance] Intoxication Delirium: | |
| (291.0 Alcohol; 292.81 Amphetamine [or Amphetamine-Like Substance]; 292.81 | |
| Cannabis; 292.81 Cocaine; 292.81 Hallucinogen; 292.81 Inhalant; 292.81 Opioid; | |
| 292.81 Phencyclidine [or Phencyclidine-Like Substance]; 292.81 Sedative, | |
| Hypnotic, or Anxiolytic; 292.81 Other [or Unknown] Substance [e.g., cimetidine, | |
| digitalis, benztropine]) | |
| Substance Withdrawal Delirium: | |
| Code [Specific Substance] Withdrawal Delirium: | |
| (291.0 Alcohol; 292.81 Sedative, Hypnotic, or Anxiolytic; 292.81 Other [or | |
| Unknown] Substance) | |
| Delirium Due to Multiple Etiologies: | |
| Multiple codes are used, reflecting the specific delirium and specific etiologies, | |
| e.g., 293.0 Delirium Due to Viral Encephalitis; 291.0 Alcohol Withdrawal Delirium | |
| Delirium Not Otherwise Specified | 780.09 |
| Dementia of the Alzheimer's Type | 294.1x* (*ICD-9-CM code) |
| Subtypes: | |
| With Early Onset (onset of the dementia is age 65 years or under) | |
| With Late Onset (onset of the dementia is after age 65 years) | |
| Without Behavioral Disturbance | 294.10 |
| With Behavorial Disturbance | 294.11 |
| Vascular Dementia | 290.4x |
| Subtypes: | |
| With Delirium | 290.41 |
| With Delusions | 290.42 |
| With Depressed Mood | 290.43 |
| With Behavioral Disturbance | Uncoded |
| Uncomplicated | 290.40 |
| Dementia Due to HIV Disease | 294.1x* (*ICD-9-CM code) |
| Dementia Due to Head Trauma | 294.1x* (*ICD-9-CM code) |
| Dementia Due to Parkinson's Disease | 294.1x* (*ICD-9-CM code) |
| Dementia Due to Huntington's Disease | 294.1x* (*ICD-9-CM code) |
| Dementia Due to Pick's Disease | 290.1x* (*ICD-9-CM code) |
| Dementia Due to Creutzfeldt-Jakob Disease | 290.1x* (*ICD-9-CM code) |
| Dementia Due to Other General Medical Conditions | 294.1x* (*ICD-9-CM code) |
| Code based on presence or absence of a clinically | |
| significant behavioral disturbance: | |
| Without Behavioral Disturbance | 294.10 |
| With Behavioral Disturbance | 294.11 |
| Substance-Induced Persisting Dementia | |
| Code [Specific Substance]-Induced Persisting Dementia: | |
| (291.2 Alcohol; 292.82 Inhalant; 292.82 Sedative, Hypnotic, or Anxiolytic; | |
| 292.82 Other [or Unknown] Substance) | |
| Dementia Due to Multiple Etiologies | |
| Coding note: Use multiple codes based on specific dementias and specific | |
| etiologies, e.g., 294.10 Dementia of the Alzheimer's Type, With Late Onset, | |
| Without Behavioral Disturbance; 290.40 Vascular Dementia, Uncomplicated. | |
| Dementia Not Otherwise Specified | 294.8 |
| Amnestic Disorder Due to a General Medical Condition | 294.0 |
| Transient or Chronic | |
| Substance-Induced Persisting Amnestic Disorder | |
| Code [Specific Substance]-Induced Persisting Amnestic Disorder: | |
| 291.1 Alcohol; 292.83 Sedative, Hypnotic, or Anxiolytic; 292.83 Other [or | |
| Unknown] Substance | |
| Amnestic Disorder Not Otherwise Specified | 294.8 |
| Cognitive Disorder Not Otherwise Specified | 294.9 |
| Age-Related Cognitive Decline | 780.9 |

Examples of cognitive disorders due to various etiologies, or associated with various disorders, of particular interest that can be prevented or treated using the compounds of the present invention include: enhancing cognitive functions and executive functioning (ability to plan, initiate, organize, carry out, monitor, and correct one's own behavior) in normal subjects or in subjects exhibiting cognitive dysfunction; treatment of cognitive and attentional deficits associated with prenatal exposure to substances of abuse including, but not limited to, nicotine, alcohol, methamphetamine, cocaine, and heroin; treatment of cognitive impairment caused by chronic alcohol and drug abuse (substance-induced persisting dementia), medicament side effects, and treatment of drug craving and withdrawal; treatment of cognitive deficits in Down's Syndrome patients; treatment of deficits in normal memory functioning comorbid with major depressive and bipolar disorders; treatment of cognitive impairment associated with depression, mental retardation, bipolar disorder, or schizophrenia; treatment of dementia syndromes associated with mania, conversion disorder, and malingering; treatment of problems of attention, prefrontal executive function, or memory due to head trauma or stroke; treatment of cognitive dysfunction in menopausal and post-menopausal women and in women undergoing hormone replacement therapy; treatment of cognitive deficits and fatigue due to, or associated with, cancer and cancer therapies (cognitive deficits are associated with a variety of cancer treatments, including cranial radiation, conventional (standard-dose) chemotherapy, high-dose chemotherapy and hematopoietic (bone-marrow) transplantation, and biologic agents).

Compounds which selectively inhibit the reuptake of norepinephrine over serotonin and dopamine are also useful in a method for treating a patient suffering from or susceptible to psychosis, comprising administering to said patient an effective amount of a first component which is an antipsychotic, in combination with an effective amount of a second component which is a compound of formula (I) that selectively inhibits the reuptake of norepinephrine over serotonin and dopamine. The invention also provides a pharmaceutical composition which comprises a first component that is an antipsychotic, and a second component that is a compound of formula (I) that selectively inhibits the reuptake of norepinephrine over serotonin and dopamine. In the general expressions of this aspect of the present invention, the first component is a compound that acts as an antipsychotic. The antipsychotic may be either a typical antipsychotic or an atypical antipsychotic. Although both typical and atypical antipsychotics are useful for these methods and formulations of the present invention, it is preferred that the first component compound is an atypical antipsychotic.

Typical antipsychotics include, but are not limited to: Chlorpromazine, 2-chloro-10-(3-dimethylaminoprop-yl) phenothiazine, is described in U.S. Pat. No. 2,645,640. Its pharmacology has been reviewed (Crismon, *Psychopharmacol. Bul.*, 4, 151 (October 1967); Droperidol, 1-(1-[3-(p-fluorobenzoyl)propyl]-1,2,3,6-tetrahydro-4-pyridyl)-2-benzimidazolinone, is described in U.S. Pat. No. 3,141,823; Haloperidol, 4-[4-(4-chlorophenyl)-4-hydroxy-1-piperidinyl]-1-(4-fluorophenyl)-1-butanone, is described in U.S. Pat. No. 3,438,991. Its therapeutic efficacy in psychosis has been reported (Beresford and Ward, *Drugs*, 33, 31-49 (1987); Thioridazine, 1-hydroxy-10-[2-(1-methyl-2-pyridinyl) ethyl]-2-(methylthio)phenothiazine hydrochloride, was described by Bourquin, et al. (*Helv. Chim. Acta,* 41, 1072 (1958)). Its use as an antipsychotic has been reported (Axelsson, et al., *Curr. Ther. Res.*, 21, 587 (1977)); and Trifluoperazine, 10-[3-(4-methyl-1-piperazinyl)-propyl]-2-trifluoromethylphenthiazine hydrochloride, is described in U.S. Pat. No. 2,921,069.

Atypical antipsychotics include, but are not limited to: Olanzapine, 2-methyl-4-(4-methyl-1-piperazinyl)-10H-thieno[2,3-b][1,5]benzodiazepine, is a known compound and is described in U. S. Pat. No. 5,229,382 as being useful for the treatment of schizophrenia, schizophreniform disorder, acute mania, mild anxiety states, and psychosis; Clozapine, 8-chloro-11-(4-methyl-1-piperazinyl)-5H-dibenzo[b,e][1,4] diazepine, is described in U.S. Pat. No. 3,539,573. Clinical efficacy in the treatment of schizophrenia is described (Hanes, et al., *Psychopharmacol. Bull.*, 24, 62 (1988)); Risperidone, 3-[2-[4-(6-fluoro-1,2-benzisoxazol-3-yl)piperidino]ethyl]-2-methyl-6,7,8,9-tetrahydro-4H-pyrido[1,2-a] pyrimidin-4-one, and its use in the treatment of psychotic diseases are described in U.S. Pat. No. 4,804,663; Sertindole, 1-[2-[4-[5-chloro-1-(4-fluorophenyl)-1H-indol-3-yl]-1-piperidinyl]ethyl]imidazolidin-2-one, is described in U.S. Pat. No. 4,710,500. Its use in the treatment of schizophrenia is described in U.S. Pat. Nos. 5,112,838 and 5,238,945; Quetiapine, 5-[2-(4-dibenzo[b,f][1,4]thiazepin-11-yl-1-piperazinyl)ethoxy]ethanol, and its activity in assays which demonstrate utility in the treatment of schizophrenia are described in U.S. Pat. No. 4,879,288. Quetiapine is typically administered as its (E)-2-butenedioate (2:1) salt; Ziprasidone, 5-[2-[4-(1, 2-benzoisothiazol-3-yl)-1-piperazinyl]ethyl]-6-chloro-1,3-dihydro-2H-indol-2-one, is typically administered as the hydrochloride monohydrate. The compound is described in U.S. Pat. Nos. 4,831,031 and 5,312,925. Its activity in assays which demonstrate utility in the treatment of schizophrenia are described in U.S. Pat. No. 4,831,031; and Aripiprazole (Abilify™), 7-[4-[4-(2,3-dichlorophenyl)-1-piperazinyl]butoxy]-3,4-dihydrocarbostyril (U.S. Pat. Nos. 4,734,416 and 5,006,528) is a new antipsychotic indicated for the treatment of schizophrenia.

It will be understood that while the use of a single antipsychotic as a first component compound is preferred, combinations of two or more antipsychotics may be used as a first component if necessary or desired. Similarly, while the use of a single compound of formula (I) as a second component compound is preferred, combinations of two or more compounds of formula (I) may be used as a second component if necessary or desired.

While all combinations of first and second component compounds are useful and valuable, certain combinations are particularly valued and are preferred, as follows:

olanzapine/compound of formula (I)
clozapine/compound of formula (I)
risperidone/compound of formula (I)
sertindole/compound of formula (I)
quetiapine/compound of formula (I)
ziprasidone/compound of formula (I)
aripiprazole/compound of formula (I)

In general, combinations and methods of treatment using olanzapine as the first component are preferred. It is especially preferred that when the first component is. olanzapine, it will be the Form II olanzapine as described in U.S. Pat. No. 5,736,541. It is further preferred that the Form II olanzapine polymorph will be administered as the substantially pure Form II olanzapine polymorph. As used herein "substantially pure" refers to Form II associated with less than about 5% Form I, preferably less than about 2% Form I, and more preferably less than about 1% Form I. Further, "substantially pure" Form II will contain less than about 0.5% related substances, wherein "related substances" refers to undesired chemical impurities or residual solvent or water. In particular, "substantially pure" Form II should contain less than about 0.05% content of acetonitrile, more preferably, less than about 0.005% content of acetonitrile. Additionally, the polymorph of the invention should contain less than 0.5% of associated water. Although Form II olanzapine is preferred it will be understood that as used herein, the term "olanzapine" embraces all solvate and polymorphic forms unless specifically indicated.

Conditions that can be treated by the adjunctive therapy aspect of the present invention include schizophrenia, schizophreniform diseases, bipolar disorder, acute mania, and schizoaffective disorders. The titles given these conditions represent multiple disease states. The following list illustrates a number of these disease states, many of which are classified in the DSM-IV-TR™. The DSM-IV-TR™ code numbers for these disease states are supplied below, when available, for the convenience of the reader.

| | |
|---|---|
| Paranoid Type Schizophrenia | 295.30 |
| Disorganized Type Schizophrenia | 295.10 |

| | |
|---|---|
| Catatonic Type Schizophrenia | 295.20 |
| Undifferentiated Type Schizophrenia | 295.90 |
| Residual Type Schizophrenia | 295.60 |
| Schizophreniform Disorder | 295.40 |
| Schizoaffective Disorder | 295.70 |

The present invention also encompasses the use of one or more compounds of formula (I) that selectively inhibit the reuptake of norepinephrine over serotonin and dopamine in combination with one or more conventional Alzheimer's agents for the prevention or treatment of cognitive dysfunction in patients suffering from Alzheimer's disease. The invention also provides a pharmaceutical composition which comprises a first component that is a conventional Alzheimer's agent and a second component that is a compound of formula (I) that selectively inhibits the reuptake of norepinephrine over serotonin and dopamine. Conventional Alzheimer's agents include inhibitors of acetylcholine degradation (i.e., cholinesterase or acetylcholinesterase inhibitors) within synapses, e.g., donepezil (Aricept®), rivastigmine (Exelon®), galantamine (Reminyl®), and tacrine (Cognex®); the selective monoamine oxidase inhibitor selegiline (Eldepryl®); and memantine (Namenda™), a newly FDA-approved NMDA receptor antagonist for the treatment of moderate to severe Alzheimer's disease. Modafinil (Provigil®) is also used in the treatment of Alzheimer's disease.

The present invention also encompasses the use of one or more compounds of formula (I) that selectively inhibit the reuptake of norepinephrine over serotonin and dopamine in combination with one or more conventional Parkinson's agents for the treatment of cognitive dysfunction in Parkinson's disease. The invention also provides a pharmaceutical composition which comprises a first component that is a conventional Parkinson's agent and a second component that is a compound of formula (I) that selectively inhibits the reuptake of norepinephrine over serotonin and dopamine. Conventional Parkinson's agents include levodopa; levodopa/carbidopa (Sinemet®); Stalevo (carbidopa/levodopa/entacapone); dopamine agonists, e.g., bromocriptine; pergolide; Mirapex® (pramipexole), Permax® (pergolide), and Requip® (ropinirole); COMT inhibitors, e.g., tolcapone, and entacapone; Selegiline (Deprenyl®; Eldepryl®); propranolol; primidone; anticholinergics, e.g., Cogentin®, Artane®, Akineton®, Disipal®, and Kemadrin®; and amantadine.

In each of the combination treatments mentioned above, said first and second components may be administered simultaneously, separately or sequentially. Similarly, said compositions encompass combined preparations for simultaneous, separate or sequential use.

Another preferred group of compounds of the present invention selectively inhibit the reuptake of norepinephrine, serotonin and dopamine. Compounds of the present invention with this pharmacological profile are particularly useful for the treatment of a variety of conditions such as depression, obesity, compulsive disorders (including bulimia, obsessive compulsive disorder, drug addiction including cocaine abuse and alcohol addiction), hypertension, senile dementia, Alzheimer's, memory loss, attention-deficit hyperactivity disorder (ADHD), sexual dysfunction, Parkinsonism, anxiety, chronic fatigue syndrome, panic disorders, cognitive disorders, schizophrenia, gastrointestinal disorders, headache, cardiovascular disorders, epilepsy, smoking cessation, pain, including chronic pain, urinary incontinence, emesis and sleep disorders. They are most particularly useful for the treatment of depression, chronic pain, smoking cessation and obesity.

Accordingly, the present invention provides a compound of formula (I) or a pharmaceutically acceptable salt thereof for use in therapy. In particular, the present invention provides a compound of formula (I) or a pharmaceutically acceptable salt thereof for use as an inhibitor of the uptake of one or more of the monoamine neurotransmitters serotonin, dopamine and norepinephrine.

In another embodiment, the present invention provides a method for inhibiting the uptake of one or more monoamines selected from serotonin, dopamine and norepinephrine in a mammal, comprising administering to a mammal in need of such inhibition an effective amount of a compound of formula (I) or a pharmaceutically acceptable salt thereof. In particular, the present invention provides a method for treating a disorder which is caused by or linked to decreased neurotransmission of one or more monoamines selected from serotonin, dopamine and norepinephrine in a mammal, comprising administering to a mammal in need of such treatment an effective amount of a compound of formula (I) or a pharmaceutically acceptable salt thereof. Such disorders include, for example, disorders of the central and/or peripheral nervous system. Examples of disorders of the central and/or peripheral nervous system are specifically identified above.

It is recognized that the terms "treatment" and "treating" are intended to include improvement of the disorders described herein. Thus, the terms "treatment" and "treating" are intended to refer to all processes wherein there may be a slowing, interrupting, arresting, controlling, or stopping of the progression of the disorders described herein, but does not necessarily indicate a total elimination of all symptoms, and is intended to include prophylactic treatment of such disorders.

In another alternative embodiment, the present invention provides for the use of a compound of formula (I) or a pharmaceutically acceptable salt thereof for the manufacture of a medicament for inhibiting the uptake of one or more monoamines selected from serotonin, dopamine and norepinephrine. In particular, the present invention provides for the use of a compound of formula (I) or a pharmaceutically acceptable salt thereof for the manufacture of a medicament for the treatment of a disorder which is caused by or linked to decreased neurotransmission of one or more monoamines selected from serotonin, dopamine and norepinephrine. Such disorders include, for example, disorders of the central and/or peripheral nervous system. Examples of disorders of the central and/or peripheral nervous system are specifically identified above.

The compounds may be administered by various routes and are usually employed in the form of a pharmaceutical composition.

Accordingly, in a further embodiment, the present invention provides a pharmaceutical composition comprising a compound of formula (I) or a pharmaceutically acceptable salt thereof together with a pharmaceutically acceptable diluent or carrier.

Such compositions may be prepared by methods well known in the pharmaceutical art and normally comprise at least one active compound in association with a pharmaceutically acceptable diluent or carrier. In making the compositions of the present invention, the active ingredient will usually be mixed with a carrier or diluted by a carrier, and/or enclosed within a carrier which may, for example, be in the form of a capsule, sachet, paper or other container.

The compositions indicated can be sterilized and/or can contain auxiliaries such as lubricants, preservatives, stabilizers and/or wetting agents, emulsifiers, salts for affecting the osmotic pressure, buffer substances, colourants, flavourings and/or one or more further active compounds. Compositions of the invention may be formulated so as to provide, quick, sustained or delayed release of the active ingredient after administration to the patient by employing procedures well known in the art.

The compositions are preferably formulated in a unit dosage form, each dosage containing from about 5 to about 500 mg of the active ingredient.

In the context of the present specification, the term "unit dosage form" refers to physically discrete units suitable as unitary doses for human subjects and other mammals, each unit containing a predetermined quantity of one or more compounds of Formula (I) or pharmaceutically acceptable salts thereof, calculated to produce the desired therapeutic effect, together with a pharmaceutically acceptable diluent or carrier.

Compounds of formula (I) may be prepared by conventional organic chemistry techniques and also by solid phase synthesis.

Compounds of formula (I) can be prepared via the 3-aminopyrrolidine intermediate of formula (IV) as illustrated in Scheme 1 below:

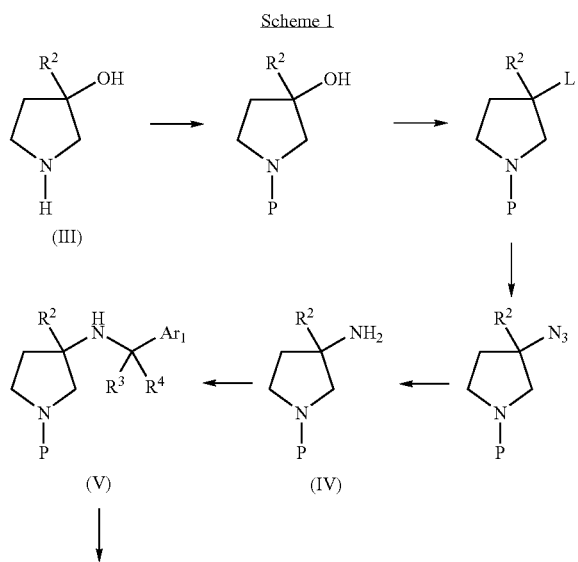

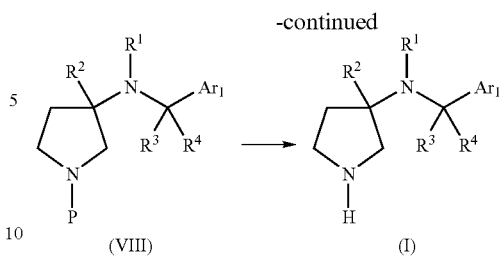

Commercially available 3-hydroxypyrrolidine of formula (III) wherein $R^2$ is hydrogen, can be protected using a suitable nitrogen-protecting group such as those described in T. W. Greene, "Protective Groups in Organic Synthesis", John Wiley and Sons, New York, N.Y., 1991, hereafter referred to as "Greene". For example 3-R-hydroxypyrrolidine (III) can be protected with a tert-butoxycarbonyl group (Boc). The protection reaction can be carried out for example using Boc anhydride in a suitable solvent such as for example tetrahydrofuran (THF) or dichloromethane (DCM) in the presence of a base such as tryethylamine (TEA) or 4-(dimethylamino) pyridine (DMAP). It will be appreciated that for compounds of formula (I) wherein $R^2$ is $C_1$-$C_2$ alkyl, the 3-hydroxypyrrolidine of formula (III) can be prepared from the readily available 3-pyrrolidinone via addition of the appropriate $C_1$-$C_2$ alkyl organometallic. The hydroxy group of the N-protected-3-hydroxypyrrolidine can be converted into a suitable leaving group (L) such as for example chloride, bromide, iodide or mesylate. For example the N-protected-hydroxypyrrolidine can be converted to the mesylate in the presence of mesyl chloride and a suitable base such as triethylamine in a solvent such as DCM. The leaving group (L) (for example, mesylate) is subsequently displaced with the corresponding azide in a suitable solvent such as dimethylformamide (DMF) or dimethylsulphoxide (DMSO). This azide intermediate can be converted to the corresponding N-protected-aminopyrrolidine of formula (IV) via hydrogenation in the presence of a suitable catalyst such as Palladium on charcoal and in a suitable solvent such as methanol or ethanol.

For compounds of formula (I) wherein $R^4$ is H, intermediate (IV) can be alkylated via reductive alkylation with an aldehyde or ketone of formula $R^3$—CO—$Ar_1$ wherein $R^3$ and $Ar_1$ have the values for formula (I) above. The reductive alkylation can be carried out for example as a hydrogenation reaction in the presence of a suitable catalyst such as Palladium on charcoal and a suitable solvent such as for example ethanol. Alternatively, said reductive alkylation can be carried out in the presence of a suitable borane such as sodium triacetoxyborohydride, $NaBH(OAc)_3$ or sodium borohydride, $NaBH_4$ and optionally in the presence of a suitable acid such as acetic acid, in a suitable solvent such as for example dichoroethane (DCE).

Alternatively, the intermediate of formula (V) wherein $R^4$ is H can be prepared as shown in Scheme 2 below by reductive alkylation of readily available 3-aminopyrrolidine of formula (VI) wherein $R^2$ has the values defined for formula (I) above, followed by the protection of the nitrogen in the pyrrolidine ring using a suitable protecting group such as those defined in Greene.

Scheme 2

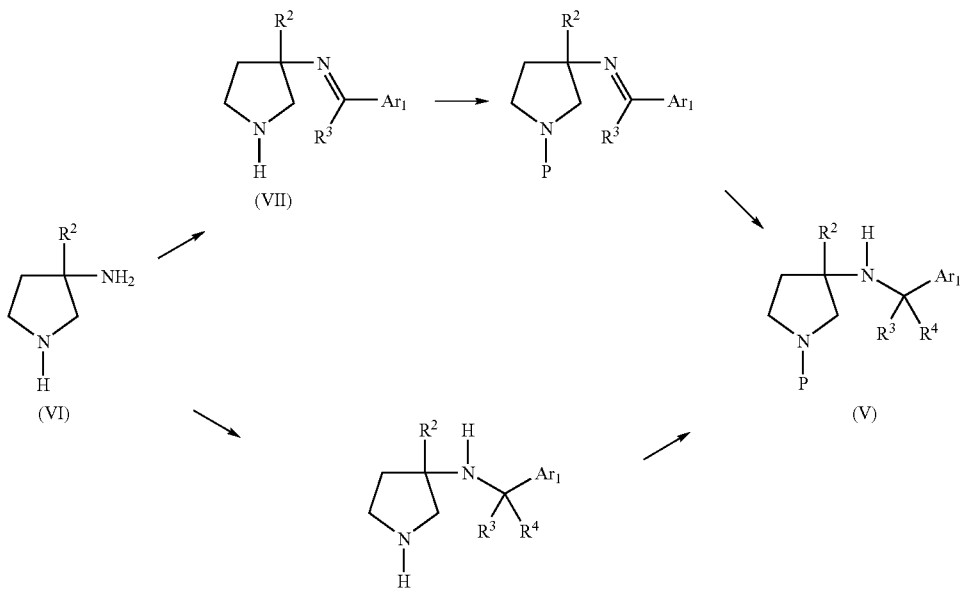

For example the reductive alkylation can be carried out in the presence of an aldehyde or ketone of formula $Ar_1$—CO—$R^3$ wherein $Ar_1$ and $R^3$ have the values defined for formula (I) above. Initial condensation of the amino pyrrolidine with the aldehyde or ketone is undertaken in the presence of a suitable acid such as p-toluenesulphonic acid, in a suitable solvent such as toluene. The resultant imino pyrrolidine intermediate (VII) can then be protected with, for example, a Boc group. The protection reaction can be carried out, for example, in the presence of Boc anhydride and a suitable base such as DMAP, in a suitable solvent such as DCM. Said protected imine is reduced via hydrogenation in the presence of a suitable catalyst such as palladium on charcoal, in a suitable solvent such as ethanol to give the corresponding amine of formula (V). In the alternative, the reductive alkylation described in Scheme 2 can be carried out without isolation of the imine intermediate. For example the alkylation can be carried out by reaction of a compound of formula (VI) with an aldehyde or ketone of formula $Ar_1$—CO—$R^3$ wherein $Ar_1$ and $R^3$ have the values defined for formula (I) above under reductive conditions such as hydrogenation in the presence of a suitable catalyst such as palladium on charcoal in a suitable solvent such as ethanol. The resultant secondary amino pyrrolidine intermediate can then be protected with, for example, a Boc group as described above to give an amine of formula (V).

Intermediates of formula (V) can be converted to compounds of formula (VIII) via reductive alkylation with an aldehyde of formula $R^9$—CHO, wherein $R^9$ is chosen such that $R^9$—$CH_2$ =$R^1$ and $R^1$ has the values defined for formula (I) above. The reductive alkylation can be carried out using standard methods, for instance as those mentioned above with the aldehyde/ketone $Ar_1$—CO—$R^3$. For example a compound of formula (V) can be alkylated with $R^9$—CHO in the presence of a suitable borane, such as $NaBH(OAc)_3$, optionally in the presence of an acid such as acetic acid, in the presence of a suitable solvent such as dichloroethane (DCE).

It will be appreciated that compounds of formula (VIII) may also be obtained from intermediates of formula (IV) by performing the two reductive alkylations in a different order as shown in Scheme 3 below:

Scheme 3

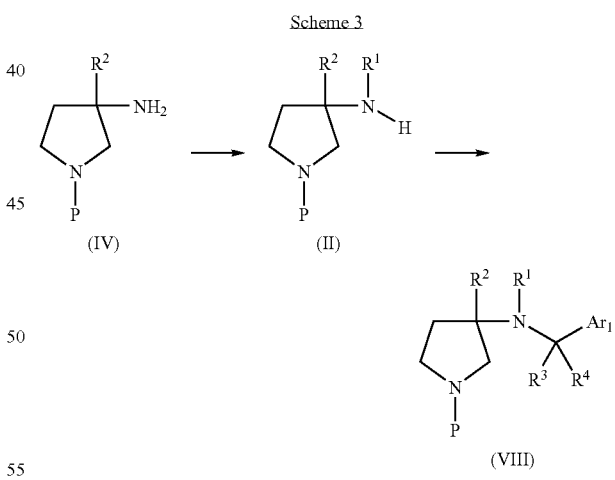

For compounds of formula (I) wherein $R^3$ and $R^4$ are hydrogen the alkylation of intermediate (II) can be carried out with a compound of formula $Ar_1CH_2L_1$ wherein $L_1$ is a suitable leaving group such as chloro, bromo, iodo or mesylate, in the presence of a suitable base such as potassium carbonate and a suitable solvent such as acetonitrile, to give the corresponding intermediate of formula (VIII)$_a$. It will be appreciated that the same reaction can be carried out using $Ar_1$—$CR^3R^4$-$L_1$ wherein $R^3$ and $R^4$ are $C_1$-$C_2$ alkyl.

Scheme 4

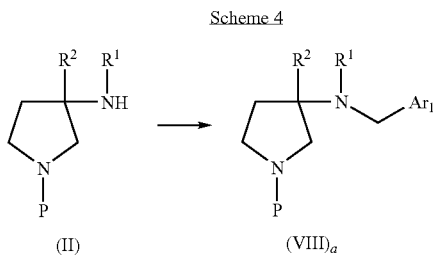

Compounds of formula (I) wherein $R^1$ is —$CH_2$—COO—($C_1$-$C_2$ alkyl) can be prepared by reacting intermediate (V) with a compound of formula $L_2$—$CH_2$—COO—($C_1$-$C_2$ alkyl) wherein $L_2$ is a suitable leaving group such as for example bromo, chloro or iodo. Said reaction can be carried out in the presence of a suitable base such as sodium hydride, in a suitable solvent such as dimethylformamide.

Scheme 5

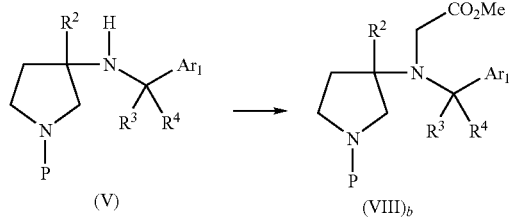

Compounds of formula (I) wherein $R^1$ is —$(CH_2)_m$—$CF_3$, wherein m is from 1 to 5 can be prepared by reacting intermediate (V) with a compound of formula HOOC—$(CH_2)_{m_1}$—$CF_3$, wherein $m_1$ is from 0 to 4. The acid may be activated as its anhydride or acyl chloride, and is reacted in the presence of a suitable base such as triethylamine and a catalytic amount of DMAP, in a suitable solvent such as DCM. The resulting amide can be reduced to the amine of formula (VIII)$_c$ in the presence of a suitable borane. For example, for compounds wherein m is 1, the reduction can be carried out in the presence of $BH_3$—$Me_2S$ borane-dimethyl sulphide complex, in a suitable solvent such as THF.

Scheme 6

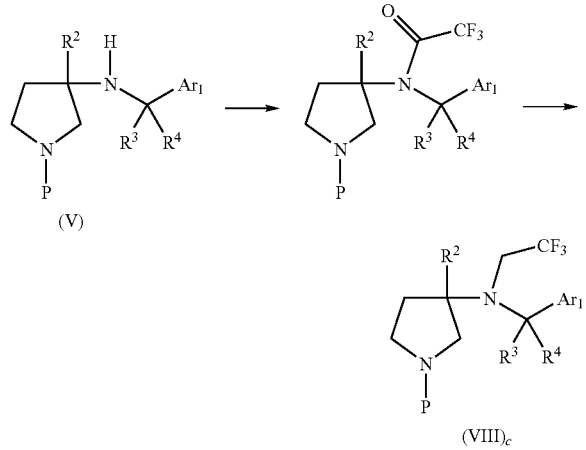

Compounds of formula (I) wherein $R^1$ is —($C_1$-$C_6$ alkylene)—OH can be prepared by reacting intermediate (V) with an epoxide. For example for compounds wherein $R^1$ is —$CH_2$—$C(CH_3)_2$—OH, the intermediate of formula (V) is reacted with 2,2-dimethyloxirane, in a suitable solvent such as aqueous ethanol.

Scheme 7

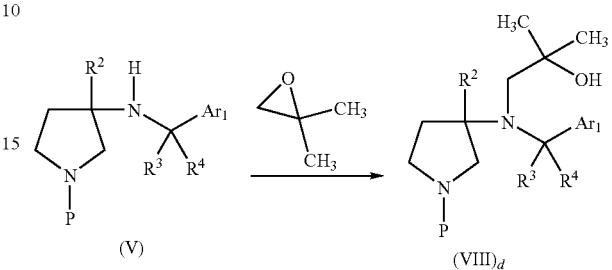

Alternatively compounds of formula (I) wherein $R^1$ is —($C_1$-$C_6$alkylene)—OH can be prepared by reacting intermediate (V) with an ω-haloalkanoate, such as methylbromoacetate, in the presence of a base such a sodium hydrogen carbonate in a solvent such as acetonitrile. The intermediate ester is then reacted with 2 equivalents of methyl magnesium bromide in THF to yield the tertiary alcohol(VIII)$_d$:

Scheme 8

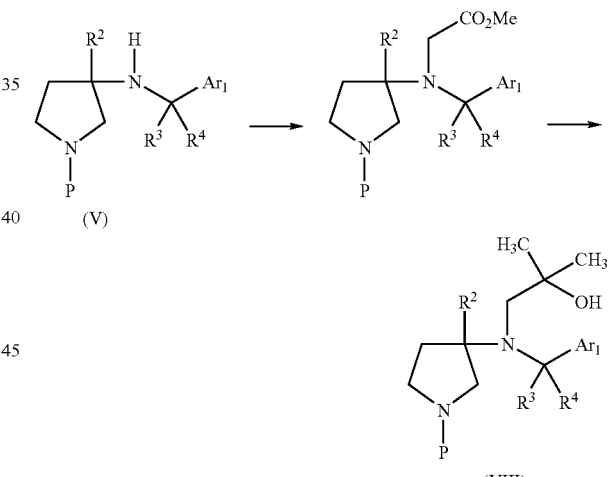

It will be appreciated that the scheme 8 above applies to alkylene chains longer than —$CH_2$—.

Compounds of formula (I) wherein $R^1$ is —$C_2$-$C_6$ alkenyl, —($C_1$-$C_6$ alkylene)—S—($C_1$-$C_3$ alkyl), —($C_1$-$C_6$ alkylene)—O—($C_1$-$C_3$ alkyl), —($C_1$-$C_6$ alkylene)—O—($C_3$-$C_6$ cycloalkyl), —($C_1$-$C_6$ alkylene)—$SO_2$—($C_1$-$C_3$ alkyl), —($C_1$-$C_6$ alkylene)—$OCF_3$, or —($C_1$-$C_6$ alkylene)—CN, can be prepared via alkylation of intermediate (V) with a compound of formula $L_2$—($C_2$-$C_6$ alkenyl), $L_2$—($C_1$-$C_6$ alkylene)—S—($C_1$-$C_3$ alkyl), $L_2$—($C_1$-$C_6$ alkylene)—O—($C_1$-$C_3$ alkyl), $L_2$—($C_1$-$C_6$ alkylene)—O—($C_3$-$C_6$ cycloalkyl), $L_2$—($C_1$-$C_6$ alkylene)—$SO_2$—($C_1$-$C_3$ alkyl), $L_2$—($C_1$-$C_6$ alkylene)—$OCF_3$, or $L_2$—($C_1$-$C_6$ alkylene)—CN respectively, wherein $L_2$ is a suitable leaving group such as chloro, bromo, iodo or mesylate, in the presence of a suitable base such as potassium carbonate and a suitable solvent such as acetonitrile, to give the corresponding intermediate of formula (VIII).

Scheme 9

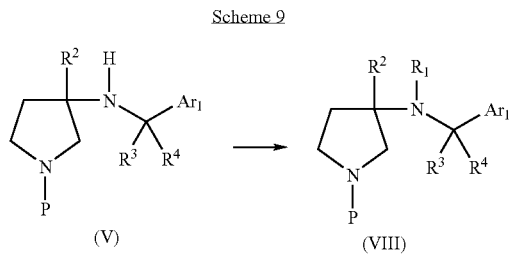

Compounds of formula (I) wherein R¹ is a group of formula (i) can be prepared using the synthesis illustrated in scheme 10 for compounds wherein R¹ is 4-tetrahydropyranyl. The compound of formula (IV) can be alkylated via reductive alkylation using standard methods, as those mentioned above with the ketone Ar₁—CO—R³. For example compound of formula (IV) can be alkylated with 4-tetrahydropyranone in the presence of a suitable borane, such as sodium borohydride or NaBH(OAc)₃, optionally in the presence of an acid such as acetic acid, in the presence of a suitable solvent such as dichloroethane (DCE). Then, the secondary amine can be alkylated with a compound of formula Ar₁, CH₂L₁ wherein L₁ is a suitable leaving group such as chloro, bromo, iodo or mesylate, in the presence of a suitable base such as potassium carbonate and a suitable solvent such as acetonitrile, to give the corresponding intermediate of formula (VIII)$_f$. It will be appreciated that, as mentioned above, the same reaction can be carried out using Ar₁—CR³R⁴-L₁ wherein R³ and R⁴ are C₁-C₂ alkyl.

Scheme 10

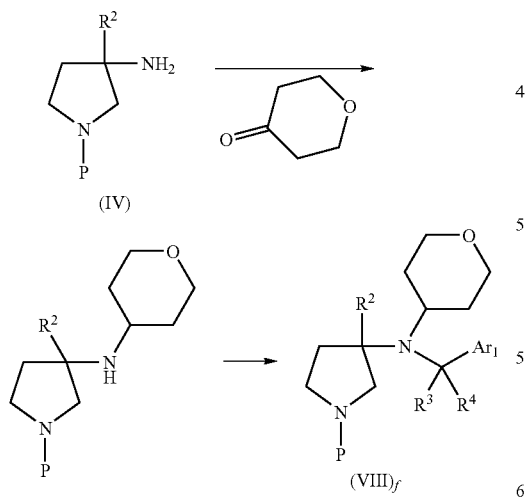

It will be appreciated that for compounds of formula (I) wherein R¹ is a group of formula (i) and r is 1 then the reductive amination can be carried out using the same reaction conditions but using the corresponding homologous aldehyde of formula

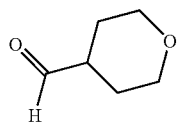

instead of 4-tetrahydropyranone. Alternatively, compounds of formula (I) wherein R¹ is a group of formula (i) and r is 1 can be prepared via formation of an amide, followed by reduction of this amide bond to the corresponding amine as shown in scheme 11 below:

Scheme 11

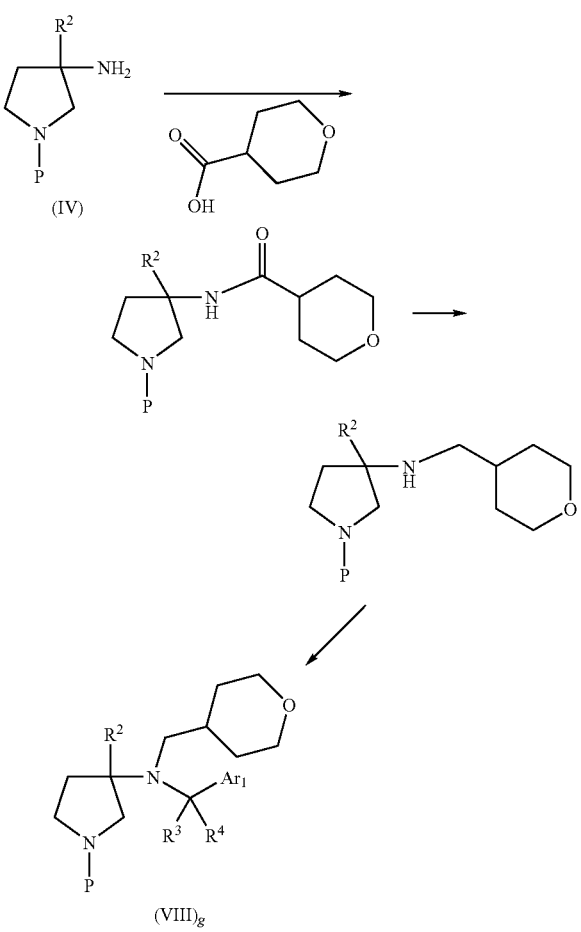

The coupling reaction can be carried out using standard methods known in the art. The reduction of the amide bond can also be carried out by general methods known in the art, for example using the same reduction conditions as those used in scheme 6, such as in the presence of BH₃—Me₂S (borane-dimethyl sulphide complex), in a suitable solvent such as THF.

Alternatively, compounds of formula (I) wherein R¹ is a group of formula (i) wherein r is 0 can be prepared by a process illustrated in scheme 12 for compounds wherein —Z is hydrogen, s is 1, t is 2, each R⁵, R⁶, R⁷ and R⁸ are hydrogen and —X— is —O—, (i.e. R¹ is 2-tetrahydrofuranyl). The compound of formula (IV) can be alkylated with a compound of formula:

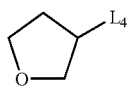

wherein L₄ is a suitable leaving group such as chloro, bromo, iodo, mesylate or tosylate, in the presence of a suitable base such as potassium carbonate and a suitable solvent such as acetonitrile, to give the corresponding secondary amine which can be subsequently alkylated with a compound of formula Ar₁CH₂L₁ wherein L₁ is a suitable leaving group such as chloro, bromo, iodo or mesylate, in the presence of a suitable base such as potassium carbonate and a suitable solvent such as acetonitrile, to give the corresponding intermediate of formula (VIII)$_f$. It will be appreciated that as mentioned above the same reaction can be carried out using Ar₁—CR³R⁴-L₁ wherein R³ and R⁴ are C₁-C₂ alkyl.

Scheme 12

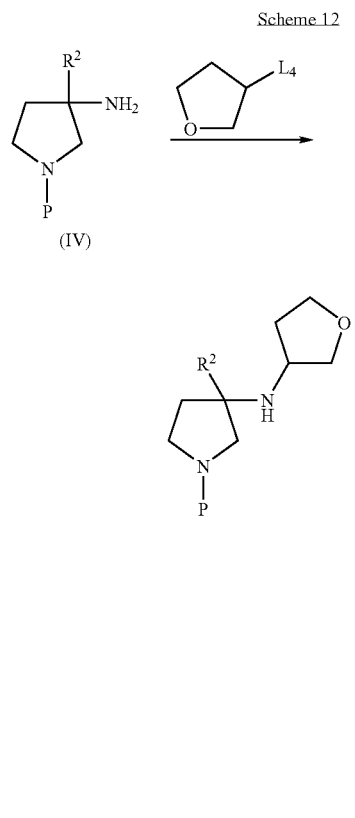

The tetrahydrofuranyl intermediates can be prepared from the corresponding 3-hydroxytetrahydrofuran, wherein the hydroxy group is converted into the leaving group using standard methods.

Compounds of formula (I) wherein R¹ is a group of formula (i) and —X— is —SO₂— can be prepared from the corresponding intermediates (VIII)$_f$ wherein the thioether is oxidized by a suitable oxidizing agent, such as peracetic acid, to the corresponding sulphoxide as shown in scheme 13 below:

Scheme 13

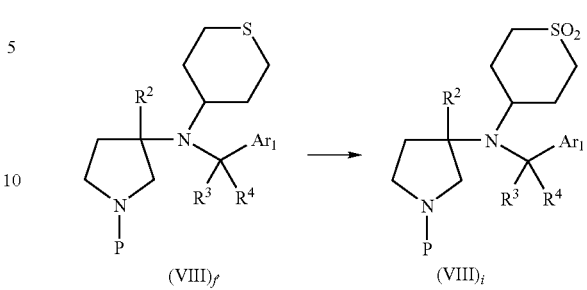

Compounds of formula (I) wherein R¹ is a group of formula (ii) can be prepared using the synthesis illustrated in scheme 14 for compounds wherein R¹ is oxabicyclo[3,2,1] octan-3-yl. The compound of formula (IV) can be alkylated via reductive alkylation using standard methods, as those mentioned above with the aldehyde or ketone Ar₁—CO—R³. For example compound of formula (IV) can be alkylated with oxabicyclo[3,2,1]octan-3-one in the presence of a suitable borane, such as sodium borohydride or NaBH(OAc)₃, optionally in the presence of an acid such as acetic acid, in the presence of a suitable solvent such as dichloroethane (DCE). Then, the secondary amine can be alkylated with a compound of formula Ar₁CH₂L₁ wherein L₁ is a suitable leaving group such as chloro, bromo, iodo or mesylate, in the presence of a suitable base such as potassium carbonate and a suitable solvent such as acetonitrile, to give the corresponding intermediate of formula (VIII)$_j$. It will be appreciated that as mentioned above the same reaction can be carried out using Ar₁—CR³R⁴-L₁ wherein R³ and R⁴ are C₁-C₂ alkyl.

Scheme 14

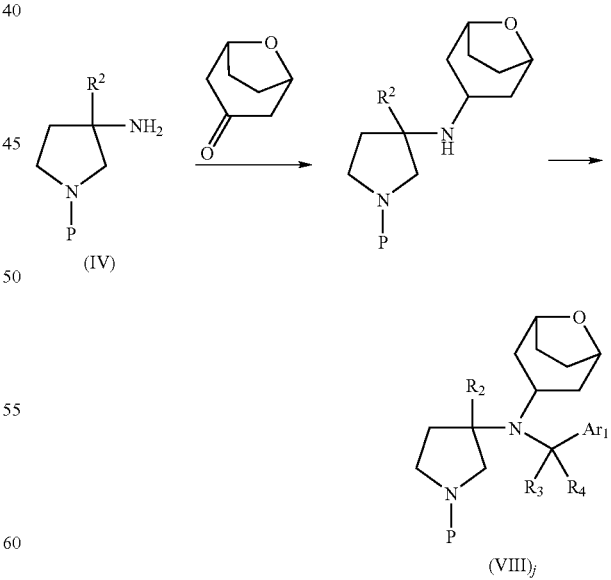

The oxabicyclo[3,2,1]octan-3-one intermediate is prepared according to the method described in A E Hill, G Greenwood and H M R Hoffmann JACS 1973, 95, 1338. It will be appreciated that for compounds of formula (I) wherein $R^1$ is a group of formula (ii) and r is 1 then the reductive amination can be carried out using the same reaction conditions but using the corresponding homologous aldehyde of formula

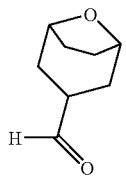

instead of the corresponding oxabicyclo[3,2,1]octan-3-one.

Compounds of formula (I) wherein $Ar_1$ is a substituted or unsubstituted pyridinyl group can be prepared by a process illustrated in scheme 15 for compounds wherein $R^3$ and $R^4$ are hydrogen and $Ar_1$ is 3-phenylpyrid-2-yl.

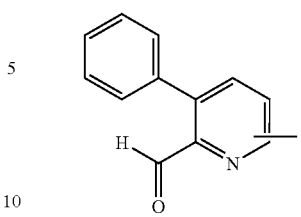

in the presence of a suitable borane, such as sodium borohydride or $NaBH(OAc)_3$, optionally in the presence of an acid such as acetic acid, in the presence of a suitable solvent such as dichloroethane (DCE). Then, the secondary amine can be alkylated using the general methods described above for the incorporation of $R^1$. The intermediate aldehyde can be prepared via reduction of readily available methyl 3-phenyl picolinate to the corresponding alcohol and subsequent oxidation to the aldehyde as shown in scheme 16 below.

Scheme 15

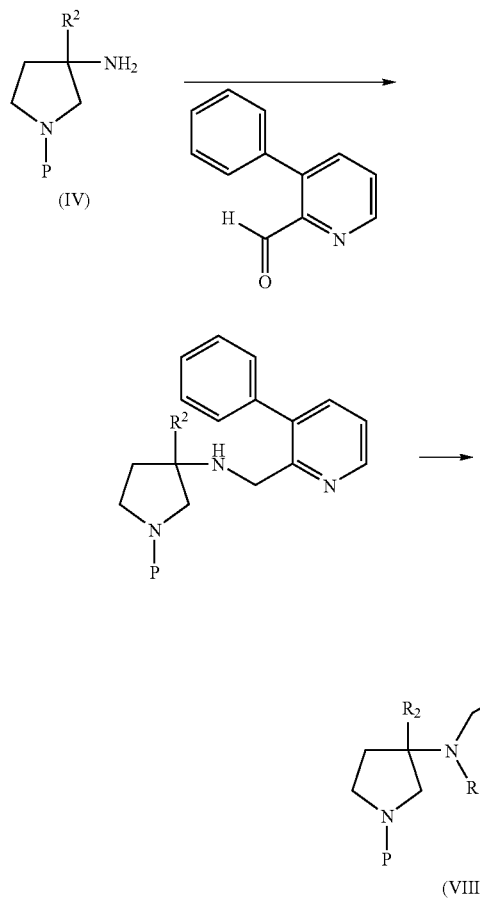

Scheme 16

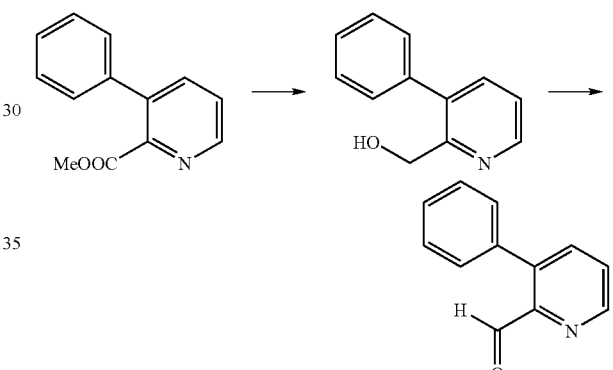

The reduction step can be carried out in the presence of a suitable reducing agent such as lithium borohydride in a suitable solvent such as tetrahydrofuran. The oxidation to the aldehyde can be carried out under Swern conditions such as oxalyl chloride and DMSO in DCM.

Compounds of formula (I) wherein $Ar_1$ is a substituted or unsubstituted phenyl group can be prepared by a process illustrated in scheme 17 for compounds wherein $R^3$ and $R^4$ are hydrogen and $Ar_1$ is 2-(3-pyridinyl)phenyl.

Scheme 17

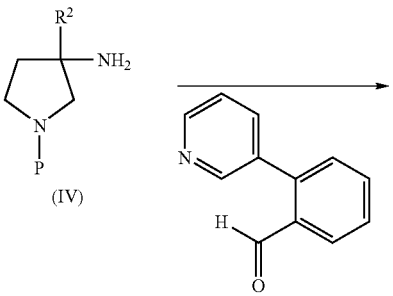

The compound of formula (IV) can be alkylated via reductive alkylation using standard methods, as those mentioned above with the aldehyde or ketone $Ar_1$—CO—$R^3$. For example compound of formula (IV) can be alkylated with an aldehyde of formula:

-continued

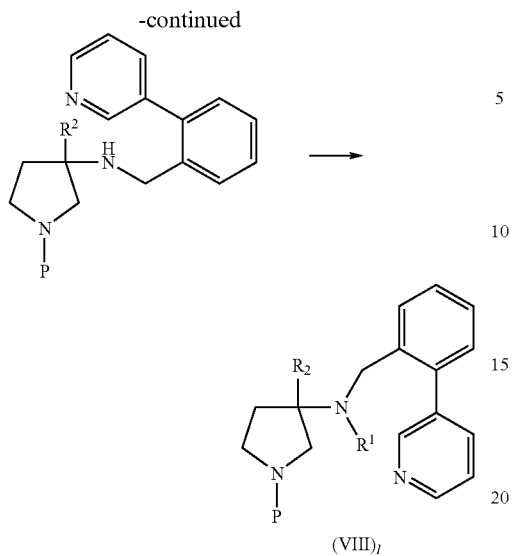

(VIII)$_l$

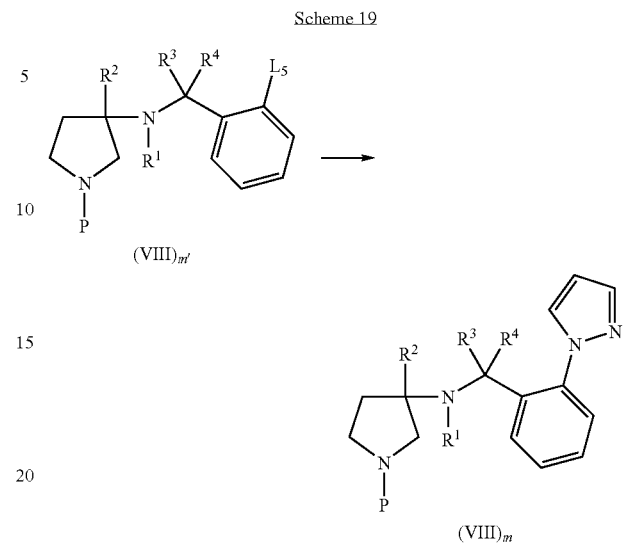

(VIII)$_{m'}$ (VIII)$_m$

The compound of formula (IV) can be alkylated via reductive alkylation using standard methods, as those mentioned above with the aldehyde or ketone Ar$_1$—CO-R$^3$. For example compound of formula (IV) can be alkylated with a aldehyde of formula:

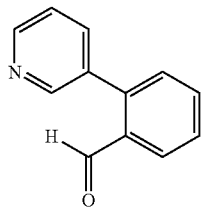

in the presence of a suitable borane, such as sodium borohydride or NaBH(OAc)$_3$, optionally in the presence of an acid such as acetic acid, in the presence of a suitable solvent such as dichloroethane (DCE). Then, the secondary amine can be alkylated using the general methods described above for the incorporation of R$^1$. The intermediate aldehyde can be prepared from the commercially available 2-formyl phenyl boronic acid via palladium coupling in the presence of 3-bromopyridine, a suitable palladium catalyst such as Pd(PPh$_3$)$_4$ and a suitable base such as potassium carbonate in a suitable solvent such as acetonitrile, as shown in scheme 18 below.

Scheme 18

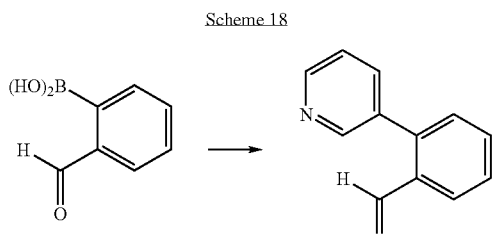

Compounds of formula (I) wherein Ar$_1$ is a phenyl group substituted with a 1-pyrazolyl group can be prepared by a process illustrated in scheme 19.

The pyrazolyl group can be incorporated by reacting a compound of formula (VIII)$_{m'}$, wherein L$_5$ is a suitable leaving group such as bromo, chloro or iodo, with pyrazole in the presence of a suitable base such as potassium carbonate and a catalytic amount of copper iodide in a suitable solvent such as for example DMF. The compound of formula (VIII)$_{m'}$ can be prepared by any of the methods mentioned above for compounds wherein Ar1 is a phenyl group substituted with a halogen atom such as chloro, bromo or iodo.

It will be appreciated that any of the intermediates (VIII), (VIII)$_{a-m}$ are then deprotected using suitable deprotecting conditions such as those discussed in Greene, to give the corresponding compounds of formula (I). For example if the protecting group is a boc group, the deprotection reaction can be carried out in trifluoroacetic acid in a suitable solvent such as DCM. Alternatively the reaction can be carried out in methanolic or ethanolic hydrochloric acid.

Scheme 20

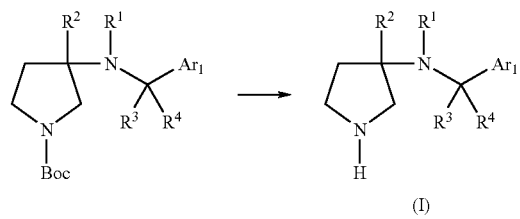

(I)

Compounds of formula (I) wherein R$^3$ and R$^4$ are both hydrogen may also be prepared by solid phase synthesis by the route shown in Scheme 21 below.

Scheme 21

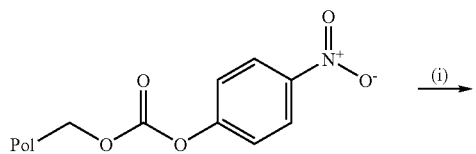

-continued

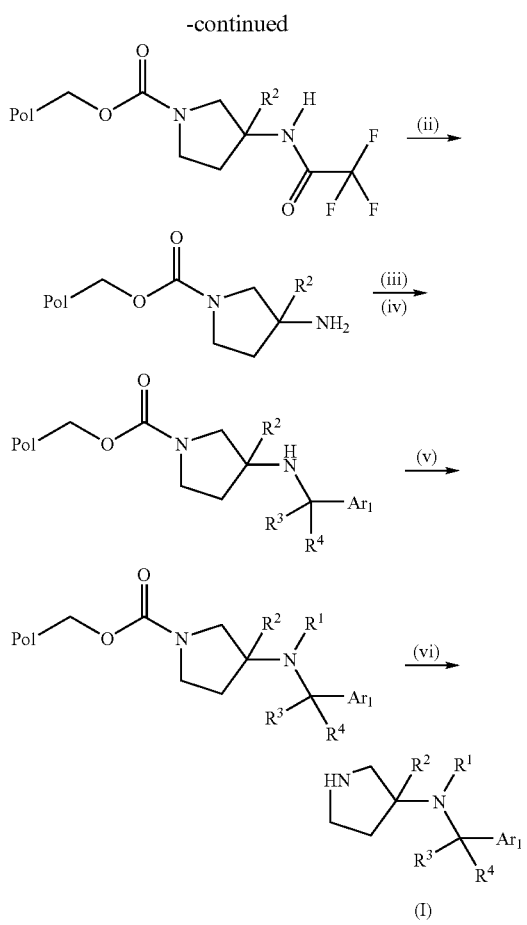

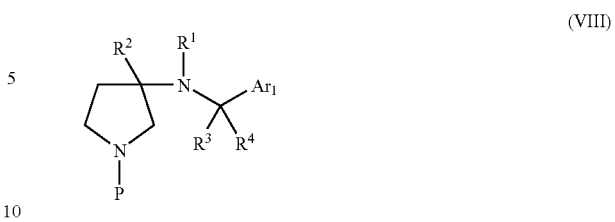

The sequence is preferably performed on a polystyrene resin. The process may be run in a combinatorial fashion such that all possible compounds from sets of precursors $Ar_1CHO$ and $R^9CHO$ may be prepared, wherein $R^9$ is chosen such that $R^9$—$CH_2$=$R^1$, and $R^1$ and $Ar_1$ have the values defined above for formula (I). The sequence is performed without characterisation of the resin-bound intermediates. In step (i) 3-trifluoroacetamido-pyrrolidine is bound to a solid support by reaction with 4-nitrophenyl carbonate activated polystyrene resin in the presence of a base, such as N,N-diisopropylethylamine, in a solvent such as DMF. In step (ii), the trifluoroacetamido protecting group is cleaved by hydrolysis with a base such as aqueous lithium hydroxide. In step (iii) the primary amine is then condensed with a substituted benzaldehyde in the presence of a dehydrating agent, such as trimethylorthoformate, to form the intermediate imine. In step (iv) the imine is reduced with a borane reducing agent, such as sodium cyanoborohydride, in a solvent such as DMF, containing acetic acid. In step (v) the resultant secondary amine is then reductively alkylated with an aldehyde in the presence of a reducing agent such as sodium triacetoxyborohydride in a solvent, such as DMF. In step (vi) the desired product of formula (I) is finally cleaved from the resin with acid, such as aqueous trifluoroacetic acid.

The present invention also provides a process for producing a compound of formula (I) above, which comprises deprotecting a compound of the formula (VIII)

where P is an N-protecting group, optionally followed by the further step of forming a pharmaceutically acceptable salt. Suitable N-protecting groups, will be known to the person skilled in the art and are described in, for example, Greene. They include, for example, boc, benzyl, benzyloxycarbonyl and acetyl.

The following Preparations and Examples illustrate routes to the synthesis of the compounds of the invention.

Preparation 1: 1,1-Dimethylethyl (3S)-3-aminopyrrolidine-1-carboxylate a) 1,1-Dimethylethyl (3R)-3-hydroxypyrrolidine-1-carboxylate.

Solid di-tert-butyldicarbonate (38.8 g, 178 mmol) was added in portions over 15 minutes to a stirred solution of (3R)-pyrrolidin-3-ol hydrochloride (20 g, 162 mmol), triethylamine (24. 8 mL, 178 mmol) and 4-(dimethylamino)-pyridine (DMAP) (20 mg) in dry dichloromethane (300 mL). After stirring for 2 hours at room temperature, the mixture was washed with aqueous citric acid, then brine. The organic extracts were dried ($MgSO_4$), filtered and evaporated in vacuo to give an oil. This was purified by flash chromatography on silica, eluting with ethyl acetate/cyclohexane (20:80 to 60:40), to give the title compound as a solid.

b) 1,1-Dimethylethyl (3R)-3-[(methylsulfonyl)oxy]-pyrrolidine-1-carboxylate.

Methanesulfonyl chloride (5. 26 mL, 68 mmol) was added dropwise over 5 minutes to a stirred solution of 1,1-dimethylethyl (3R)-3-hydroxypyrrolidine-1-carboxylate (10.6 g, 56.7 mmol) and triethylamine (11.8 mL, 85 mmol) in dichloromethane (250 mL) at −10° C. After stirring for 1 hour at 0° C., the reaction was quenched by addition of water. The organic phase was washed with brine, dried ($MgSO_4$), filtered and evaporated in vacuo to give an oil. This was purified by flash chromatography on silica, eluting with ethyl acetate/cyclohexane (25:75 to 50:50), to give the title compound as an oil.

c) 1,1-Dimethylethyl (3S)-3-azidopyrrolidine-1-carboxylate.

Sodium azide (4.4 g, 67.4 mmol) was added to a solution of 1,1-dimethylethyl (3R)-3-[(methylsulfonyl)oxy]-pyrrolidine-1-carboxylate (14.3 g, 54 mmol) in dry dimethylformamide (75 mL) and the resultant suspension heated at 65° C. for 8 hours. After cooling to room temperature, the reaction mixture was diluted with water and extracted into diethyl ether. The organic phase was washed two further times with water, then brine. The organic extracts were dried ($MgSO_4$), filtered and evaporated in vacuo to give an oil. This was purified by flash chromatography on silica, eluting with diethyl ether/cyclohexane (20:80 to 40:60), to give the title compound as an oil.

d) 1,1-Dimethylethyl (3S)-3-aminopyrrolidine-1-carboxylate.

A mixture of 1,1-dimethylethyl (3S)-3-azidopyrrolidine-1-carboxylate (9.0 g, 2.97 mmol) and 5% palladium-on-carbon (0.70 g) in methanol (150 mL) was hydrogenated in a Parr apparatus at 65 p.s.i. for 4 hours. The catalyst was removed by filtration through Celite and the solvent evaporated in vacuo to give an oil. The resultant title compound was used in subsequent reactions without further purification.

Preparation 2: 1,1-Dimethylethyl (3R)-3-aminopyrrolidine-1-carboxylate 1,1-Dimethylethyl (3R)-3-aminopyrrolidine-1-carboxylate was similarly prepared as described above, from (3S)-pyrrolidin-3-ol.

Preparation 3: 1-Dimethylethyl (3S)-3-[(1-methylethyl)amino]-pyrrolidine-1-carboxylate A mixture of 1,1-dimethylethyl (3S)-3-aminopyrrolidine-1-carboxylate (3.0 g) and 5% palladium-on-carbon (0.35 g) in methanol (75 mL) and acetone (15 mL) was hydrogenated in a Parr apparatus at 65 p.s.i. for 3 hours. The catalyst was removed by filtration through Celite and the solvent evaporated in vacuo to give an oil. The resultant title compound was used in subsequent reactions without further purification. $^1$H NMR (300 MHz, CDCl$_3$) $\delta_H$: 1.11-1.19 (m, 6H), 1.45 (s, 9H), 1.55-1.75 (m, 1H), 2.01-2.15 (m, 1H), 2.80-2.92 (m, 1H), 2.93-3.05 (m, 1H), 3.25-3.70 (m, 4H).

The following secondary amines were similarly prepared by reductive alkylation of 1,1-dimethylethyl (3S)-3-aminopyrrolidine-1-carboxylate with the appropriate aldehyde or ketone.

Preparation 4: 1,1-Dimethylethyl (3S)-3-(cyclopentylamino)perrolidine-1-carboxylate Preparation 5: 1,1-Dimethylethyl (3S)-3-[(cyclohexylmethyl)amino]-pyrrolidine-1-carboxylate Preparation 6: 1,1-Dimethylethyl (3S)-3-(propylamino)pyrrolidine-1-carboxylate Preparation 7: 1,1-Dimethylethyl (3S)-3-(cyclobutylamino)pyrrolidine-1-carboxylate Preparation 8: 1,1-Dimethylethyl (3S)-3-(cyclohexylamino)pyrrolidine-1-carboxylate Preparation 9: 1,1-Dimethylethyl (3S)-3-(2-methoxy-1-methylethyl amino)pyrrolidine-1-carboxylate Preparation 10: 1,1-Dimethylethyl (3S)-3-({[2-(trifluoromethyl)phenyl]-methyl}amino)pyrrolidine-1-carboxylate Method A
a) (3S)-N-{(E)-[2-(Trifluoromethyl)phenyl]methylidene}-pyrrolidin-3-amine.

3(S)-Pyrrolidin-3-amine (0.45 g, 5.2 mmol) and trifluoromethylbenzaldehyde (0.87 g, 5.0 mmol), a crystal of 4-toluenesulphonic acid and toluene were refluxed with stirring for one day, using a Dean and Stark apparatus. The solution was evaporated in vacuo to give the title compound as a brown oil (M+H=243).

b) 1,1-Dimethylethyl (3S)-3-({(E)-[2-(trifluoromethyl)-phenyl]methylidene}amino)pyrrolidine-1-carboxylate.

(3S)-N-{(E)-[2-(Trifluoromethyl)phenyl]methylidene}-pyrrolidin-3-amine (1.21 g, 5 mmol) was dissolved in dichloromethane (50 mL), and di-tert-butyl dicarbonate (1.1 g, 5.05 mmol) followed by DMAP (60 mg, 0.5 mmol) was added. After stirring under nitrogen for 4 hours, the solution was evaporated in vacuo to give the title compound as a brown oil (M+H=343).

c) 1,1-Dimethylethyl (3S)-3-({[2-(trifluoromethyl)-phenyl] methyl}amino)pyrrolidine-1-carboxylate.

1,1-Dimethylethyl (3S)-3-({(E)-[2-(trifluoromethyl)-phenyl]methylidene}amino)pyrrolidine-1-carboxylate (1.71 g, 5 mmol) was hydrogenated in the presence of 5% palladium on carbon (250 mg) at 65 psi in ethanol (60 mL). After 3.5 hours, the catalyst was filtered off and the filtrate evaporated in vacuo to give an oil. The oil was purified by automated flash chromatography over silica, eluting with 10% ethyl acetate in cyclohexane (10:90 to 50:50), to give the title compound as a colourless oil (1.0 g, 58%; M+H=345).

Method B
a) (3S)-N-{[2-(Trifluoromethyl)phenyl]methyl}pyrrolidin-3-amine.

A mixture of 3(S)-pyrrolidin-3-amine (4 g, 46.5 mmol), 2-trifluoromethylbenzaldehyde (9.1 g, 46.5 mmol), 5% palladium on carbon (0.4 g) and ethanol (150 mL) was hydrogenated at 60 psi for 3 hours using a Parr hydrogenator. The catalyst was filtered off and the filtrate evaporated in vacuo to give the title compound as an oil. MS: [M+H]=245.

b) 1,1-Dimethylethyl (3S)-3-({[2-(trifluoromethyl)-phenyl] methyl}amino)pyrrolidine-1-carboxylate.

(3S)-N-{[2-(Trifluoromethyl)phenyl]methyl}pyrrolidin-3-amine (12 g, 49.2 mmol) was dissolved in dichloromethane (120 mL), then di-tert-butyl dicarbonate (10.7 g, 49.2 mmol) and DMAP (40 mg, 0.33 mmol) were added. After stirring under nitrogen for 1 day, the solution was evaporated in vacuo to give an oil. The oil was purified by automated flash chromatography over silica, eluting with ethyl acetate in cyclohexane (0:100 to 40:60), to give the title compound as a colourless oil. MS: [M+H]=345.

Preparation 11: 1,1-Dimethylethyl (3S)-3-({[4-fluoro-2-(trifluoromethyl)-phenyl]methyl}amino) pyrrolidine-1-carboxylate 1,1-Dimethylethyl (3S)-3-aminopiperidine-1-carboxylate (5 g) and 4-fluoro-2-(trifluoromethyl)benzaldehyde (5.15 g, 26.8 mmol) were allowed to stir in methanol for 16 h at room temperature. Sodium borohydride (1.62 g, 26.8 mmol) was then added portionwise. The resulting solution was further stirred for 2 h at room temperature. The solvent was evaporated in vacuo, water was added, and the solution extracted with dichloromethane. The organic extracts were absorbed onto a methanol washed cationic ion exchange resin (Isolute™ SCX-2). The basic components were recovered from the column by elution with 7N ammonia in methanol. The resultant solution was concentrated in vacuo to yield the desired compound as an oil. This was further purified by column chromatography on silica gel, eluting with ethyl acetate/iso-hexane (0:100 to 40:60). The title compound was used in subsequent reactions without further purification. $^1$H NMR (300 MHz, CDCl$_3$) $\delta_H$: 7.37-7.28 (m, 2H), 7.24-7.20 (m, 1H), 3.80 (s, 2H), 3.52-3.48 (m, 2H), 3.32 (m, 3H), 3.12 (m, 1H), 2.08-2.0 (m, 1H), 1.75 (m, 1H), 1.45 (s, 9H).

The following secondary amines were similarly prepared by reductive alkylation of 1,1-dimethylethyl (3S)-3-aminopiperidine-1-carboxylate with the appropriate benzaldehyde.

Preparation 12: 1,1-Dimethylethyl (3S)-3-{[(3,5-dichloro-phenyl)methyl]-amino}pyrrolidine-1-carboxylate Preparation 13: 1,-Dimethylethyl (3S)-3-{[(5-fluoro-2-(trifluoromethyl)-phenyl)methyl]amino}pyrrolidine-1-carboxylate Preparation 14: 1,1-Dimethylethyl (3S)-3-{[(2-chloro-4-fluoro-phenyl)-methyl]amino}pyrrolidine-1-carboxylate Preparation 15: 1,1-Dimethylethyl (3S)-3-{[(2,4-dichloro-phenyl)methyl]amino}pyrrolidine-1-carboxylate Preparation 16: 1,1-Dimethylethyl (3S)-3-{[(2,3-dichloro-phenyl)methyl]amino}pyrrolidine-1-carboxylate Preparation 17: 1,1-Dimethylethyl (3S)-3-{[(2-chloro-3-methyl-phenyl)methyl]amino}pyrrolidine-1-carboxylate Preparation 18: 1,1-Dimethylethyl (3S)-3-{[(2-chloro-6-fluoro-phenyl)methyl]amino}pyrrolidine-1-carboxylate

EXAMPLE 1

(3S)-N-(1-Methylethyl)-N-{[3,5-dichlorophenyl]-methyl}pyrrolidin-3-amine D-tartrate a) 1,1-Dimethylethyl (3S)-3-((1-methylethyl)-{[3,5-dichlorophenyl]methyl}amino)-pyrrolidine-1-carboxylate.

To a solution of 1,1-dimethylethyl (3S)-3-[(1-methylethyl)amino]-pyrrolidine-1-carboxylate (1 g, 4.4 mmol) and 3,5-dichlorobenzaldehyde (1.53 g, 8.77 mmol) in trimethylorthoformate (10 mL) at room temperature under a nitrogen atmosphere was added portionwise sodium triacetoxyborohydride (1.3 g, 6.1 mmol). The reaction was stirred at room temperature for 72 hours, then evaporated to dryness in vacuo. The residue was taken up in aqueous saturated sodium hydrogen carbonate/dichloromethane mixture. The aqueous layer was further extracted with dichloromethane (3×), and the combined organic layers dried (MgSO$_4$) and evaporated to dryness in vacuo. The resulting residue was dissolved in methanol and filtered through a cationic ion exchange resin (Isolute™ SCX-2). The basic components were recovered from the column by elution with 2N ammonia in methanol. This solution was concentrated in vacuo to yield the desired compound as a yellow oil that was used in the next step without further purification. $^1$H NMR (300 MHz, CDCl$_3$) δ$_H$: 0.95-1.04 (m, 6H), 1.45 (s, 9H), 1.56-1.77 (m, 1H), 1.8-1.94 (m, 1H), 2.9-3.09 (m, 2H), 3.11-3.25 (m, 1H), 3.32,3.56 (m, 3H), 3.59 (s, 2H), 7.15-7.27 (m, 3H). MS: [M+H]=387/389/391.

b) (3S)-N-(1-Methylethyl)-N-{[3,5-dichlorophenyl]methyl}-pyrrolidin-3-amine D-tartrate.

1,1-Dimethylethyl (3S)-3-((1-methylethyl)-{[3,5-dichlorophenyl]methyl}amino)pyrrolidine-1-carboxylate (1.36 g, 3.51 mmol) was dissolved in a mixture of dichloromethane and trifluoroacetic acid (10 mL, 2:1) and stirred at room temperature for 30 minutes. The reaction solution was concentrated in vacuo and redissolved in MeOH. This solution was filtered through a cationic ion exchange resin (Isolute™ SCX-2). The basic components were isolated by elution with 2N ammonia in methanol and further purified by UV guided prep-LC. The desired compound was isolated from the acidic prep-LC mobile phase via a cationic ion exchange resin as described above. After evaporation in vacuo the residue was dissolved in hot cyclohexane (5 mL) and to this was added an equimolar amount of D-tartaric acid (450 mg), dissolved in a minimal amount of hot isopropanol. The solution was evaporated in vacuo to yield the title compound as a solid. $^1$H NMR (300 MHz, d6-DMSO) δ$_H$: 0.95-0.99 (m, 6H), 1.58-1.71 (m, 1H), 1.91-2.00 (m, 1H), 2.76-2.91 (m, 2H), 2.97-3.07 (m, 1H), 3.18-3.25 (m, 2H), 3.55-3.67 (m, 4H), 3.95 (s, 2H), 7.37-7.38 (m, 2H), 7.43-7.45 (m, 1H). MS: [M+H]=287/289/291.

The following Examples were similarly prepared as described above for Example 1, by reductive alkylation of 1,1-dimethylethyl (3S)-3-[(1-methylethyl)amino]-pyrrolidine-1-carboxylate with the appropriate substituted benzaldehyde:

EXAMPLE 2

(3S)-N-(1-Methylethyl)-N-{[2-(methylthio)phenyl]methyl}-pyrrolidin-3-amine fumarate $^1$H NMR (300 MHz, CD$_3$OD) δ$_H$: 0.99 (s, 6H), 2.06 (m, 1H), 2.37 (s, 3H), 3.01-2.85 (m, 1H), 3.18-3.06 (m, 1H), 3.46-3.19 (m, 4H), 3.67 (dd, 2H), 6.60 (s, 2H), 7.10-7.02 (m, 1H), 7.20-7.11 (m, 2H), 7.40 (dd, 1H); MS: [M+H]=265.

EXAMPLE 3

(3S)-N-(1-Methylethyl)-N-{[2-trifluoromethyl)oxy]-phenyl}methyl)pyrrolidin-3-amine fumarate $^1$H NMR (300 MHz, CD$_3$OD) δ$_H$: 1.10 (s, 6H), 1.99-1.82 (m, 1H), 2.30-2.05 (m, 1H), 3.10-2.93 (m, 1H), 3.29-3.16 (m, 1H), 3.39-3.32 (m, 4H), 3.73 (s, 2H), 6.69 (s, 2H), 7.13 (d, 1H), 7.44-7.34 (m, 3H); MS: [M+H]=303.

EXAMPLE 4

(3S)-N-[(3,5-Dimethylphenyl)methyl]-N-(1-methylethyl)-pyrrolidin-3-amine fumarate $^1$H NMR (300 MHz, CD$_3$OD) δ$_H$: 1.14 (d, 6H), 2.05-1.92 (m, 1H), 2.22-2.11 (m, 1H), 2.34 (s, 6H), 3.16-2.99 (m, 1H), 3.55-3.20 (m, 1H), 3.42-3.32 (m, 4H), 3. 94-3.63. (m, 2H), 6.75 (s, 2H), 6.92 (s, 1H), 7.03 (s, 2H); MS: [M+H]=247.

EXAMPLE 5

(3S)-N-[(3-Chlorophenyl)methyl]-N-(1-methylethyl)-pyrrolidin-3-amine fumarate $^1$H NMR (300 MHz, CD$_3$OD) δ$_H$: 0.87 (dd, 6H), 1.86-1.69 (m, 1H), 2.04-1.94 (m, 1H), 2.96-2.80 (m, 1H), 3.14-3.04 (m, 1H), 3.20-3.17 (m, 4H), 3.59 (s, 2H), 6.56 (s, 2H), 7.11-7.08 (m, 1H), 7.18-7.14 (m, 2H), 7.29 (s, 1H); MS: [M+H]=253/255.

EXAMPLE 6

(3S)-N-[(2,3-Dichlorophenyl)methyl]-N-(1-methylethyl)-pyrrolidin-3-amine fumarate $^1$H NMR (300 MHz, CD$_3$OD) δ$_H$: 1.12 (dd, 6H), 1.96-1.82 (m, 1H), 2.18-2.05 (m, 1H), 3.11-2.98 (m, 1H), 3.27-3.17 (m, 1H), 3.41-3.31 (m, 4H), 3.92 (m, 2H), 6.70 (s, 2H), 7.33 (t, 1H), 7.45 (d, 1H), 7.67 (d, 1H); MS: [M+H]=288.

EXAMPLE 7

(3S)-N-[(2,3-Dimethylphenyl)methyl]-N-(1-methylethyl)-pyrrolidin-3-amine fumarate $^1$H NMR (300 MHz, CD$_3$OD) $\delta_H$: 1.09 (d, 6H), 2.15-1.92 (m, 2H), 2.29 (s, 3H), 3.08-2.96. (m, 1H), 3.26-3.15 (m, 1H), 3.40-3.31 (m, 4H), 3.38-3.67 (m, 2H), 6.70 (s, 2H), 7.03 (dd, 1H), 7.35-7.31 (m, 1H), 7.37-7.32 (m, 1H); MS: [M+H]=247.

EXAMPLE 8

(3S)-N-[(2,4-Dichlorophenyl)methyl]-N-(1-methylethyl)-pyrrolidin-3-amine D-tartrate $^1$H NMR (300 MHz, d6-DMSO) $\delta_H$: 0.92-1.06 (m, 6H), 1.59-1.76 (m, 1H), 1.89-2.02 (m, 1H), 2.78-2.92 (m, 2H), 2.98-3.07 (m, 1H), 3.15-3.28 (m, 2H), 3.60-3.74 (m, 3H), 3.94 (s, 2H), 7.42 (dd, 1H), 7.56 (d, 1H), 7.62 (d, 1H); MS: [M+H]=287/289/291.

The following Examples were similarly prepared as described above for Example 1, by reductive alkylation of 1,1-dimethylethyl (3S)-3-[(cyclohexylmethyl)amino]-pyrrolidine-1-carboxylate with the appropriate substituted benzaldehyde:

EXAMPLE 9

(3S)-N-(Cyclohexylmethyl)-N-[(2-methylphenyl)methyl]-pyrrolidin-3-amine fumarate $^1$H NMR (300 MHz, CD$_3$OD) $\delta_H$: 1.20-0.73 (m, 5H), 1.42-1.34 (m, 1H), 1.88-1.66 (m, 5H), 2.04-1.94 (m, 2H), 2.18-2.08 (m, 2H), 2.33 (d, 2H), 2.48 (s, 3H), 3.24-3.13 (m, 1H), 3.44-3.33 (m, 4H), 3.81-3.48 (m, 2H), 6.70 (s, 2H), 7.15 (t, 1H), 7.43 (d, 1H), 7.46 (m, 2H); MS: [M+H]=287.

EXAMPLE 10

(3S)-N-(Cyclohexylmethyl)-N-{[2-(methylthio)phenyl]-methyl}pyrrolidin-3-amine fumarate $^1$H NMR (300 MHz, CD$_3$OD) $\delta_H$: 0.86-0.69 (s, 3H), 1.22-1.12 (m, 3H), 1.41-1.29 (m, 1H), 1.84-1.67 (m, 5H), 2.16-1.95 (m, 2H), 2.34 (d, 2H), 2.38 (s, 3H), 3.23-3.05 (m, 1H), 3.44-3.28 (m, 4H), 3.78-3.55 (m, 2H), 6.70 (s, 2H), 7.16 (s, 2H), 7.35-7.32 (m, 1H); MS: [M+H]=319.

EXAMPLE 11

(3S)-N-(Cyclohexylmethyl)-N-[(2-fluorophenyl)methyl]-pyrrolidin-3-amine fumarate $^1$H NMR (300 MHz, CD$_3$OD) $\delta_H$: 0.83-0.75 (s, 6H), 1.24-1.17 (m, 3H), 1.48-1.42 (m, 1H), 1.85-1.68 (m, 5H), 2.03-1.92 (m, 1H), 2.17-2.10 (m, 1H), 2.35 (d, 2H), 3.25-3.05 (m, 1H), 3.44-3.32 (m, 4H), 3.81-3.62 (m, 2H), 6.71 (s, 2H), 7.20-7.05 (m, 2H), 7.33-7.27 (m, 1H), 7.47-7.42 (m, 1H); MS: [M+H]=291.

EXAMPLE 12

(3S)-N-(Cyclohexylmethyl)-N-(naphthalene-1-ylmethyl)-pyrrolidin-3-amine fumarate $^1$H NMR (300 MHz, CD$_3$OD) $\delta_H$: 1.20-0.76 (m, 5H), 1.42-1.35 (m, 1H), 1.87-1.65 (m, 5H), 2.17-1.99 (m, 2H), 2.44-2.40 (d, 2H), 3.44-3.07 (m, 4H), 3.68-3.60 (m, 1H), 4.24 (q, 2H), 6.70 (s, 2H), 7.59-7.42 (m, 4H), 7.90-7.81 (m, 2H), 8.29-8.26 (m, 1H); MS: [M+H]=323.

EXAMPLE 13

(3S)-N-[(2-Chlorophenyl)methyl]-N-(cyclohexylmethyl)-pyrrolidin-3-amine fumarate $^1$H NMR (300 MHz, CD$_3$OD) $\delta_H$: 0.89-0.77 (m, 2H), 1.24-1.13 (m, 3H), 1.36 (d, 6H), 1.49-1.42 (m, 1H), 1.83-1.68 (m, 5H), 2.15-1.93 (m, 2H), 2.35 (d, 2H), 3.20-3.06 (m, 1H), 3.33-3.23 (m, 4H), 3.75-3.42 (m, 2H), 4.69-4.61 (m, 1H), 6.70 (s, 2H), 6.98-6.88 (m, 2H), 7.35 (d, 1H), 7.50-7.19 (m, 1H); MS: [M+H]=307.

EXAMPLE 14

(3S)-N-(Cyclohexylmethyl)-N-({2-[1-(methylethyl)oxy]-phenyl}methyl)pyrrolidin-3-amine fumarate $^1$H NMR (300 MHz, CD$_3$OD) $\delta_H$: 0.89-0.77 (m, 2H), 1.24-1.13 (m, 3H), 1.36-1.34 (dd, 6H), 1.49-1.42 (m, 1H), 1.83-1.68 (m, 5H), 1.93 (m, 2H, m), 2.35 (d, 2H), 3.20-3.06 3.20-3.06 (m, 1H), 3.33-3.23 (m, 4H), 3.75-3.42 (m, 2H), 4.69-4.61 (m, 1H), 6.70 (s, 2H), 6.98-6.88 (m, 2H), 7.35 (d, 1H), 7.50-7.19 (m, 1H); MS: [M+H]=331.

The following Examples were similarly-prepared as described above for Example 1, by reductive alkylation of 1,1-dimethylethyl (3S)-3-(cyclopentylamino)pyrrolidine-1-carboxylate with the appropriate substituted benzaldehyde:

EXAMPLE 15

(3S)-N-Cyclopentyl-N-[(2,4-dichlorophenyl)methyl]-pyrrolidin-3-amine di-D-tartrate $^1$H NMR (300 MHz, d6-DMSO) $\delta_H$: 1.19-1.35 (m, 2H), 1.36-1.75 (m, 7H), 1.93-2.06 (m, 1H), 2.81-2.88 (m, 1H), 2.98-3.08 (m, 1H), 3.10-3.31 (m, 3H), 3.62-3.73 (m, 3H), 4.15 (s, 4H), 7.42 (dd, 1H), 7.55 (d, 1H), 7.62 (d, 1H); MS: [M+H]=313/315/317.

EXAMPLE 16

(3S)-N-Cyclopentyl-N-{[2-(trifluoromethyl)phenyl]methyl}-pyrrolidin-3-amine fumarate $^1$H NMR (300 MHz, d6-DMSO) $\delta_H$: 1.20-1.73 (m, 9H), 1.95-2.02 (m, 1H), 2.79-2.86 (m, 1H), 2.96-3.05 (m, 1H), 3.14-3.27 (m, 3H), 3.62-3.73 (m, 1H), 3.81 (s, 2H), 6.46 (s, 2H), 7.39-7.44 (m, 1H), 7.63-7.68 (m, 2H), 7.90-7.92 (m, 1H). MS: [M+H]=313.

EXAMPLE 17

(3S)-N-Cyclopentyl-N-[(3-chlorophenyl)methyl]-pyrrolidin-3-amine fumarate $^1$H NMR (300 MHz, d6-DMSO) $\delta_H$: 1.25-1.70 (m, 9H), 1.90-2.00 (m, 1H), 2.73-2.89 (m, 1H), 2.94-3.04 (m, 1H), 3.11-3.23 (m, 3H), 3.56-3.73 (m, 3H), 6.47 (s, 2H), 7.24-7.36 (m, 4H). MS: [M+H]=279/281.

EXAMPLE 18

(3S)-N-Cyclopentyl-N-[(2-chlorophenyl)methyl]-pyrrolidin-3-amine fumarate $^1$H NMR (300 MHz, d6-DMSO) $\delta_H$: 1.20-1.75 (m, 9H), 1.93-2.03 (m, 1H), 2.81-2.87 (m, 1H), 2.96-3.06 (m, 1H), 3.14-3.27 (m, 3H), 3.63-3.73 (m, 3H), 6.48 (s, 2H), 7.20-7.26 (m, 1H), 7.30-7.39 (m, 2H), 7.60-7.63 (m, 1H). MS: [M+H]=279/281.

EXAMPLE 19

(3S)-N-Cyclopentyl-N-{[4-(trifluoromethyl)phenyl]methyl}-pyrrolidin-3-amine acetate $^1$H NMR (300 MHz, CDCl$_3$) $\delta_H$: 1.25-1.82 (m, 9H), 1.90-2.02 (m, 4H), 2.79-2.86 (m, 1H), 2.95-3.04 (m, 1H), 3.14-3.26 (m, 3H), 3.58-3.69 (m, 1H), 3.73 (s, 2H), 7.44 (d, 2H), 7.53 (d, 2H). MS: [M+H]=313.

EXAMPLE 20

(3S)-N-Cyclopentyl-N-{[2-(methylthio)phenyl]methyl}-pyrrolidin-3-amine $^1$H NMR (300 MHz, CDCl$_3$) $\delta_H$: 1.33-2.02 (m, 10H), 2.45 (s, 3H), 2.81-2.88 (m, 1H), 2.98-3.08 (m, 1H), 3.13-3.30 (m, 3H), 3.58-3.71 (m, 3H), 7.09-7.23 (m, 3H), 7.54-7.57 (m, 1H). MS: [M+H]=291.

EXAMPLE 21

(3S)-N-Cyclopentyl-N-{[3-(trifluoromethyl)phenyl]methyl}-pyrrolidin-3-amine acetate $^1$H NMR (300 MHz, CDCl$_3$) $\delta_H$: 1.28-1.85 (m, 9H), 1.91 (s, 3H), 1.94-2.05 (m, 1H), 2.83-2.89 (m, 1H), 2.98-3.08 (m, 1H), 3.61-3.79 (m, 1H), 3.74 (s, 2H), 7.34-7.59 (m, 4H). MS: [M+H]=313.

EXAMPLE 22

(3S)-N-Cyclopentyl-N-{[5-fluoro-2-(trifluoromethyl)-phenyl]methyl}-pyrrolidin-3-amine $^1$H NMR (300 MHz, CDCl$_3$) $\delta_H$: 1.18-1.91 (m, 10H), 1.97-2.04 (m, 1H), 2.83-2.90 (m, 1H), 3.04-3.32 (m, 4H), 3.62-3.73 (m, 1H), 3.81 (s, 1H), 6.93-6.99 (m, 1H), 7.55-7.66 (m, 2H). MS: [M+H]=331.

EXAMPLE 23

(3S)-N-Cyclopentyl-N-{[2-(difluoromethoxy)phenyl]methyl}-pyrrolidin-3-amine acetate $^1$H NMR (300 MHz, CDCl$_3$) $\delta_H$: 1.35-2.03 (m, 13H), 2.80-2.87 (m, 1H), 2.98-3.07 (m, 1H), 3.16-3.27 (m, 3H), 3.59-3.72 (m, 3H), 6.54 (t, 1H), 7.03-7.05 (m, 1H), 7.15-7.24 (m, 2H), 7.58-7.61 (m, 1H). MS: [M+H]=311.

EXAMPLE 24

(3S)-N-Cyclopentyl-N-{[5-fluoro-2-(trifluoromethyl)-phenyl]methyl}-pyrrolidin-3-amine fumarate $^1$H NMR (300 MHz, d6-DMSO) $\delta_H$: 1.20-1.78 (m, 9H), 1.91-1.96 (m, 1H), 2.78-2.92 (m, 1H), 2.96-3.08 (m, 1H), 3.14-3.35 (m, 3H), 3.65-3.78 (m, 1H), 3.82 (s, 2H), 6.42 (s, 2H), 7.20-7.32 (m, 1H), 7.60-7.81 (m, 2H); MS: [M+H]=331.

EXAMPLE 25

(3S)-N-Cyclopentyl-N-[(2,4-dimethylphenyl)methyl]-pyrrolidin-3-amine fumarate $^1$H NMR (300 MHz, d6-DMSO) $\delta_H$: 1.20-1.78 (m, 9H), 1.91-1.96 (m, 1H), 2.22 (s, 6H), 2.80-2.87 (m, 1H), 2.96-3.05 (m, 1H), 3.14-3.24 (m, 3H), 3.50-3.68 (m, 3H), 3.86 (s, 2H), 6.91-6.96 (m, 2H), 7.30-7.33 (m, 1H). MS: [M+H]=273.

EXAMPLE 26

(3S)-N-Cyclopentyl-N-[(3,5-dimethylphenyl)methyl]-pyrrolidin-3-amine fumarate $^1$H NMR (300 MHz, d6-DMSO) $\delta_H$: 1.20-1.76 (m, 9H), 1.85-2.02 (m, 1H), 2.23 (s, 6H), 2.77-2.84 (m, 1H), 2.93-3.03 (m, 1H), 3.13-3.19 (m, 3H), 3.50-3.62 (m, 3H), 6.43-6.45 (m, 2H), 6.81 (bs, 1H), 6.91 (bs, 2H). MS: [M+H]=273.

EXAMPLE 27

(3S)-N-Cyclopentyl-N-[(2,5-dimethylphenyl)methyl]-pyrrolidin-3-amine fumarate $^1$H NMR (300 MHz, d6-DMSO) $\delta_H$: 1.20-1.78 (m, 9H), 1.85-1.96 (m, 1H), 2.20 (s, 3H), 2.24 (s, 3H), 2.81-2.87 (m, 1H), 2.93-3.02 (m, 1H), 3.13-3.23 (m, 3H), 3.51-3.70 (m, 3H), 6.42-6.44 (m, 2H), 6.88 (d, 1H), 6.97 (d, 1H), 7.26 (s, 1H); MS: [M+H]=273.

EXAMPLE 28

(3S)-N-Cyclopentyl-N-[(2,4-difluorophenyl)methyl]-pyrrolidin-3-amine fumarate

MS: [M+H]=273.

EXAMPLE 29

(3S)-N-Cyclopentyl-N-{[5-fluoro-3-(trifluoromethyl)-phenyl]methyl}-pyrrolidin-3-amine fumarate $^1$H NMR (300 MHz, d6-DMSO) $\delta_H$: 1.20-1.69 (m, 9H), 1.92-2.01 (m, 1H), 2.78-2.85 (m, 1H), 2.93-3.03 (m, 1H), 3.13-3.25 (m, 3H), 3.58-3.69 (m, 1H), 3.80 (s, 2H), 6.42-6.44 (m, 2H), 7.47-7.53 (m, 3H). MS: [M+H]=331.

EXAMPLE 30

(3S)-N-Cyclopentyl-N-[(3-methylphenyl)methyl]-pyrrolidin-3-amine fumarate $^1$H NMR (300 MHz, d6-DMSO) $\delta_H$: 1.20-1.76 (m, 9H), 1.90-1.96 (m, 1H), 2.28 (s, 3H), 2.77-2.84 (m, 1H), 2.93-3.03

(m, 1H), 3.15-3.41 (m, 3H), 3.55-3.67(m, 3H), 6.42-6.44 (m, 2H), 6.98-7.01 (m, 1H), 7.10-7.20 (m, 3H). MS: [M+H]=259.

EXAMPLE 31

(3S)-N-Cyclopentyl-N-[(2,3-dimethylphenyl)methyl]-pyrrolidin-3-amine D-tartrate $^1$H NMR (300 MHz, d6-DMSO) $\delta_H$: 1.33-1.75 (m, 9H), 1.90-1.94 (m, 1H), 2.15 (s, 3H), 2.23 (s, 3H), 2.80-2.87 (m, 1H), 2.96-3.05 (m, 1H), 3.15-3.24 (m, 3H), 3.62-3.67 (m, 3H), 3.84 (s, 2H), 6.98-7.06 (m, 2H), 7.31-7.33 (m, 1H). MS: [M+H]=273.

EXAMPLE 32

(3S)-N-Cyclopentyl-N-[(2,3-dichlorophenyl)methyl]-pyrrolidin-3-amine D-tartrate $^1$H NMR (300 MHz, d6-DMSO) $\delta_H$: 1.20-1.75 (m, 9H), 1.90-2.05 (m, 1H), 2.79-2.86 (m, 1H), 2.97-3.06 (m, 1H), 3.15-3.28 (m, 3H), 3.64-3.76 (m, 3H), 3.84 (s, 2H), 7.34-7.39 (m, 1H), 7.50-7.53 (m, 1H), 7.60-7.62 (m, 1H). MS: [M+H]=313/315/317.

EXAMPLE 33

(3S)-N-Cyclopentyl-N-[(2-chloro-6-fluorophenyl)methyl]-pyrrolidin-3-amine D-tartrate $^1$H NMR (300 MHz, d6-DMSO) $\delta_H$: 1.39-1.70 (m, 8H), 1.91-1.96 (m, 2H), 3.01-3.19 (m, 4H), 3.24-3.32 (m, 1H), 3.56-3.67 (m, 1H), 3.78 (s, 2H), 3.87 (s, 2H), 7.17-7.24 (m, 1H), 7.30-7.41 (m, 2H). MS: [M+H]=297/299.

EXAMPLE 34

(3S)-N-Cyclopentyl-N-[(3,5-difluorophenyl)methyl]-pyrrolidin-3-amine D-tartrate $^1$H NMR (300 MHz, d6-DMSO) $\delta_H$: 1.30-1.69 (m, 9H), 1.95-2.00 (m, 1H), 2.78-2.85 (m, 1H), 2.96-3.06 (m, 1H), 3.11-3.27 (m, 3H), 3.56-3.70 (m, 3H), 3.87 (s, 2H), 7.01-7.05 (m, 3H). MS: [M+H]=281.

EXAMPLE 35

(3S)-N-Cyclopentyl-N-[(3,5-dichlorophenyl)methyl]-pyrrolidin-3-amine D-tartrate $^1$H NMR (300 MHz, d6-DMSO) $\delta_H$: 1.15-1.74 (m, 9H), 1.90-2.02 (m, 1H), 2.77-2.84 (m, 1H), 2.97-3.06 (m, 1H), 3.11-3.27. (m, 3H), 3.55-3.69 (m, 3H), 3.89 (s, 2H), 7.36 (d, 2H), 7.43 (d, 1H). MS: [M+H]=313/315.

EXAMPLE 36

(3S)-N-Cyclopentyl-N-{[2-chloro-3-(trifluoromethyl)-phenyl]methyl}-pyrrolidin-3-amine D-tartrate $^1$H NMR (300 MHz, d6-DMSO) $\delta_H$: 1.20-1.72 (m, 9H), 1.96-2.04 (m, 1H), 2.82-2.89 (m, 1H), 2.98-3.07 (m, 1H), 3.16-3.31 (m, 3H), 3.69-3.75 (m, 1H), 3.83 (s, 2H), 3.93 (s, 2H), 7.53-7.58 (m, 1H), 7.72-7.75 (m, 1H), 7.94-7.97 (m, 1H). MS: [M+H]=347/349.

The following Examples were similarly prepared as described above for Example 1, by reductive alkylation of 1,1-dimethylethyl (3S)-3-(propylamino)pyrrolidine-1-carboxylate with the appropriate substituted benzaldehyde:

EXAMPLE 37

(3S)-N-[2-Chlorophenyl)methyl]-N-propylpyrrolidin-3-amine fumarate $^1$H NMR (300 MHz, CD$_3$OD) $\delta_H$: 0.75 (t, 3H), 1.32-1.45 (m, 2H), 1.82-1.95 (m, 1H), 2.01-2.12 (m, 1H), 2.42-2.47 (m, 2H), 3.00-3.34 (m, 4H), 3.55 (quintet, 1H), 3.71 (q, 2H), 6.58 (s, 2H), 7.11-7.28 (m, 3H), 7.47 (d,d, 1H); MS: [M+H]=253/255.

EXAMPLE 38

(3S)-N-Propyl-N-{[2-(trifluoromethyl)phenyl]methyl}-pyrrolidin-3-amine, D-tartrate $^1$H NMR (300 MHz, CD$_3$OD): $\delta_H$ 7.97-7.92(d, 1H), 7.68-7.59 (m, 2H), 7.44-7.42(t, 1H), 4.41 (s, 2H), 3.96-3.82 (AB, 2H), 3.69-3.59 (m, 1H), 3.45-3.3.37 (m, 2H), 3.29-3.2 (m, 1H), 3.15-3.08 (m, 1H), 2.59-2.54 (m, 2H), 2.18-2.09 (m, 1H), 2.03-1.89 (m, 1H), 1.55-1.43 (m, 2H), 0.90-0.85 (t, 3H); MS: [M+H]=287.

Title compound was also prepared by Method B of Example 199 substituting step d) with the following procedure:

Into a vessel equiped with a refrigerator, a thermometer and a magnetic stirrer, was placed (3S)-N-Propyl-N-{[2-(trifluoromethyl)phenyl]methyl}-pyrrolidin-3-amine (10 g, 34 mmol, 1 eq.), isopropanol (Roland tech. grade 150 ml) and D-tartaric acid (Acros 99%, 5.24 g, 34 mmol, 1 eq.). The mixture was heated at 70° C. for 5 minutes until it became homogenous, cooled slowly in an oil bath and agitated for 72 h at room temperature. The mixture was filtered on frosted glass P3 and washed twice with 25 ml isopropyl alcohol (Roland) to afford 16.48 g of humid cake. Drying overnight under vacuum at 45° C. yielded 12.7 g of the title compound as a white salt.

EXAMPLE 39

(3S)-N-{5-Fluoro-2-(trifluoromethyl)phenyl]methyl}-N-propylpyrrolidin-3-amine, D-tartrate $^1$H NMR (300 MHz, CD$_3$OD) $\delta_H$: 0.91 (t, 3H), 1.45-1.58 (m, 2H), 1.90-2.03 (m, 1H), 2.13-2.23 (m, 1H), 2.57-2.62 (m, 2H), 3.10-3.17 (m, 1H), 3.22-3.30(m, 1H), 3.40-3.48 (m, 2H), 3.68 (quintet, 1H), 3.91 (q, 2H), 4.43 (s, 2H), 7.17 (t,d, 1H), 7.70-7.87 (m, 2H); MS: [M+H]=305.

The following Examples were similarly prepared as described above for Example 1, by reductive alkylation of 1,1-dimethylethyl (3S)-3-(cyclobutylamino)pyrrolidine-1-carboxylate with the appropriate substituted benzaldehyde:

EXAMPLE 40

(3S)-N-Cyclobutyl-N-{[5-fluoro-2-(trifluoromethyl)-phenyl]methyl}-pyrrolidin-3-amine D-tartrate $^1$H NMR (300 MHz, d6-DMSO) $\delta_H$: 1.41-2.04 (m, 8H), 2.82-2.89 (m, 1H), 2.98-3.07 (m, 1H), 3.16-3.30 (m, 2H), 3.33-3.43 (m, 1H), 3.51-3.62 (m, 1H), 3.71-3.92 (m, 4H), 7.24-7.31 (td, 1H), 7.66-7.79 (m, 2H); MS: [M+H]=317,

EXAMPLE 41

(3S)-N-Cyclobutyl-N-[(2,3-dichlorophenyl)methyl]-pyrrolidin-3-amine L-tartrate

MS: [M+H]=299/301/303.

The following Examples were similarly prepared as described above for Example 1, by reductive alkylation of 1,1-dimethylethyl (3S)-3-(cyclohexylamino)pyrrolidine-1-carboxylate with the appropriate substituted benzaldehyde:

EXAMPLE 42

(3S)-N-Cyclohexyl-N-[(3-methylphenyl)methyl]-pyrrolidin-3-amine D-tartrate $^1$H NMR (300 MHz, d6-DMSO) $\delta_H$: 0.99-1.39 (m, 5H), 1.51-1.54 (m, 1H), 1.60-1.78 (m, 5H), 1.91-1.97 (m, 1H), 2.28 (s, 3H), 2.36-2.42 (m, 1H), 2.77-2.83 (m, 1H), 2.97-3.06 (m, 1H), 3.14-3.24 (m, 2H), 3.59-3.71 (m, 3H), 3.96 (s, 2H), 6.99-7.02 (m, 1H), 7.12-7.21 (m, 3H); MS: [M+H]=273.2.

EXAMPLE 43

(3S)-N-Cyclohexyl-N-{[2-(methylthio)phenyl]methyl}-pyrrolidin-3-amine di-D-tartrate $^1$H NMR (300 MHz, d6-DMSO) $\delta_H$: 0.90-1.28 (m, 5H), 1.51-1.54 (m, 1H), 1.62-1.84 (m, 5H), 1.87-2.02 (m, 1H), 2.30-2.47 (m, 4H), 2.84-2.90 (m, 1H), 2.96-3.10 (m, 1H), 3.13-3.28 (m, 2H), 3.63-3.82 (m, 3H), 4.10 (s, 4H), 7.11-7.17 (m, 1H), 7.24 (d, 2H), 7.49 (d, 1H); MS: [M+H]=305.

EXAMPLE 44

(3S)-N-Cyclohexyl-N-{[2-(trifluoromethyl)phenyl]methyl}-pyrrolidin-3-amine D-tartrate $^1$H NMR (300 MHz, d6-DMSO) $\delta_H$: 0.95-1.27 (m, 5H), 1.52 (d, 1H), 1.59-1.78 (m, 5H), 1.90-2.03 (m, 1H), 2.38 (t, 1H), 2.83 (t, 1H), 2.96-3.10 (m, 1H), 3.15-3.27 (m, 2H), 3.66-3.90 (m, 5H), 7.43 (t, 1H), 7.61-7.70 (m, 2H), 7.91 (d, 1H); MS: [M+H]=327.

EXAMPLE 45

(3S)-N-Cyclohexyl-N-{[3-(trifluoromethylthio)phenyl]-methyl}-pyrrolidin-3-amine D-tartrate $^1$H NMR (300 MHz, d6-DMSO) $\delta_H$: 0.95-1.35 (m, 5H), 1.521-1.54 (m, 1H), 1.60-1.80 (m, 5H), 1.89-2.02 (m, 1H), 2.33-2.40 (m, 1H), 2.79-2.83 (m, 1H), 2.96-3.10 (m, 1H), 3.15-3.28 (m, 2H), 3.65-3.85 (m, 3H), 4.00 (s, 2H), 7.44-7.60 (m, 3H), 7.69 (s, 1H); MS: [M+H]=359.

EXAMPLE 46

(3S)-N-Cyclohexyl-N-[(2,4-dichlorophenyl)methyl]-pyrrolidin-3-amine di-D-tartrate $^1$H NMR (300 MHz, d6-DMSO) $\delta_H$: 1.05-1.25 (m, 5H), 1.51-1.55 (m, 1H), 1.62-1.77 (m, 5H), 1.90-2.02 (m, 1H), 2.32-2.45 (m, 1H), 2.80-2.86 (m, 1H), 2.96-3.09 (m, 1H), 3.15-3.29 (m, 2H), 3.68-3.82 (m, 3H), 4.09 (s, 4H), 7.42 (dd, 1H), 7.56 (d, 1H), 7.62 (d, 1H); MS: [M+H]=327/329.

EXAMPLE 47

(3S)-N-Cyclohexyl-N-[(3,5-dichlorophenyl)methyl]-pyrrolidin-3-amine sesqui-D-tartrate $^1$H NMR (300 MHz, d6-DMSO) $\delta_H$: 1.05-1.25 (m, 5H), 1.51-1.55 (m, 1H), 1.60-1.76 (m, 5H), 1.89-2.03 (m, 1H), 2.34-2.46 (m, 1H), 2.76-2.83 (m, 1H), 2.95-3.09 (m, 1H), 3.15-3.27 (m, 2H), 3.61-3.75,(m, 3H), 4.03 (s, 3H), 7.36-7.37 (m, 2H), 7.40-7.45 (m, 1H); MS: [M+H]=327/329/331.

EXAMPLE 48

(3S)-N-Cyclohexyl-N-[(2,3-dichlorophenyl)methyl]-pyrrolidin-3-amine L-tartrate

MS: [M+H]=327/329/331.

The following Examples were similarly prepared as described above for Example 1, by reductive alkylation of 1,1-dimethylethyl (3S)-3-(2-methoxy-1-methylethyl amino) pyrrolidine-1-carboxylate with the appropriate substituted benzaldehyde:

EXAMPLE 49

(3S)-N-[(2,4-Dichlorophenyl)methyl]-N-(2-methoxy-1methylethyl)pyrrolidin-3-amine D-tartrate $^1$H NMR (300 MHz, d6-DMSO) $\delta_H$: 0.98 (t, 3H), 1.59-1.77 (m, 1H), 1.86-2.04 (m, 1H), 2.75-3.07 (m, 3H), 3.10-3.38 (m, 7H), 3.65-3.90 (m, 5H), 3.43 (dd, 1H), 7.53-7.58 (m, 1H), 7.65 (dd, 1H); MS: [M+H]=317/319.

EXAMPLE 50

(3S)-N-[(2-Chloro-4-fluorophenyl)methyl]-N-(2-methoxy-1-methylethyl)pyrrolidin-3-amine D-tartrate $^1$H NMR (300 MHz, d6-DMSO) $\delta_H$: 0.98 (t, 3H), 1.61-1.79 (m, 1H), 1.85-2.04 (m, 1H), 2.77-3.06 (m, 3H), 3.10-3.39 (m, 7H), 3.65-3.93 (m, 5H), 7.22 (td, 1H), 7.38 (dd, 1H), 7.60-7.39 (m, 1H); MS: [M+H]=301.

EXAMPLE 51

(3S)-N-[(3,5-Dichlorophenyl)methyl]-N-(2-methoxy-1-methylethyl)pyrrolidin-3-amine D-tartrate $^1$H NMR (300 MHz, d6-DMSO) $\delta_H$: 0.90-1.00 (m, 3H), 1.57-1.75 (m, 1H), 1.85-2.03 (m, 1H), 2.73-3.07 (m, 3H), 3.10-3.37 (m, 7H), 3.59-3.94 (m, 5H), 7.41 (dd, 3H); MS: [M+H]=317/319.

EXAMPLE 52

(3S)-N-[(2,3-Dichlorophenyl)methyl]-N-(2-methylpropyl)-pyrrolidin-3-amine L-tartrate To a solution of 1,1-dimethylethyl (3S)-3-(2-methylpropyl amino)-pyrrolidine-1-carboxylate (see Example 197(a)) (0.363 g, 1.5 mmol) in 1,2-dichloroethane (10 mL) was added 2,3-dichloro-benzaldehyde (1.05 g, 6.0 mmol), followed by sodium triacetoxyborohydride (0.95 g, 4.5 mmol), and the mixture left to stir for 16 h. The reaction mixture was quenched with water (5 mL) and 2N sodium hydroxide (5 mL), and the organic layer separated by passing through a hydrophobic frit. The organic solution was diluted with methanol (5 mL) and absorbed onto an Isolute™ SCX-2 ion exchange cartridge (5 g), washed with methanol (15 mL) and the product eluted with 2M ammonia in methanol solution (15 mL). The solvent was removed in vacuo to give 1,1-dimethylethyl (3S)-3-{[(2,3-dichlorophenyl)methyl](2-methylpropyl)amino}pyrrolidine-1-carboxylate as a colourless oil. This was taken up in dichloromethane (2 mL), trifluoroacetic acid (1.4 mL, 18.3 mmol) added, and the mixture stirred at room temperature for 16 h. The solvent was removed in vacuo and the residue diluted with methanol (5 mL) and absorbed onto an Isolute™ SCX-2 ion exchange cartridge (5 g). The column was washed with methanol (15 mL) and the product eluted with 2M ammonia in methanol solution (15 mL). The solvent was removed in vacuo and the residue purified by mass guided preparative LCMS. The residue was diluted with methanol (5 mL) and again absorbed onto an Isolute™ SCX-2 ion exchange cartridge (5 g). The column was washed with methanol (15 mL), the product eluted with 2M ammonia solution (15 mL) and the solvent removed in vacuo. The desired compound product was taken up in cyclohexane (15 mL) and a hot solution of L-tartaric acid (1 equiv.) in isopropanol (1 mL) was added. The solvent was removed in vacuo and the residue taken up in 40% acetonitrile/water and freeze dried to give the tile compound as a white solid.

$^1$H NMR $\delta_H$ (300 MHz, CD$_3$OD): 7.43 (1H, dd), 7.34 (1H, dd), 7.19 (1H, t), 4.28 (2H, s), 3.78-3.67 (2H, s), 3.60-3.49 (1H, m), 3.33-3.26 (2H, m), 3.15-2.97 (2H, m), 2.31-2.19 (2H, m), 2.07-1.97 (1H, m), 1.92-1.78 (1H, m), 1.54 (1H, septet), 0.76 (6H, d); MS: [M+1]=301/303/305.

EXAMPLE 53

(3S)-N-{[2-Chloro-4-fluorophenyl]methyl}-N-(1-methylethyl)pyrrolidin-3-amine L-tartrate a) 1,1-Dimethylethyl (3S)-3-((1-methylethyl)-{[2-chloro-4-fluorophenyl]methyl}amino)pyrrolidine-1-carboxylate.

To a solution of 1,1-dimethylethyl (3S)-3-[(1-methylethyl)amino]-pyrrolidine-1-carboxylate (0.5 g, 2.19 mmol) and 2-chloro-4-fluorobenzaldehyde (1.23 g, 4.38 mmol) in dichloroethane (15 mL) at room temperature under a nitrogen atmosphere was added portionwise sodium triacetoxyborohydride (1.16 g, 5.48 mmol). The reaction was stirred at room temperature for 72 hours. After this time analysis showed that some starting material was still present so an additional equivalent of the benzaldehyde and sodium triacetoxyborohydride was added, and the reaction stirred overnight. Starting material was still evident therefore a further equivalent of both benzaldehyde and sodium triacetoxyborohydride was added, together with DMF (2 mL). After 16 h all remaining starting material had disappeared. The reaction was evaporated to dryness in vacuo. The resulting residue was dissolved in methanol and absorbed onto a cationic ion exchange resin (Isolute™ SCX-2). The basic components were recovered from the column by elution with 7N ammonia in methanol. This solution was concentrated in vacuo to yield the desired compound as an oil. This was used directly in the next step without further purification.

b) (3S)-N-{[2-Chloro-4-fluorophenyl]methyl}-N-(1-methylethyl)pyrrolidin-3-amine L-tartrate.

1,1-Dimethylethyl (3S)-3-((1-methylethyl)-{[2-chloro-4-fluorophenyl]methyl}amino)pyrrolidine-1-carboxylate (0.81 g, 2.19 mmol) was dissolved in a mixture of dichloromethane and trifluoroacetic acid (15 mL, 1:1) and stirred at room temperature for 2 h. The reaction solution was concentrated in vacuo and re-dissolved in MeOH. This solution was absorbed onto a cationic ion exchange resin (Isolute™ SCX-2). The basic components were isolated by elution with 7N ammonia in methanol and evaporated in vacuo. The residue was dissolved in hot isohexane (5 mL) and to this was added an equimolar amount of L-tartaric acid, dissolved in a minimal amount of hot isopropanol. The solution was evaporated in vacuo to yield the title compound as a solid.

$^1$H NMR (300 MHz, CD$_3$OD) $\delta_H$: 7.59-7.54 (m, 1H), 7.09-7.00 (m, 1H), 6.99-6.94 (m, 1H), 4.29 (s, 2H), 3.74-3.63 (m, 3H), 3.19-3.06 (m, 1H), 2.94-2.85 (m, 2H), 2.05-1.95 (m, 1H), 1.84-1.71 (m, 1H), 0.98 (d, 3H), 0.96 (d, 3H),MS: [M+H]=271.

The following Examples were similarly prepared from 1,1-dimethylethyl (3S)-3-[(1-methylethyl)amino]-pyrrolidine-1-carboxylate, by reductive alkylation with the appropriately substituted benzaldehyde and subsequent deprotection, as described above for Example 53:

EXAMPLE 54

(3S)-N-{[4-Fluoro-2-(trifluoromethyl)phenyl]methyl}-N-(1-methylethyl)-pyrrolidin-3-amine L-tartrate $^1$H NMR (300 MHz, CD$_3$OD) $\delta_H$: 8.04-7.99 (m, 1H), 7.44-7.36 (m, 2H), 4.40 (s, 2H), 3.87 (s, 2H), 3.82-3.74 (m, 1H), 3.37-3.36 (m, 2H), 3.31-3.18 (m, 1H), 3.05-2.96 (m, 2H), 2.14-2.09 (m, 1H), 1.94-1.80 (m, 1H), 1.0 (m, 6H); MS: [M+H]=305.

EXAMPLE 55

(3S)-N-{[2-Fluoro-4-(trifluoromethyl)phenyl]methyl}-N-(1-methylethyl)-pyrrolidin-3-amine L-tartrate $^1$H NMR (300 MHz, CD$_3$OD) $\delta_H$: 7.77-7.66 (m, 1H), 7.39-7.37 (m, 1H), 7.30-7.26 (m, 1H), 4.29 (s, 2H), 3.74 (s, 2H), 3.72-3.64 (m, 1H), 3.30-3.22 (m, 2H), 3.19-3.07 (m, 1H), 2.97-2.86 (m, 2H), 2.06-2.00 (m, 1H), 1.99-1.72 (m, 1H), 0.98 (m, 6H); MS: [M+H]=305.

EXAMPLE 56

(3S)-N-[(3 4-Dichlorophenyl)methyl]-N-(1-methylethyl)-pyrrolidin-3-amine fumarate $^1$H NMR (300 MHz, CD$_3$OD) $\delta_H$: 1.10 (d, 3H), 1.10 (d, 3H), 1.80-1.94 (m, 1H), 2.07-2.15 (m, 1H), 2.93-3.06 (m, 2H), 3.15-3.39 (m, 3H), 3.66-3.80 (m, 3H), 6.70 (s, 2H), 7.32 (d,d, 1H), 7.47(d, 1H), 7.56 (d, 1H); MS: [M+H]=287/289/291.

EXAMPLE 57

(3S)-N-[(3,5-Dichlorophenyl)methyl]-N-(1-methylethyl)-pyrrolidin-3-amine fumarate $^1$H NMR (300 MHz, CD$_3$OD) $\delta_H$: 1.08 (d, 3H), 1.11 (d, 3H), 1.79-1.93 (m, 1H), 2.08-2.18 (m, 1H), 2.93-3.05 (m, 2H), 3.16-3.25 (m, 1H), 3.30-3.40 (m, 2H), 3.67-3.81 (m, 3H), 6.70 (s, 2H), 7.30 (t, 1H), 7.37 (m, 2H); MS: [M+H]= 287/289/291.

EXAMPLE 58

(3S)-N-[(4-Chlorophenyl)methyl]-N-(1-methylethyl)-pyrrolidin-3-amine fumarate $^1$H NMR (300 MHz, CD$_3$OD) δ$_H$: 1.08 (d, 3H), 1.10 (d, 3H), 1.83-1.96 (m, 1H), 2.06-2.14 (m, 1H), 2.92-3.06 (m, 2H), 3.15-3.38 (m, 3H), 3.64-3.79 (m, 3H), 6.70 (s, 2H), 7.30-7.39 (m, 4H); MS: [M+H]=253/255.

EXAMPLE 59

(3S)-N-[(3-Methoxyphenyl)methyl]-N-(1-methylethyl)-pyrrolidin-3-amine fumarate $^1$H NMR (300 MHz, CD$_3$OD) δ$_H$: 1.08 (d, 3H), 1.10(d, 3H), 1.83-1.96 (m, 1H), 2.06-2.14 (m, 1H), 2.92-3.06 (m, 2H), 3.15-3.38 (m, 3H), 3.64-3.79 (m, 3H), 6.70 (s, 2H), 7.30-7.39 (m, 4H); MS: [M+H]=249.

EXAMPLE 60

(3S)-N-[(3-Cyano-4-fluorophenyl)methyl]-N-(1-methylethyl)-pyrrolidin-3-amine fumarate $^1$H NMR (300 MHz, CD$_3$OD) δ$_H$: 1.08 (d, 3H), 1.10 (d, 3H), 1.80-1.94 (m, 1H), 2.08-2.12 (m, 1H), 2.94-3.06 (m, 2H), 3.16-3.26 (m, 1H), 3.31-3.40 (m, 2H), 3.71-3.82 (m, 3H), 6.69 (s, 2H), 7.30-7.35 (m, 1H), 7.72-7.78 (m, 2H); MS: [M+H]=262.

EXAMPLE 61

(3S)-N-[(2,3-Dimethylphenyl)methyl]-N-(1-methylethyl)-pyrrolidin-3-amine D-tartrate $^1$H NMR (300 MHz, CD$_3$OD) δ$_H$: 1.09 (d, 6H), 2.15-1.92 (m, 2H), 2.29 (s, 3H), 3.08-2.96 (m, 1H), 3.26-3.15 (m, 1H), 3.40-3.31 (m, 4H), 3.38-3.67 (m, 2H), 6.70 (s, 2H), 7.03 (dd, 1H), 7.35-7.31 (m, 1H), 7.37-7.32 (m, 1H); MS: [M+H]=247.

EXAMPLE 62

(3S)-N-{[(2-Chloro-3-(trifluoromethyl)phenyl]methyl}-N-(1-methylethyl)-pyrrolidin-3-amine D-tartrate $^1$H NMR (300 MHz, d6-DMSO) δ$_H$: 0.97-1.01 (m, 6H), 1.60-1.74 (m, 1H), 1.92-2.02 (m, 1H), 2.82-2.93 (m, 2H), 2.98-3.08 (m, 1H), 3.19-3.27 (m, 2H), 3.65-3.79 (m, 1H), 3.82 (s, 2H), 3.93 (s, 2H), 7.54-7.59 (m, 1H), 7.73-7.75 (m, 1H), 7.94-7.96 (m, 1H). MS: [M+H]=321/323.

EXAMPLE 63

(3S)-N-[(2-Chloro-6-fluorophenyl)methyl]-N-(1-methylethyl)-pyrrolidin-3-amine D-tartrate

MS: [M+H]=271/273.

EXAMPLE 64

(3S)-N-[(2,4-Chlorophenyl)methyl]-N-(1-methylethyl)-pyrrolidin-3-amine L-tartrate $^1$H NMR (300 MHz, d6-DMSO) δ$_H$: 0.92-1.06 (m, 6H), 1.59-1.76 (m, 1H), 1.89-2.02 (m, 1H), 2.78-2.92 (m, 2H), 2.98-3.07 (m,1H), 3.15-3.28 (m, 2H), 3.60-3.74 (m, 3H), 3.94 (s, 2H), 7.42 (dd, 1H), 7.56 (d, 1H), 7.62 (d, 1H); MS: [M+H]=287/289/291.

EXAMPLE 65

(3S)-N-{[2-(4-Fluorophenoxy)phenyl]methyl}-N-(1-methylethyl)-pyrrolidin-3-amine L-tartrate

MS: [M+H]=329.

EXAMPLE 66

(3S)-N-{[2-(3,4-Difluorophenoxy)phenyl]methyl}-N-(1-methylethyl)-pyrrolidin-3-amine L-tartrate

MS: [M+H]=347.

EXAMPLE 67

(3S)-N-{(4'-Fluoro-[1,1'-biphenyl]-2-yl)methyl}-N-(1-methylethyl)-pyrrolidin-3-amine L-tartrate

MS: [M+H]=313.

The following Examples were prepared by reductive alkylation of the appropriately substituted 1,1-dimethylethyl (3S)-3-(benzylamino)pyrrolidine-1-carboxylate (see Preparations 10 to 15 above) with the appropriate aldehyde and subsequent deprotection, as described for Example 52:

EXAMPLE 68

(3S)-N-{[4-Fluoro-2-(trifluoromethyl)phenyl]methyl}-N-propylpyrrolidin-3-amine L-tartrate $^1$H NMR (300 MHz, CD$_3$OD) δ$_H$: 7.98-7.93 (m, 1H), 7.46-7.36 (m, 2H), 4.88(s, 1H), 3.92-3.79 (q, 2H), 3.79-3.58 (quin, 1H), 3.45-3.33 (m, 2H), 3.31-3.20 (m, 1H), 3.14-3.07 (m, 1H), 2.57-2.52 (q, 2H), 2.20-2.12 (m, 1H), 1.99-1.89 (m, 1H), 1.55-1.42 (quin, 2H), 0.90-0.85 (t, 3H); MS: [M+H]=305.

EXAMPLE 69

(3S)-N-Butyl-N-{[4-fluoro-2-(trifluoromethyl)phenyl]-methyl}pyrrolidin-3-amine L-tartrate $^1$H NMR (300 MHz, CD$_3$OD) δ$_H$: 7.98-7.93 (m, 1H), 7.46-7.36 (m, 2H), 4.88(s, 1H), 3.92-3.79 (q, 2H), 3.79-3.58 (quin, 1H), 3.45-3.38 (m, 2H), 3.31-3.20 (m, 1H), 3.14-3.07 (m, 1H), 2.61-2.56 (q, 2H), 2.20-2.12 (m, 1H), 2.09-1.89 (m, 1H), 1.50-1.40 (m, 2H), 1.36-1.24 (m, 2H), 0.91-0.86 (t, 3H); MS: [M+H]=319.

EXAMPLE 70

(3S)-N-Cyclopropylmethyl-N-{[4-fluoro-2-(trifluoromethyl)phenyl]-methyl}pyrrolidin-3-amine L-tartrate $^1$H NMR (300 MHz, CD$_3$OD) δ$_H$: 7.95-7.90 (d, 1 m), 7.36-7.27 (m, 2H), 4.32 (s, 2H), 3.94-3.85 (q, 2H), 3.80-3.67 (quin, 1H), 3.37-3.27 (m, 2H), 3.23-3.14 (m, 1H), 3.05-3.01 (m, 1H), 2.40(d, 2H), 2.11-2.06 (m, 1H), 1.93-1.83 (m, 1H), 8.80-0.78 (m, 1H), 0.40-0.37(d, 2H), 0.01-0.003 (d, 2H); MS: [M+H]=317.

EXAMPLE 71

(3S)-N-[(3,5-Dichlorophenyl)methyl]-N-propylpyrrolidin-3-amine L-tartrate $^1$H NMR (300 MHz, CD$_3$OD) δ$_H$: 7.24-7.21 (m, 3H), 4.76(s, 1H), 3.65-3.50 (m, 3H), 3.34-3.26 (m, 2H), 3.19-3.12 (m, 1H), 3.10-2.95 (m, 1H), 2.43-2.38 (q, 2H), 2.07-2.01 (m, 1H), 1.89-1.79 (m, 1H), 1.42-1.32 (m, 2H), 0.79-0.74 (t, 3H); MS: [M+H]=287.

EXAMPLE 72

(3S)-N-Butyl-N-[(3,5-dichlorophenyl)methyl]pyrrolidin-3-amine L-tartrate $^1$H NMR (300 MHz, CD$_3$OD) δ$_H$: 7.24-7.21 (m, 3H), 4.76 (s, 1H), 3.65-3.51 (m, 3H), 3.48-3.27 (m, 2H), 3.20-3.12 (m, 1H), 3.08-2.95 (m, 1H), 2.46-2.42 (q, 2H), 2.07-1.99 (m, 1H), 1.87-1.76 (m, 1H), 1.39-1.30 (m, 2H), 1.25-1.18 (m, 2H), 0.87-0.78 (t, 3H); MS: [M+H]=301/303/305.

EXAMPLE 73

(3s)-N-Cyclopropylmethyl-N-[(3,5-dichlorophenyl)methyl]pyrrolidin-3-amine L-tartrate $^1$H NMR (300 MHz, CD$_3$OD) δ$_H$: 7.29 (s, 2H), 7.23 (s, 1H), 4.32 (s, 2H), 3.78-3.63 (m, 3H), 3.38-3.21 (m, 2H), 3.18-3.11 (m, 1H), 3.11-3.0 (m, 1H), 2.37 (d, 2H), 2.13-2.08 (m, 1H), 1.94-1.84 (m, 1H), 0.80-0.77 (m, 1H), 0.43-0.40 (d, 2H), 0.03 (d, 2H); MS: [M+H]=299.

EXAMPLE 74

(3S)-N-[(2,4-Dichlorophenyl)methyl]-N-propylpyrrolidin-3-amine L-tartrate $^1$H NMR (300 MHz, CD$_3$OD) δ$_H$: 7.45 (d, 1H, J=8.29 Hz), 7.32 (d, 1H, J=2.26 Hz), 7.25 (dd, 1H, J=2.07 Hz, 6.22 Hz, 2.07 Hz), 4.76 (s, 2H), 3.74-3.61 (q, 2H), 3.59-3.48 (quin, 1H), 3.34-3.22 (m, 2H), 3.18-3.11 (m, 1H), 3.09-2.98 (m, 1H), 2.45-2.40 (m, 2H), 2.10-2.00 (m, 1H), 1.92-1.79 (m, 1H), 1.43-1.31 (m, 2H), 0.77-0.72 (m, 3H); MS: [M+H]=287/289/291.

EXAMPLE 75

(3S)-N-Butyl-N-[(2,4-dichlorophenyl)methyl]pyrrolidin-3-amine L-tartrate $^1$H NMR (300 MHz, CD$_3$OD) δ$_H$: 7.46 (d, 1H), 7.33 (d, 1H), 7.23 (dd, 1H), 4.30 (s, 2H), 3.74-3.61 (q, 2H), 3.56-3.48 (quin, 1H), 3.3-3.27 (m, 2H), 3.16-3.09 (m, 1H), 3.05-2.98 (m, 1H), 2.49-2.44 (m, 2H), 2.08-1.92 (m, 1H), 1.89-1.79 (m, 1H), 1.38-1.28 (m, 2H), 1.23-1.05 (m, 2H), 0.79-0.74 (m, 3H); MS: [M+H]=301/303/305.

EXAMPLE 76

(3S)-N-Cyclopropylmethyl-N-[(2,4-dichlorophenyl)methyl]pyrrolidin-3-amine L-tartrate $^1$H NMR (300 MHz, CD$_3$OD) δ$_H$: 7.58 (d, 1H), 7.35 (d, 1H), 7.25 (dd, 1H), 4.32 (s, 2H), 3.88-3.67(m, 3H), 3.38-3.28 (m, 2H), 3.22-3.12 (m, 1H), 3.08-3.02 (m, 1H), 2.40 (d, 2H), 2.14-2.06 (m, 1H), 1.96-1.86 (m, 1H), 0.81-0.77 (m, 1H), 0.39 (d, 2H), 0.01-0.002 (d, 2H); MS: [M+H]=299.

EXAMPLE 77

(3S)-N-[(2-Chloro4-fluorophenyl)methyl]-N-propylpyrrolidin-3-amine L-tartrate $^1$H NMR (300 MHz, CD$_3$OD) δ$_H$: 7.51-7.46 (m, 1H), 7.11-7.00 (m, 1H), 6.98-6.94 (m, 1H), 4.77 (s, 2H), 3.74-3.59 (q, 2H), 3.59-3.48 (quin, 1H), 3.33-3.27 (m, 2H), 3.18-3.09 (m, 1H), 3.06-2.99 (m, 1H), 2.45-2.40 (m, 2H), 2.08-2.00 (m, 1H), 1.93-1.80 (m, 1H), 1.43-1.31 (m, 2H), 0.86-0.72 (m, 3H); MS: [M+H]=271.

EXAMPLE 78

(3S)-N-Butyl-N-[(2-chloro-4-fluorophenyl)methyl]-pyrrolidin-3-amine L-tartrate $^1$H NMR (300 MHz, CD$_3$OD) δ$_H$: 7.51-7.46 (m, 1H), 7.11-7.00 (m, 1H), 6.98-6.94 (m, 1H), 4.76 (s, 2H), 3.74-3.60 (q, 2H), 3.56-3.51 (quin, 1H), 3.32-3.26 (m, 2H), 3.16-3.09 (m, 1H), 3.06-2.99 (m, 1H), 2.48-2.43 (m, 2H), 2.09-2.03 (m, 1H), 1.94-1.83 (m, 1H), 1.39-1.29 (m, 2H), 1.23-1.13 (m, 2H), 0.79-0.74 (m, 3H); MS: [M+H]=285.

EXAMPLE 79

(3S)-N-[(2-Chloro-4-fluorophenyl)methyl]-N-(cyclolpropylmethyl)pyrrolidin-3-amine L-tartrate $^1$H NMR (300 MHz, CD$_3$OD) δ$_H$: 7.60-7.55 (m, 1H), 7.13-7.09 (m, 1H), 7.03-6.96 (m 1H), 4.33 (s, 2H), 3.87-3.67 (m, 3H), 3.38-3.28 (m, 2H), 3.22-3.15 (m, 1H), 3.09-3.03 (m, 1H), 2.39 (d, 2H), 2.14-2.08 (m, 1H), 1.90-1.87 (m, 1H), 0.80-0.72 (m, 1H), 0.40 (d, 2H), 0.011-0.002 (d, 2H); MS: [M+H]=283.

EXAMPLE 80

(3S)-N-{[4-Fluoro-2-(trifluoromethyl)phenyl]methyl}-N-(tetrahydro-2H-thiopyran-4-yl)pyrrolidin-3-amine L-tartrate a) 1,1-Dimethylethyl (3S)-3-[(tetrahydro-2H-thio-pyran-4-yl)amino]pyrrolidine-1-carboxylate.

Neat tetrahydro-4H-thiopyran-4-one (4.2 g, 36 mmol) and 1,1-dimethylethyl (3S)-3-aminopyrrolidine-1-carboxylate (6.73 g, 36 mmol) were stirred together in ethanol for 16 h. Sodium borohydride (2.74 g, 72 mmol) was added portionwise. The reaction was then quenched with water and the solvent removed in vacuo. The residue was dissolved in water and the solution extracted with dichloromethane. The combined organics were dried (Na$_2$SO$_4$), filtered and evaporated in vacuo to provide the title compound as an oil.

$^1$H NMR (300 MHz, CDCl$_3$) δ$_H$: 3.69-3.48 (m, 3H), 3.46-3.31 (m, 1H), 2.98-2.80 (m, 1H), 2.75-2.74 (m, 1H), 2.67-2.64 (m, 3H), 2.58-2.50 (m, 1H), 2.46-2.20 (m, 3H), 2.19-2.14 (m, 1H), 1.77-1.65 (m, 2H), 1.56-1.48 (m, 2H), 1.45 (s, 9H).

b) (3S)-N-{[4-Fluoro-2-(trifluoromethyl)phenyl]methyl}-N-(tetrahydro-2H-thiopyran-4-yl)pyrrolidin-3-amine L-tartrate.

1,1-Dimethylethyl (3S)-3-[(tetrahydro-2H-thio-pyran-4-yl)amino]pyrrolidine-1-carboxylate was reductively alkylated with 4-fluoro-2-(trifluoromethyl)benzaldehyde and deprotected, as described above for Example 52. ¹H NMR (300 MHz, CD₃OD) δ$_H$: 7.99-7.94 (m, 1H), 7.46-7.36 (m, 2H), 4.40 (s, 2H), 3.94-3.81 (m, 3H), 3.42-3.21 (m, 3H), 3.19-2.97 (m, 1H), 2.50-2.49 (m, 5H), 2.28-2.20 (m, 3H), 1.97-1.90 (m, 1H), 1.75-1.62 (m, 2H); MS: [M+H]=363.

The following example was prepared as described above for Example 80 substituting the appropriate benzaldehyde.

EXAMPLE 81

(3S)-N-[(2,4-Dichlorophenyl)methyl]-N-(tetrahydro-2H-thiopyran-4-yl)pyrrolidin-3-amine L-tartrate ¹H NMR (300 MHz, CD₃OD) δ$_H$: 7.50 (d, 1H), 7.33 (d, 1H), 7.23 (dd, 1H), 4.32 (s, 2H), 3.82-3.77 (m, 2H), 3.26-3.10 (m, 2H), 2.93-2.86 (m, 1H), 2.56-2.53 (m, 4H), 2.38-2.34 (m, 1H), 2.09-1.99 (m, 3H), 1.83-1.80 (m, 1H), 1.59-1.53 (m, 2H), MS: [M+H]=345/347/349.

EXAMPLE 82

(3S)-N-[(2,4-Dichlorophenyl)methyl]-N-(1,1-di-oxido-tetrahydro-2H-thiopyran -4-yl)pyrrolidin-3-amine L-tartrate a) 1,1-Dimethylethyl (3S)-3-[[(2,4-dichlorophenyl)-methyl](1,1-dioxidotetrahydro-2H-thiopyran-4-yl)amino]pyrrolidine-1-carboxylate.

To a ice cold solution of 1,1-dimethylethyl (3S)-3-[[(2,4-dichlorophenyl)-methyl](2H-thiopyran-4-yl)-amino]pyrrolidine-1-carboxylate (0.675 g, 1.5 mmol) in ethyl acetate (5 mL) was added dropwise peracetic acid solution (35% in acetic acid) (0.77 mL, 3.7 mmol) and left to stir for 30 min. The reaction mixture was absorbed onto a cationic ion exchange resin (Isolute™ SCX-2). The basic components were recovered from the column by elution with 7N ammonia in methanol. The eluate was concentrated in vacuo and the resultant product taken onto the next step without further purification.

b) (3S)-N-[(2,4-Dichlorophenyl)methyl]-N-(1,1-dioxido-tetrahydro-2H-thiopyran-4-yl)pyrrolidin-3-amine L-tartrate.

1,1-Dimethylethyl (3S)-3-[[(2,4-dichlorophenyl)-methyl](1,1-dioxidotetrahydro-2H-thiopyran-4-yl)amino]pyrrolidine-1-carboxylate was deprotected in trifluoroacetic acid/dichloromethane (1:1) and purified, as described above in Example 54. ¹H NMR (300 MHz, CD₃OD) δ$_H$: 7.50-7.49 (m, 1H), 7.42-7.40 (m, 1H), 7.26-7.23 (m, 1H), 4.27 (s, 2H), 3.86-3.72 (m, 1H), 3.35-2.97 (m, 5H), 2.94-2.90 (m, 2H), 2.82-2.75 (m, 1H), 2.30-2.21 (m, 2H), 2.06-1.98 (m, 4H), 1.85-1.82 (m, 1H); MS: [M+H]=377/379/381.

EXAMPLE 83

(3S)-N-{[5-Fluoro-2-(trifluoromethyl)phenyl]methyl}-N-(tetrahydro-2H-pyran-4-yl)pyrrolidin-3-amine D-tartrate a) 1,1-Dimethylethyl (3S)-3-[(tetrahydro-2H-pyran-4-yl)amino]pyrrolidine-1-carboxylate.

Neat tetrahydro-4H-pyran-4-one (18.7 g, 100 mmol) and 1,1-dimethylethyl (3S)-3-aminopyrrolidine-1-carboxylate (26.1 g, 140.1 mmol) were stirred together for 20 minutes prior to addition of anhydrous dichloroethane (140 mL). The solution was then cooled to 0° C. under nitrogen and stirred as sodium triacetoxyborohydride (59.2 g, 281 mmol) was added portionwise. The reaction was allowed to warm to room temperature and stirred for 5 days, after which the reaction solution was carefully poured onto ice-cold aqueous sodium hydrogen carbonate solution. The phases were separated and the aqueous phase washed with dichloromethane. The combined organic phases were dried (MgSO₄) and concentrated in vacuo. The crude product was purified by automated flash chromatography on silica, eluting with methanol in ethyl acetate (0:100 to 30:70), to provide the title compound as an off-white solid. ¹H NMR (300 MHz, d6-DMSO) δ$_H$: 1.13-1.29 (m, 2H), 1.39 (s, 9H), 1.55-1.65 (m, 1H), 1.68-1.81 (m, 2H), 1.87-2.00 (m, 1H), 2.64 (sep, 1H), 2.91 (sex, 1H), 3.10-3.45 (m, 6H), 3.81 (dt, 2H). MS: [M+H]=271, [M+H-tBu]=215.

b) (3S)-N-{[5-Fluoro-2-(trifluoromethyl)phenyl]methyl}-N-(tetrahydro-2H-pyran-4-yl)pyrrolidin-3-amine D-tartrate.

To a stirred solution of 1,1-dimethylethyl (3S)-3-[(tetrahydro-2H-pyran-4-yl)amino]pyrrolidine-1-carboxylate (1.12 g, 4.2 mmol) and 5-fluoro-2-(trifluoromethyl)benzaldehyde (4.56 g, 23.8 mmol) in anhydrous dichloroethane (50 mL) was added portionwise sodium triacetoxyborohydride (3.86 g, 18.3 mmol). The reaction mixture was stirred at room temperature under nitrogen and the reaction progress was followed by MS. After 2 days more reagents were added: 5-fluoro-2-(trifluoromethyl)benzaldehyde (0.98 g, 5.1 mmol) and sodium triacetoxyborohydride (3.00 g, 14.2 mmol), and after a further 2 days the reaction was found to be complete. The reaction solution was carefully poured onto ice-cold saturated aqueous sodium hydrogen carbonate solution and filtered through a PTFE hydrophobic frit. The organic phase was concentrated in vacuo and the residue redissolved in methanol. The methanolic solution was filtered through a cationic ion exchange resin (Isolute™ SCX-2) and the basic components isolated by elution with 2N ammonia in methanol. After concentrating in vacuo, the residue was redissolved in dichloromethane/trifluoro-acetic acid (2:1) and allowed to stir at room temperature for 4 hours. The reaction mixture was concentrated in vacuo and redissolved in methanol. The methanolic solution was filtered through a cationic ion exchange resin (Isolute™ SCX-2) and the basic components isolated by elution with 2N ammonia in methanol. The crude product was purified by UV guided prep-LC, and the desired compound collected from the acidic prep-LC mobile phase via a cationic ion exchange resin, as described above. The basic product was dissolved in hot cyclohexane and to this was added an equimolar amount of D-tartaric acid dissolved in a minimal amount of hot isopropanol. The solution was allowed to cool overnight, and the next day the resultant solid was filtered off and dried in vacuo, to yield the title compound as a white crystalline solid. ¹H NMR (300 MHz, d6-DMSO) δ$_H$: 1.40-1.80 (m, 5H), 1.91-2.06 (m, 1H), 2.61-2.74 (m, 1H), 2.81-2.93 (dd, 1H), 2.97-3.11 (dt, 1H), 3.12-3.31 (m, 4H), 3.69-3.96 (m, 7H), 7.49-7.61 (m, 2H), 7.90-7.99 (m, 1H). MS: [M+H]=347.

The following Examples were similarly prepared from 1,1-dimethylethyl (3S)-3-[(tetrahydro-2H-pyran-4-yl)amino]pyrrolidine-1-carboxylate and the appropriate benzaldehyde, as described above for Example 83:

EXAMPLE 84

(3S)-N-{[2-(Trifluoromethyl)phenyl]methyl}-N-(tetrahydro-2H-pyran-4-yl)pyrrolidin-3-amine hemi-D-tartrate ¹H NMR (300 MHz, d6-DMSO) δ$_H$: 1.35-1.75 (m, 5H), 1.90-2.04 (m,1H), 2.63-2.75 (m, 1H), 2.76-2.86 (m, 1H), 2.94-3.03 (m, 1H), 3.10-3.25 (m, 4H), 3.67-3.90 (m, 6H), 7.43 (t, 1H), 7.66 (t, 2H), 7.92 (d, 1H); MS: [M+H]=329.

EXAMPLE 85

(3S)-N-[(2,4-Dichlorophenyl)methyl]-N-(tetrahydro-2H-pyran-4-yl)pyrrolidin-3-amine D-tartrate $^1$H NMR (300 MHz, d6-DMSO) $\delta_H$: 1.35-1.75 (m, 5H), 1.91-2.04 (m, 1H), 2.62-2.75 (m, 1H), 2.78-2.85 (m, 1H), 2.91-3.04 (m, 1H), 3.13-3.27 (m, 4H), 3.67-3.90 (m, 7H), 7.42 (dd, 1H), 7.52-7.58 (m, 1H), 7.63 (d, 1H); MS: [M+H]=329/331.

EXAMPLE 86

(3S)-N-[(3.5-Dichlorophenyl)methyl]-N-(tetrahydro-2H-pyran-4-yl)pyrrolidin-3-amine di-D-tartrate $^1$H NMR (300 MHz, d6-DMSO) $\delta_H$: 1.35-1.75 (m, 5H), 1.93-2.06 (m, 1H), 2.63-2.76 (m, 1H), 2.79-2.86 (m,1H), 2.96-3.09 (m, 1H), 3.15-3.30 (m, 4H), 3.64-3.90 (m, 5H), 4.04 (s, 4H), 7.37 (m, 2H), 7.43-7.44 (m, 1H); MS: [M+H]=329/331.

EXAMPLE 87

(3S)-N-[(2-Chloro-4-fluorophenyl)methyl]-N-(tetrahydro-2H-pyran-4-yl)pyrrolidin-3-amine D-tartrate $^1$H NMR (300 MHz, d6-DMSO) $\delta_H$: 1.35-1.77 (m, 5H), 1.92-2.05 (m, 1H), 2.60-2.75 (m, 1H), 2.81-2.88 (m, 1H), 2.95-3.08 (m, 1H), 3.19-3.29 (m, 4H), 3.68-3.90 (m, 7H), 7.18-7.25 (m, 1H), 7.38-7.41 (m, 1H), 7.60-7.65 (m, 1H); MS: [M+H]=313/315.

EXAMPLE 88

(3S)-N-[(4-Chloro-2-methylphenyl)methyl]N-(tetrahydro-2H-pyran-4-yl)pyrrolidin-3-amine sesqui-D-tartrate $^1$H NMR (300 MHz, d6-DMSO) $\delta_H$: 1.40-1.81 (m, 5H), 1.89-2.03 (m, 1H), 2.28 (s, 3H), 2.59-2.74 (m, 1H), 2.82-2.88 (m, 1H), 2.94-3.07 (m, 1H), 3.12-3.29 (m, 4H), 3.62-3.90 (m, 5H), 3.98 (s, 3H), 7.16-7.24 (m, 2H), 7.42-7.50 (m, 1H); MS: [M+H]=309/311.

EXAMPLE 89

(3S)-N-[(2,3-Dichlorophenyl)methyl]-N-(tetrahydro-2H-pyran-4-yl)pyrrolidin-3-amine L-tartrate $^1$H NMR $\delta_H$ (300 MHz, CD$_3$OD): 7.53 (1H, dd), 7.32 (1H, dd), 7.19 (1H, t), 4.32 (2H, s), 3.88-3.80 (5H, m), 3.31-3.20 (4H, m) 3.17-3.07 (1H, m), 2.95-2.88 (1H, m), 2.78-2.67 (1H, m), 2.09-1.98 (1H, m), 1.88-1.72 (1H, m), 1.66-1.44 (4H, m); MS: [M+1]=329.

EXAMPLE 90

(3S)-N-[(2-Chloro-6-fluorophenyl)methyl]-N-(tetrahydro-2H-pyran-4-yl)pyrrolidin-3-amine D-tartrate

MS: [M+H]=313/315.

EXAMPLE 91

(3S)-N-{[4-Fluoro-2-(trifluoromethyl)phenyl]methyl}-N-(tetrahydro-2H-pyran-4-yl)pyrrolidin-3-amine D-tartrate $^1$H NMR (300 MHz, d6-DMSO) $\delta_H$: 1.40-1.80 (m, 5H), 1.91-2.06 (m, 1H), 2.61-2.74 (m, 1H), 2.81-2.93 (m, 1H), 2.97-3.11 (m, 1H), 3.12-3.31 (m, 4H), 3.69-3.96 (m, 7H), 7.49-7.61 (m, 2H), 7.90-7.99 (m, 1H). MS: [M+H]=347.

EXAMPLE 92

(3S)-N-([1,1'-Biphenyl]-2-ylmethyl)-N-(tetrahydro-2H-pyran-4-yl)pyrrolidin-3-amine L-tartrate

MS: [M+H]=337.

EXAMPLE 93

(3S)-N-{(4-Fluoro-[1,1'-biphenyl]-2-yl)methyl}-N-(tetrahydro-2H-pyran-4-yl)pyrrolidin-3-amine L-tartrate

MS: [M+H]=355.

EXAMPLE 94

(3S)-N-[(2-Chlorophenyl)methyl]-N-(tetrahydro-2H-pyran-4-yl)pyrrolidin-3-amine L-tartrate

MS: [M+H]=295/297.

EXAMPLE 95

(3S)-N-[(2-Chloro-5-fluorophenyl)methyl]-N-(tetrahydro-2H-pyran-4-yl)pyrrolidin-3-amine D-tartrate

MS: [M+H]=313/315.

EXAMPLE 96

(3S)-N-[(4-Fluorophenyl)methyl]-N-(tetrahydro-2H-pyran-4-yl)pyrrolidin-3-amine L-tartrate

MS: [M+H]=279.

EXAMPLE 97

(3S)-N-{[5-Fluoro-2-(trifluoromethyl)phenyl]methyl}-N-(tetrahydro-2H-pyran-4-yl)pyrrolidin-3-amine L-tartrate a) 1,1-Dimethylethyl (3S)-3-[(tetrahydro-2H-pyran-4-yl)amino]pyrrolidine-1-carboxylate.

To neat 1,1-dimethylethyl (3S)-3-aminopyrrolidine-1-carboxylate (300 g, 1.61 mol) was added dropwise tetrahydro-4H-pyran-4-one (165 g, 1.65 mol) over 15 min. During the addition, the mixture temperature increased from 23 to 33° C. It was post-stirred for 1 hour at room temperature. This mixture was placed in a Parr hydrogenator bottle and ethanol (1.25L) and Pd/C 5% 50% wet (type 440 from Johnson & Johnson) were added. The mixture was purged three times with nitrogen followed by three times with hydrogen. After the purge, the hydrogenation was performed under a pressure of 40 psi for 3 h. During the first hour, the mixture temperature increased from 22 to 37° C. followed by a decrease to room temperature. After 3 h of reaction, hydrogen pressure was removed and the mixture was purged with nitrogen. The suspension was filtered under a nitrogen atmosphere through wet celite which was washed with ethanol (500 ml). The filtrate was concentrated at 40° C. under reduced pressure to give 440 g of yellow oil. The residual ethanol was removed by azeotropic distillation with toluene (2×250 ml) to obtain 445 g of the title compound.

b) 1,1-Dimethylethyl (3S)-3-({[5-fluoro-2-(trifluoromethyl) phenyl]methyl}-(tetrahydro-2H-pyran-4-yl)amino]pyrrolidine-1-carboxylate.

Into a 20L glass reactor was introduced 1,1-dimethylethyl (3S)-3-[(tetrahydro-2H-pyran-4-yl)amino]pyrrolidine-1-carboxylate (350 g, 1.295 mol), 2-trifluoromethyl-5-fluorobenzaldehyde (500 g, 2.6 mol) and DMSO (3.5L). To this solution was added sodium triacetoxyborohydride in 3 portions (560 g, 2.64 mol). This suspension was post-stirred for 3 days at room temperature. Then, this mixture was quenched dropwise with water (3.5L) over 2 h maintaining the temperature between 20 and 28° C. The mixture was post-stirred for 1 h to ensure a complete quench. Toluene (7L) was added and an aqueous solution of NaOH 10M was used to extract the final product into the organic phase at pH 9-10. The organic phase was dried over $MgSO_4$, filtered and washed with toluene (700 ml). The filtrate was concentrated at 40° C. under reduced pressure to give 965 g of crude product containing 50.4% w/w of the title compound.

c) (3S)-N-{[5-fluoro-2-(trifluoromethyl)phenyl]methyl}-N-(tetrahydro-2H-pyran-4-yl)amino]pyrrolidine-3-amine.

A glass reactor of 20L was charged with crude 1,1-dimethylethyl (3S)-3-({[5-fluoro-2-(trifluoromethyl)phenyl]methyl}-(tetrahydro-2H-pyran-4-yl)amino]pyrrolidine-1-carboxylate (950 g: 50.4% w/w, 1.064 mol) and methanol (4.75L). To this solution was added dropwise an aqueous solution of fuming HCl (37%) between 22 and 27° C. The mixture was heated at reflux for 2 h until the end of gas emission and was cooled down to 20° C. It was quenched with an aqueous solution of NaOH 10M (350 ml) until pH 7 and methanol was removed at 40° C. under reduced pressure to give orange oil. This oil was shared into toluene (9.5L) and an aqueous solution of HCl (1M) to eliminate the impurities in the organic phase. To the aqueous phase was added an aqueous solution of NaOH 10M (600 ml) until the pH reached 10-12 and the final product was then extracted in toluene (9.5L). A second extraction with toluene (4L) was necessary to completely extract the final product. The assembled organic phases were dried over $MgSO_4$, filtered and washed with toluene (1L). The filtrate was concentrated at 40° C. under reduced pressure to give 381 g of oil containing 90% w/w of the title compound.

d) (3S)-N-{[5-fluoro-2-(trifluoromethyl)phenyl]methyl}-N-(tetrahydro-2H-pyran-4-yl)amino]pyrrolidine-3-amine L-tartrate.

A glass reactor of 10L was charged with the crude (3S)-N-{[5-fluoro-2-(trifluoromethyl)phenyl]methyl}-N-(tetrahydro-2H-pyran-4-yl)amino]pyrrolidine-3-amine (375 g:90% w/w; 0.97 mol) and acetonitrile (3.3L). To this solution was added the L-(+)-tartaric acid (150 g, 0.99 mol) to form a suspension. It was heated at reflux to obtain an orange solution at 65° C. and crystallization began at 75° C. After 35 min of heating reflux was reached (81.5° C.) and was maintained during 10 min. Then, the mixture was cooled down at room temperature for 1 h and was post-stirred for 1 h. The suspension was filtered and the crystals were rinsed with acetonitrile (0.33L). The white crystals were dried at 40° C. under reduced pressure to give 482 g of the title compound.

$^1$H NMR (300 MHz, d6-DMSO) $\delta_H$: 1.40-1.80 (m, 5H), 1.91-2.06 (m, 1H), 2.61-2.74 (m, 1H), 2.81-2.93 (dd, 1H), 2.97-3.11 (dt, 1H), 3.12-3.31 (m, 4H), 3.69-3.96 (m, 7H), 7.49-7.61 (m, 2H), 7.90-7.99 (m, 1H); MS: [M+H]=347.

EXAMPLE 98

(3S)-N-(1-Methylethyl)-N-{[2-(trifluoromethyl)-5-fluorophenyl]methyl}pyrrolidin-3-amine fumarate a) 1,1-Dimethylethyl (3S)-3-((1-methylethyl)-{[2-(trifluoromethyl)-5-fluorophenyl]methyl}amino)-pyrrolidine-1-carboxylate.

A solution of 1,1-dimethylethyl (3S)-3-[(1-methylethyl) amino]pyrrolidine-1-carboxylate (0.34 g, 1.5 mmol) and 2-(trifluoromethyl)-5-fluorobenzyl bromide (0.58 g, 2.25 mmol) in acetonitrile (5 mL) was heated at reflux with anhydrous potassium carbonate (0.41 g, 3 mmol) for 24 hours. The reaction mixture was cooled, diluted with ethyl acetate and washed with water. The organic extracts were washed with brine, dried ($MgSO_4$), filtered and evaporated in vacuo to give an oil. This was purified by flash chromatography on silica, eluting with ethyl acetate/cyclohexane (0:100 to 10:90), to give the title compound as an oil.

b) (3S)-N-(1-Methylethyl)-N-{[2-(trifluoromethyl)-5-fluorophenyl]methyl}pyrrolidin-3-amine fumarate.

A solution of 1,1-dimethylethyl (3S)-3-((1-methylethyl)-{[2-(trifluoromethyl)-5-fluorophenyl]-methyl}amino)-pyrrolidine-1-carboxylate (0.26 g) in a mixture of trifluoroacetic acid (2 mL), dichloromethane (8 mL) and water (0.2 mL) was stirred at room temperature for 3 hours. The reaction mixture was evaporated in vacuo. The crude mixture was taken up in methanol and absorbed onto an SCX-2 ion exchange cartridge. After initially washing with methanol, the product was eluted with 2M methanolic ammonia and the collected fractions evaporated in vacuo. The crude product was taken up in methanol and fumaric acid (1 equiv.) in methanol added. The solvent was removed in vacuo and the resultant gum triturated with diethyl ether. The solid formed was filtered off and dried in vacuo at 50° C. to yield the title compound as an off-white microcrystalline solid. $^1$H NMR (300 MHz, $CD_3OD$) $\delta_H$: 1.09 (d, 3H), 1.10 (d, 3H), 1.87 (m, 1H), 2.15 (m, 1H), 3.01 (m, 2H), 3.23 (m, 1H), 3.38 (m, 2H), 3.81 (m, 1H), 3.91 (s, 2H), 6.70 (s, 2H), 7.15 (dt, 1H), 7.73 (m, 2H); MS: [M+H]=305.

The following Examples were similarly prepared as described for Example 98, using the appropriate substituted benzyl bromide in step a) above:

EXAMPLE 99

(3S)-N-(1-Methylethyl)-N-{[3-(trifluoromethyl)phenyl]-methyl}pyrrolidin-3-amine fumarate $^1$H NMR (300 MHz, $CD_3OD$) $\delta_H$: 1.10 (d, 3H), 1.11(d, 3H), 1.89 (m, 1H), 2.13 (m, 1H), 3.00 (m, 2H), 3.21 (m, 1H), 3.36 (m, 2H), 3.78 (m, 1H), 3.82 (s, 2H), 6.70 (s, 2H), 7.48-7.54 (m, 2H), 7.63-7.71 (m, 2H); MS: [M+H]=287.

EXAMPLE 100

(3S)-N-(1-Methylethyl)-N-{[4-(trifluoromethyl)phenyl]-methyl}pyrrolidin-3-amine fumarate $^1$H NMR (300 MHz, $CD_3OD$) $\delta_H$: 1.10 (d, 3H), 1.11 (d, 3H), 1.89 (m, 1H), 2.12 (m, 1H), 3.00 (m, 2H), 3.20 (m, 1H), 3.33 (m, 2H), 3.77 (m, 1H), 3.81 (s, 2H), 6.70 (s, 2H), 7.58 (d, 2H), 7.62 (d, 2H); MS: [M+H]=287.

EXAMPLE 101

(3S)-N-([1,1'-Biphenyl]-2-ylmethyl)-N-(1-methylethyl)-pyrrolidin-3-amine fumarate $^1$H NMR (300 MHz, CD$_3$OD) $\delta_H$: 0.95 (d, 6H), 1.75 (m, 1H), 1.91 (m, 1H), 2.75 (dd, 1H), 2.93 (sept, 1H), 3.10 (m, 2H), 3.25 (m, 1H), 3.60 (m, 3H), 6.70 (s, 2H), 7.17 (dd, 1H), 7.25-7.48 (m, 7H), 7.67 (d, 1H); MS: [M+H]=295.

EXAMPLE 102

(3S)-N-(1-Methylethyl)-N-{[2-phenyloxy)phenyl]methyl}-pyrrolidin-3-amine fumarate $^1$H NMR (300 MHz, CD$_3$OD) $\delta_H$: 1.03 (d, 3H), 1.04 (d, 3H), 1.87-2.11 (m, 2H), 2.99-3.09 (m, 2H), 3.14-3.37 (m, 3H), 3.56-3.81 (m, 3H), 6.70 (s, 2H), 6.86-6.93 (m, 3H), 7.08(t, 1H), 7.15-7.28 (m, 2H), 7.31-7.38 (m, 2H), 7.62 (dd, 1H); MS: [M+H]=311.

EXAMPLE 103

(3S)-N-(1-Methylethyl)-N-{[2-(phenylmethyl)phenyl]-methyl}pyrrolidin-3-amine fumarate

MS: [M+H]=309.

EXAMPLE 104

(3S)-N-[[(2,4-Dichlorophenyl)methyl]-N-(2,2,2-trifluoroethyl)amino]pyrrolidin-3-amine D-tartrate a) 1,1-Dimethylethyl (3S)-3-{[(2,4-dichloro-phenyl)methyl]amino}pyrrolidine-1-carboxylate.

A solution of 2,4-dichlorobenzaldehyde (4.67 g, 26 mmol) and 1,1-dimethylethyl (3S)-3-aminopyrrolidine-1-carboxylate (5 g, 26 mmol) in dry methanol (104 mL) under nitrogen atmosphere, was stirred at room temperature for 14 hours. The aldimine in methanol was carefully treated with solid sodium borohydride (1.58 g, 41.6 mmol). The reaction mixture was stirred for 10 minutes, then quenched with an saturated aqueous solution of sodium hydrogen carbonate (50 mL). Volatiles were removed in vacuo, and the residue taken up in a mixture of water and dichloromethane (100 mL, 1:1). The phases were separated and the aqueous layer further extracted with dichloromethane (3×50 mL). The combined organic extracts were dried (MgSO$_4$) and concentrated to dryness in vacuo. The resulting yellow oil was used in the next step without further purification. $^1$H NMR (300 MHz, CDCl$_3$) $\delta_H$: 1.45 (s, 9H), 1.66-1.76 (m, 1H), 1.98-2.09 (m, 1H), 3.07-3.21 (m, 1H), 3.28-3.58 (m, 4H), 3.84 (s, 2H), 7.20-7.27 (m, 1H), 7.32-7.37 (m, 2H). MS:[M+H]=345/347/349 (3:2).

b) 1,1-Dimethylethyl (3S)-3-[[(2,4-dichlorophenyl)-methyl](trifluoroacetyl)amino]pyrrolidine-1-carboxylate.

To a solution of 1,1-dimethylethyl (3S)-3-{[(2,4-dichlorophenyl)methyl]amino}pyrrolidine-1-carboxylate (2 g, 5.8 mmol) in dry dichloromethane (33 mL) under nitrogen was added successively triethylamine (1.61 mL, 11.6 mmol), trifluoroacetic anhydride (0.99 mL, 6.95 mmol) and N,N-dimethyl-4-aminopyridine (0.35 g,. 2.9 mmol). The resulting mixture was stirred at room temperature for 30 minutes, then quenched with a saturated aqueous solution of sodium hydrogen carbonate (20 mL). The two phases were separated and the aqueous phase further extracted with dichloromethane (3×20 mL). The combined organic extracts were dried (MgSO$_4$) and concentrated in vacuo. The resulting residue was purified by flash chromatography on silica, eluting with ethyl acetate in n-heptane (0:100 to 50:50). This yielded the title compound as a colourless oil. MS: [M+Na]=463/465/467.

c) 1,1-Dimethylethyl (3S)-3-[[(2,4-dichlorophenyl)-methyl](2,2,2-trifluoroethyl)amino]pyrrolidine-1-carboxylate.

Neat borane-dimethylsulfide complex (1.31 mL, 16.3 mmol) was added dropwise to an ice-cold solution of 1,1-dimethylethyl (3S)-3-[[(2,4-dichlorophenyl)-methyl]-(trifluoroacetyl)amino]pyrrolidine-1-carboxylate (2.4 g, 5.44 mmol) in dry tetrahydrofuran (50 mL) under nitrogen. The resulting solution was then heated under reflux for 3 hours. After cooling to room temperature the reaction was carefully poured into a saturated aqueous solution of sodium hydrogen carbonate (200 mL). The suspension was extracted with dichloromethane (3×200 mL), and the combined organic extracts were dried (MgSO$_4$) and evaporated in vacuo. The resulting residue was purified by flash chromatography on silica, eluting with ethyl acetate in n-heptane (0:100 to 50:50), to yield the title compound as a colourless oil. $^1$H NMR (300 MHz, CDCl$_3$) $\delta_H$: 1.44 (s, 9H), 1.72-1.86 (m, 1H), 1.99-2.08 (m, 1H), 3.09-3.23 (m, 4H), 3.42-3.60 (m, 3H), 3.95 (s, 2H), 7.23-7.28 (m, 1H), 7.35-7.37 (m, 1H), 7.43-7.48 (m, 1H).

d) (3S)-N-[[(2,4-Dichlorophenyl)methyl]-N-(2,2,2-trifluoroethyl)amino]pyrrolidin-3-amine D-tartrate.

1,1-Dimethylethyl (3S)-3-[[(2,4-dichlorophenyl)-methyl](2,2,2-trifluoroethyl)amino]pyrrolidine-1-carboxylate (1.4 g, 3.3 mmol) was dissolved in a mixture of dichloromethane and trifluoroacetic acid (10 mL, 2:1), and stirred at room temperature for 30 minutes. The reaction mixture was then concentrated in vacuo and redissolved in methanol. This solution was filtered through a cationic ion exchange resin (Isolute™ SCX-2) and the basic fractions isolated by elution with 2N ammonia in methanol. After evaporation in vacuo the residue (1.09 g) was dissolved in hot cyclohexane (5 mL) and to this was added an equimolar quantity of D-tartaric acid (0.49 g) dissolved in a minimal amount of hot isopropanol. The solution was evaporated in vacuo to yield the title compound as a solid. $^1$H NMR (300 MHz, d6-DMSO) $\delta_H$: 1.68-1.81 (m, 1H), 2.01-2.11 (m, 1H), 2.90-3.05 (m, 2H), 3.23-3.33 (m, 2H), 3.42-3.63 (m, 3H), 3.92-3.93 (m, 4H), 7.44-7.47 (m, 1H), 7.52-7.55 (m, 1H), 7.59-7.60 (m, 1H). MS: [M+H]=327/329/331.

The following Examples were similarly prepared as described above for Example 104:

EXAMPLE 105

(3S)-N-[[(3,5-Dichlorophenyl)methyl]-N-(2,2,2-trifluoroethyl)amino]pyrrolidin-3-amine D-tartrate $^1$H NMR (300 MHz, d6-DMSO) $\delta_H$: 1.65-1.79 (m, 1H), 2.00-2.10 (m, 1H), 2.87-3.05 (m, 2H), 3.23-3.32 (m, 2H), 3.42-3.61 (m, 3H), 3.86 (s, 2H), 3.95 (s, 2H), 7.37-7.38 (m, 2H), 7.50-7.51 (m, 1H). MS: [M+H]=327/329/331.

EXAMPLE 106

(3S)-N-[{[2-(Trifluoromethyl)phenyl]methyl}-N-(2,2,2-trifluoroethyl)amino]pyrrolidin-3-amine D-tartrate $^1$H NMR (300 MHz, d6-DMSO) $\delta_H$: 1.66-1.80 (m, 1H), 1.98-2.06 (m, 1H), 2.88-3.03 (m, 2H), 3.21-3.27 (m, 2H), 3.49-3.57 (m, 3H), 3.88 (s, 2H), 4.04 (s, 2H), 7.46-7.51 (m, 1H), 7.68-7.73 (m, 2H), 7.79-7.81 (m, 1H). MS: [M+H]=327.

EXAMPLE 107

(3S)-N-[[(2,3-Dichlorophenyl)methyl]-N-(2,2,2-trifluoroethyl)amino]pyrrolidin-3-amine L-tartrate

MS: [M+H]=327/329/331.

EXAMPLE 108

(3S)-N-[[(2-Chloro-3-methylphenyl)methyl]-N-(2,2,2-trifluoroethyl)amino]pyrrolidin-3-amine L-tartrate

MS: [M+H]=307/309.

EXAMPLE 109

Methyl ((3S)-pyrrolidin-3-yl{[2-(trifluoromethyl)phenyl]-methyl}amino)acetate D-tartrate 60% Sodium hydride oil dispersion (39 mg, 0.95 mmol) was added to 1,1-dimethylethyl (3S)-3-({[2-(trifluoromethyl)-phenyl]methyl}amino)pyrrolidine-1-carboxylate (250 mg, 0.73 mmol) in DMF (5 mL). After heating at 50° C. for 1 hour under nitrogen, methyl bromoacetate (123 mg, 0.73 mmol) was added. After heating overnight at 50° C. overnight, excess water was added and the product was extracted into ether. The ether was washed with water, dried (MgSO$_4$) and evaporated in vacuo to give an oil (460 mg). The oil was dissolved in dichloromethane (5 mL) and trifluoroacetic acid (0.5 mL) was added. After stirring for 1 day, the solution was evaporated in vacuo to give an oil. The oil was purified using preparative LCMS to give the product as the acetate salt, which was converted to the free base by absorption onto a cationic ion exchange resin (Isolute™ SCX-2) and eluting the basic fractions with 2N ammonia in methanol. The resultant oil was converted to the D-tartaric acid salt (crystallised from ethanol/diethyl ether) to give the title compound as a white solid. $^1$H NMR(300 MHz, CD$_3$OD) $\delta_H$: 1.84-196 (m, 1H), 2.06-2.14 (m, 1H), 3.06-3.37 (2×m,6H), 3.57 (s, 3H), 3.77-3.86 quin,1H), 3.91-4.06 (q, 2H), 4.29 (s, 2H), 7.32-7.36 (t, 1H), 7.49-7.54 (t, 1H), 7.56-7.59 (d, 1H), 7.76-7.89 (d, 1H); MS: [M+H]=317.

The following Examples were prepared from 1,1-dimethylethyl (3S)-3-aminopyrrolidine-1-carboxylate or 1,1-dimethylethyl (3R)-3-aminopyrrolidine-1-carboxylate by initial reductive alkylation with 2-methylpropanaldehyde as described above for Example 104 a), followed by a second reductive alkylation with the appropriate benzaldehyde and subsequent deprotection as described above for Example 52.

EXAMPLE 110

(3S)-N-[(2-Chlorophenyl)methyl]-N-(2-methylpropyl)-pyrrolidin-3-amine fumarate $^1$H NMR (300 MHz, CD$_3$OD) $\delta_H$: 0.77-0.80 (dd, 6H), 1.52-1.66 (sep, 1H), 1.82-1.95 (m, 1H), 1.20-2.10 (m, 1H), 2.20-2.32 (m, 2H), 2.99-3.16 (m, 2H), 3.26-3.35 (m, 2H), 3.56 (quin, 1H), 3.70-3.77 (m, 2H), 6.60 (s, 2H), 7.13-7.24 (m, 2H), 7.29 (dd, 1H), 7.46 (dd,1H); MS: [M+H]=267.

EXAMPLE 111

(3S)-N-{[2-(Methoxy)phenyl]methyl}-N-(2-methylpropyl)pyrrolidin-3-amine fumarate $^1$H NMR (300 MHz, CD$_3$OD) $\delta_H$: 0.82 (dd, 6H), 1.66 (sept, 1H), 1.79-1.92 (m, 1H), 1.92-2.06 (m, 1H), 2.19-2.22 (m, 2H), 2.96-3.13 (m, 2H), 3.18-3.31 (m, 2H), 3.59-3.67 (m, 2H), 3.74 (s, 3H), 6.59 (s, 2H), 6.80-6.87 (m, 2H), 7.11-7.18 (m, 1H), 7.25 (dd, 1H); MS: [M+H]=263.

EXAMPLE 112

(3S)-N-{[2-(Ethyloxy)phenyl]methyl}-N-(2-methylpropyl)pyrrolidin-3-amine fumarate $^1$H NMR (300 MHz, CD$_3$OD) $\delta_H$: 0.73-0.76 (2x d, 6H), 1.27-1.32 (t, 3H), 1.56-1.70 (sep, 1H), 1.76-1.89 (m, 1H), 1.92-2.02 (m, 1H), 2.17 (dd, 1H), 2.92-3.07 (m, 2H), 3.07-3.19 (m, 2H), 3.47-3.63 (m, 3H), 3.89-3;96 (m, 2H), 6.55 (s, 2H), 6.74-6.81 (m, 2H), 7.08 (dt, 1H), 7.21 (dd, 1H); MS: [M+H]=277.

EXAMPLE 113

(3S)-N-[(2-Methylphenyl)methyl]-N-(2-methylpropyl)-pyrrolidin-3-amine fumarate $^1$H NMR (300 MHz, CD$_3$OD) $\delta_H$: 7.78-7.36 (m, 1H), 7.12-7.13 (m, 3H), 6.65 (s,2H), 3.51-3.72b(q+m, 3H), 3.24-3.42 (m, 2H+MeOH), 3.01-3.19 (m, 2H), 2.34 (s, 3H), 2.26-2.29 (dd, 2H), 1.91-2.13 (m,2H), 1.55-1.69 sep, 1H), 0.81-0.84 (d, 6H); MS: [M+H]=247.

EXAMPLE 114

(3S)-N-(2-Methylpropyl)-N-(phenylmethyl)pyrrolidin-3-amine fumarate $^1$H NMR (300 MHz, CD$_3$OD) $\delta_H$: 7.36-7.49 (m, 5H), 6.84 (s, 2H), 3.70-3.91 (q+quin, 3H), 3.28-3.56 (m, 2H), 3.16-3.24 (m, 1H), 2.45-2.47 (dd, 2H), 2.20-2.31 (m, 1H), 2.05-2.16 (m, 1H), 1.85-1.99 (sep, 1H), 1.05-1.07 (d, 6H); MS: [M+H]=233.

EXAMPLE 115

(3S)-N-(2-Methylpropyl)-N-[(naphthalen-1-yl)methyl]-pyrrolidin-3-amine fumarate $^1$H NMR (300 MHz, CD$_3$OD) $\delta_H$: 8.37-8.40 (m, 1H); 7.90-7.99 (M, 2H), 7.51-7.70 (m, 4H), 6.79 (s, 2H), 4.16-4.33 (q, 2H), 3.70-3.81 (quin, 1H), 3.36-3.53 (m, 2H), 3.18-3.31 (m, 2H), 2.49-2.54 (d, 2H), 2.06-2.27 (m, 2H), 1.78-1.87 (m, 1H), 0.96-0.99 (d, 6H); MS: [M+H]=283.

EXAMPLE 116

(3S)-N-{[4-Fluoro-2-(methoxy)phenyl]methyl}-N-(2-methylpropyl)pyrrolidin-3-amine fumarate $^1$H NMR (300 MHz, CD$_3$OD) $\delta_H$: 7.08-7-12 (d, 1H), 6.84-6.93 (m,3H), 6.63 (s, 2H), 3.76 (s, 3H), 3.48-3.68 (m, 3H), 3.25-3.36 (m, 2H), 2.99-3.18 (m, 2H), 2.20-2.32 (dd, 2H), 2.01-2.11 (m, 1H) 1.81-1.95 (m, 1H), 1.61-1.75 (sep, 1H, 0.82-86 (dd, 3H); MS: [M+H]=281.

EXAMPLE 117

(3S)-N-(2-Methylpropyl)-N-{[2-(phenyloxy)phenyl]methyl}-pyrrolidin-3-amine fumarate $^1$H NMR (300 MHz, CD$_3$OD) δ$_H$: 7.51-7.54 (dd, 1H), 7.04-7.35 (m, 5H), 6.86-6.91 (m, 3H), 6.67 (s, 2H), 3.62-3.76 (m, 3H), 3.24-3.36 (m, 2H), 3.00-3.18 (m, 2H), 2.27-2.30 (dd, 2H), 1.96-2.06 (m, 1H), 1.86-1.93 (m, 1H), 1.68-1.76 (quin, 1H), 0.84-0.87 (dd, 6H); MS: [M+H]=325.

EXAMPLE 118

(3S)-N-{[2-Chloro-3-(trifluoromethyl)phenyl]methyl}-N-(2-methylpropyl)pyrrolidin-3-amine D-tartrate $^1$H NMR (300 MHz, CD$_3$OD) δ$_H$: 7.77 (1H, s), 7.46-7.39 (2H, m), 4.24 (2H, s), 3.72 (2H, m), 3.66-2.92 (5H, m), 2.25-2.15 (2H, m), 2.08-1.96 (1H, m), 1.88-1.73 (1H, m), 1.57-1.43 (1H, m), 0.73 (6H, dd); MS: [M+H]=335.

EXAMPLE 119

(3S)-N-[(2-Chloro-4-fluorophenyl)methyl]-N-(2-methylpropyl)pyrrolidin-3-amine di-D-tartrate $^1$H NMR (300 MHz, d6-DMSO) δ$_H$: 0.76-0.80 (m, 6H), 1.50-1.66 (m, 1H), 1.70-1.86 (m, 1H), 1.92-2.05 (m, 1H), 2.18-2.30 (m, 2H), 2.90-3.11 (m, 2H), 3.20-3.32 (m, 2H), 3.45-3.56 (m, 1H), 3.60-3.72 (m, 2H), 4.12 (s, 4H), 7.23 (td, 1H), 7.41 (dd, 1H), 7.57 (dd, 1H); MS: [M+H]=285 and 287.

EXAMPLE 120

(3)-N-[(2,4-Dichlorophenyl)methyl]-N-(2-methylpropyl)-pyrrolidin-3-amine sesqui-D-tartrate $^1$H NMR (300 MHz, d6-DMSO) δ$_H$: 0.77-0.80 (m, 6H), 1.51-1.65 (m, 1H), 1.69-1.86 (m, 1H), 1.92-2.06 (m, 1H), 2.24-2.26 (m, 2H), 2.90-3.10 (m, 2H), 3.20-3.32 (m, 2H), 3.43-3.58 (m, 1H), 3.62-3.68 (m, 2H), 4.05 (s, 3H), 7.44 (dd, 1H), 7.50-7.59 (m, 2H); MS: [M+H]=301/303/305.

EXAMPLE 121

(3R)-N-{[2-Chloro-3-(trifluoromethyl)phenyl]methyl}-N-(2-methylpropyl)pyrrolidin-3-amine D-tartrate $^1$H NMR (300 MHz, CD$_3$OD) δ$_H$: 7.77 (1H, s), 7.46-7.39 (2H, m), 4.24 (2H, s), 3.72 (2H, m), 3.66-2.92 (5H, m), 2.25-2.15 (2H, m), 2.08-1.96 (1H, m), 1.88-1.73 (1H, m), 1.57-1.43 (1H, m), 0.73 (6H, dd); MS: [M+H]=335.

EXAMPLE 122

(3R)-N-[(2-Chloro-3-methylphenyl)methyl]-N-(2-methylpropyl)pyrrolidin-3-amine D-tartrate $^1$H NMR (300 MHz, CD$_3$OD) δ$_H$: 7.44-7.39 (1H, m), 7.22-7.17 (2H, m), 4.40 (2H, s), 3.87-3.76 (2H, d), 3.71-3.08 (5H, m), 2.25-2.15 (2H, m), 2.08-1.96 (1H, m), 1.88-1.73 (1H, m), 1.57-1.43 (1H, m), 0.73 (6H, dd); MS: [M+H]=281.

EXAMPLE 123

(3R)-N-[(2-Chloro-4-fluorophenyl)methyl]-N-(2-methylpropyl)pyrrolidin-3-amine D-tartrate $^1$H NMR (300 MHz, CD$_3$OD) δ$_H$: 7.42-7.37 (1H, dd), 7.04 (1H, dd), 7.02 (1H, dd), 6.90 (1H, dt), 4.21 (2H, s), 3.57 (2H, m), 3.51-3.40 (1H, m), 3.25-2.89 (4H, m), 2.21-2.09 (2H, dd), 2.00-1.89 (1H, m), 1.85-1.71 (1H, m), 1.55-1.41 (1H, m), 0.69-0.66 (6H, dd); MS: [M+H]=285/287.

EXAMPLE 124

(3S)-N-{[3-Fluoro-2-(trifluoromethyl)phenyl]methyl}-N-(2-methylpropyl)pyrrolidin-3-amine D-tartrate $^1$H NMR (300 MHz, CD$_3$OD) δ$_H$: 7.97-7.93 (1H, dd), 7.46-7.37 (2H, m), 4.41 (2H, s), 3.84 (2H, s), 3.68-3.57 (1H, m), 3.45-3.36 (1H, m), 3.34-3.32 (1H, m), 3.26-3.17 (1H, m), 3.12-3.01 (1H, m), 2.42-2.31 (2H, m), 2.16-2.05 (1H, m), 2.01-1.88 (1H, m), 1.76-1.62 (1H, m), 0.91 (6H, dd); MS: [M+H]=319.

EXAMPLE 125

(3R)-N-{[4-Fluoro-2-(trifluoromethyl)phenyl]methyl}-N-(2-methylpropyl)pyrrolidin-3-amine D-tartrate $^1$H NMR (300 MHz, CD$_3$OD) δ$_H$: 7.73 (1H, d), 7.67-7.59 (1H, m), 7.25-7.19 (1H, m) 4.41 (2H, s), 3.91 (2H, m), 3.65-3.55 (1H, m), 3.45-3.35 (1H, m), 3.34-3.32 (1H, m), 3.26-3.16 (1H, m), 3.11-3.04 (1H, m), 2.40-2.33 (2H, m), 2.18-2.07 (1H, m), 2.01-1.90 (1H, m), 1.96-1.56 (1H, m), 0.90 (6H, dd); MS: [M+H]=319.

EXAMPLE 126

(3S)-N-(2-Methylpropyl)-N-{[2-(methylthio)phenyl]methyl}-pyrrolidin-3-amine D-tartrate $^1$H NMR (300 MHz, CD$_3$OD) δ$_H$: 7.44 (1H, d), 7.32 (2H, m), 7.17 (1H, dt), 4.41 (2H, s), 3.81-3.60 (2H, m), 3.44-3.32 (4H, m), 3.25-3.14 (1H, m), 2.47 (1H, S), 2.32 (2H, dd), 2.18-1.94 (2H, m), 1.71-1.60 (1H, m), 1.73 (6H, dd); MS: [M+H]=279.

EXAMPLE 127

(3R)-N-(2-Methylpropyl)-N-{[2-(methylthio)phenyl]methyl}-pyrrolidin-3-amine D-tartrate $^1$H NMR: Spectra were comparable with the S enantiomer as described in Example 126; MS: [M+H]=279.

EXAMPLE 128

(3S)-N-[(2-Chloro-3-methylphenyl)methyl]-N-(2-methylpropyl)-pyrrolidin-3-amine D-tartrate $^1$H NMR (300 MHz, d6-DMSO) δ$_H$: 0.79-0.81 (m, 6H), 1.53-1.64 (m, 1H), 1.70-1.84 (m, 1H), 1.87-2.12 (m, 1H), 2.26-2.28 (m, 2H), 2.33 (s, 3H), 2.90-3.07 (m, 2H), 3.21-3.28 (m, 2H), 3.45-3.56 (m, 1H), 3.69-3.70 (m, 2H), 3.88 (s, 2H), 7.20-7.26 (m, 2H), 7.38-7.41 (m, 1H). MS: [M+H]=281/283.

EXAMPLE 129

(3S)-N-[(3,5-Dichlorophenyl)methyl]-N-(2-methyl-propyl)-pyrrolidin-3-amine D-tartrate $^1$H NMR (300 MHz, d6-DMSO) $\delta_H$: 0.80-0.82 (m, 6H), 1.58-1.79 (m, 2H), 1.92-2.02 (m, 1H), 2.15-2.27 (m, 2H), 2.87-2.94 (m, 1H), 2.98-3.07 (m, 1H), 3.22-3.29 (m, 2H), 3.43-3.54 (m, 1H), 3.56-3.69 (m, 2H), 3.94 (s, 2H), 7.36-7.37 (m, 2H), 7.46-7.47 (m, 1H). MS: [M+H]=301/303/305.

EXAMPLE 130

(3S)-N-[(3-Chloro-2-methylphenyl)methyl]-N-(2-methylpropyl)-pyrrolidin-3-amine D-tartrate $^1$H NMR (300 MHz, d6-DMSO) $\delta_H$: 0.77-0.79 (m, 6H), 1.49-1.63 (m, 1H), 1.71-1.85 (m, 1H), 1.91-2.01 (m, 1H), 2.21-2.23 (m, 2H), 2.34 (s, 3H), 2.89-3.06 (m, 2H), 3.19-3.29 (m, 2H), 3.39-3.50 (m, 1H), 3.56-3.69 (m, 2H), 3.87 (bs, 2H), 7.16-7.21 (m, 1H), 7.32-7.35 (m, 2H). MS: [M+H]=281/283.

The following Examples were prepared from 1,1-dimethylethyl (3S)-3-({[2-(trifluoromethyl)phenyl]-methyl}amino)pyrrolidine-1-carboxylate or 1,1-dimethylethyl (3R)-3-({[2-(trifluoromethyl)phenyl]-methyl}amino) pyrrolidine-1-carboxylate by reductive alkylation with the appropriate aldehyde or ketone and subsequent deprotection, as described above for Example 53.

EXAMPLE 131

(3S)-N-(3,3-Dimethylbutyl)-N-{[2-(trifluoromethyl)-phenyl]methyl}pyrrolidin-3-amine sesquifumarate $^1$H NMR (300 MHz, CD$_3$OD) $\delta_H$: 7.70-7.73 (d, 1H), 7.38-7.48 (d+t, 2H), 7.19-7.24 (t, 1H), 6.50 (s, 3H), 3.60-3-74 (q, 2H), 3.37-3.47 (quin, 1H), 2.87-3.30 (m, 6H), 2.39-2.45 (m, 2H), 1.91-2.02 (m, 1H), 1.70-1.83 (m, 1H); MS: [M+H]=329.

EXAMPLE 132

(3S)-N-(1-Methylethyl)-N-{[2-(trifluoromethyl)-phenyl]methyl}pyrrolidin-3-amine fumarate $^1$H NMR (300 MHz, CD$_3$OD) $\delta_H$: 7.98-8.00 (d, 1H), 7.60-7.68 (d+t, 2H), 7.38-7.43(t, 1H), 6.70 (s, 2H), 3.91 (bs, 2H), 3.74-3.85 (m, 1H), 3.17-3.40 (M, 5H), 2.96-3.10 (m,3H), 2.08-2.18 (m, 1H), 1.82-1.96 (m,1H), 1.08-1.11 (dd, 6H); MS: [M+H]=287.

EXAMPLE 133

(3S)-N-(2-methylpropyl)-N-{[2-(trifluoromethyl)phenyl]-methyl}pyrrolidin-3-amine fumarate $^1$H NMR (300 MHz, CD$_3$OD) $\delta_H$: 7.72-7.75 (t, 1H), 7.42-7.51 (d+t, 2H), 7.72-7.27 (t, 1H), 6.51 (s, 2H), 3.63-3.74 (bs, 2H), 3.38-3.49 (m, 1H), 2.86-3.25 (m, 2H), 2.17-2.25 (m, 2H), 1.88-1.99 (m,1H), 1.69-1.83 (m, 1H), 1.46-1.59 (m, 1H), 0.74-0.76 (d, 6H); MS: [M+H]=301.

EXAMPLE 134

(3R)-N-(2-Methylpropyl)-N-{[2-(trifluoromethyl) phenyl]-methyl}pyrrolidin-3-amine $^1$H NMR (300 MHz, CD$_3$OD) $\delta_H$: 7.92-7.94 (d, 1H), 7.60-7.69(d+t, 2H), 7.41-7.46 (t, 1H), 6.69 (s, 1H), 3.82-3.93 (bs, 2H), 3.56-3.68 (m,1H), 3.32-3.44 (m, 2H), 3.05-3.24 (m, 2H), 2.31-2.43 (dd, 2H), 2.07-2.17 (m,1H), 1.88-1.98 (m,1H), 1.65-1.78 (m, 1H), 0.92-0.95 (d, 6H); MS: [M+H]=301.

EXAMPLE 135

(3S)-N-Ethyl-N-{[2-(trifluoromethyl)phenyl]methyl}-pyrrolidin-3-amine fumarate $^1$H NMR (300 MHz, CD$_3$OD) $\delta_H$: 8.00-8.03 (d, 1H), 7.67-7.76 (d+t, 2H), 7.47-7.52 (t, 1H), 6.77 (s, 2H), 3.89-4.03 (q, 2H), 3.65-3.75 (quin, 2H), 3.43-3.53 (m, 2H), 3.28-3.41 (m, 1H), 3.17-3.23 (m, 1H), 2.73-2.84 (q, 2H), 2.19-2.30 (m, 2H), 2.19-2.30 (m, 1H), 1.98-2.14 (m, 1H), 1.10-1.15 (t, 3H); MS: [M+H]=273.

EXAMPLE 136

(3S)-N-Propyl-N-{[2-(trifluoromethyl)phenyl]methyl}-pyrrolidin-3-amine fumarate $^1$H NMR (300 MHz, CD$_3$OD) $\delta_H$: 7.92-7.94 (d, 1H), 7.60-7.69) d+t, 2H), 7.40-7.45 (t, 1H), 6.69-6.73 (s, 2H), 3.82-3.98 (q, 2H), 5. 59-3.69(quin, 1H), 3.35-3.45 (m, 2H), 2.80-3.21 (m, 1H), 3.08-3.15 (m, 1H), 2.54-2.59 (q, 2H), 2.10-2.21 (m, 1H), 1.90-2.06 (m, 1H), 1.44-1.56 (quin, 2H), 0.86-0.91 (T, 3H); MS: [M+H]=287.

EXAMPLE 137

(3S)-N-(Cyclohexylmethyl)-N-{[2-(trifluoromethyl)-phenyl]methyl}pyrrolidin-3-amine fumarate $^1$H NMR (300 MHz, CD$_3$OD) $\delta_H$: 77.89-7.92 (d, 1H), 7.61-7.70 (d+t, 2H), 7.41-7.49 (t, 1H), 6.70 (s, 2H), 3.81-3.95 (q, 2H), 3.56-3.67 (quin, 1H), 3.31-3.43 (m, 2H), 3.14-3.23 (m, 1H), 3.04-3.11 (m, 1H), 2.39-2.41 (d, 2H); 2.06-2.13 (m, 1H), 1.70-2.01 (m, 6H), 1.34-1.46 (m, 1H), 1.12-1.23 (m, 1H), 0.83-0.89 (m, 2H); MS: [M+H]=341.

EXAMPLE 138

(3S)-N-(Cyclopropylmethyl)-N-{[2-(trifluoromethyl)-phenyl]methyl}pyrrolidin-3-amine fumarate $^1$H NMR (300 MHz, CD$_3$OD) $\delta_H$: 7.88-7.91 (d, 1H), 7.50-7.59 (d+t, 2H), 7.30-7.50 (t, 1H), 6.60 (s, 2H), 3.89-3.99 (q, 2H), 3.65-3.76 (quin, 1H), 3.27-3.35 (m, 2H), 3.10-3.22 (m, 1H), 2.99-3.06 (q, 1H), 2.40-2.43 (d, 2H), 2.04-2.15 (m, 1H), 1.81-1-95 (m, 1H), 0.73-0.85 (m, 1H), 0.34-0.42 (d, 2H), 0.02-0.05 (d, 2H); MS: [M+H]299.

EXAMPLE 139

(3S)-N-(2-Phenylethyl)-N-{[2-(trifluoromethyl)phenyl]-methyl}pyrrolidin-3-amine fumarate $^1$H NMR (300 MHz, CD$_3$OD) $\delta_H$: 7.67-7.69 (d, 1H), 7.55-7.58 (d, 1H), 7.42-7.47 (t, 1H), 7.23-7.33 b(t, 1H), 7.01-7.17 (m, 5H), 6.58 (s, 2H), 3.80-3.93 (q, 2H), 3.47-3.64 (m, 1H), 3.20-3.40 (m, 2H), 3.07-3.18 (m, 1H), 2.91-2.98 (M, 1H), 2.71-2.76 (m, 2H), 2.62-2.67 (m,2H), 2.00-2.20 (m, 1H), 1.78-1.91 (m, 1H); MS: [M+H]349.

EXAMPLE 140

(3S)-N-Butyl-N-{[2-(trifluoromethyl)phenyl]methyl}-pyrrolidin-3-amine fumarate $^1$H NMR (300 MHz, CD$_3$OD) δ$_H$: 7.91-7.94 (d, 1H), 7.60-7.69 (m, 2H), 7.40-7.45 (t, 1H), 6.70 (s, 2H), 3.82-3.96 (q, 2H), 3.59-3.69 (quin, 1H), 3.32-3.50 (m, 2H), 3.22-3.29 (m, 1H), 3.09-3.15 (q, 1H), 2.58-2.63 (t, 2H), 2.10-2.21 (m, 1H), 1.90-2.04 (m, 1H), 1.42-1.51 (m, 2H), 1.17-1.37 (m, 2H), 0.87-0.91 (t, 3H); MS: [M+H]=301.

EXAMPLE 141

(3S)-N-(2-Ethylbutyl)-N-{[2-(trifluoromethyl)phenyl]-methyl}pyrrolidin-3-amine sesquifumarate $^1$H NMR (300 MHz, CD$_3$OD) δ$_H$: 7.77-7.80 (d, 1H), 7.49-7.60 (m, 2H), 7.29-7.34 (t, 1H), 6.60 (s, 1.5H), 3.70-3.81 (q, 2H), 3.46-3.57 (quin, 1H), 3.20-3.33 (m, 2H), 2.94-3.13 (m, 2H), 2.32-2.34 (d, 2H), 1.97-2.07 (m 1H), 1.78-1.91 (m, 1H), 1.05-1.40 (m, 5H), 0.69-0.76 (m, 6H). MS: [M+H]=329.

EXAMPLE 142

(3S)-N-(2-Methylprop-2-enyl)-N-{[2-(trifluoromethyl)-phenyl]methyl}pyrrolidin-3-amine fumarate $^1$H NMR (300 MHz, CD$_3$OD) δ$_H$: 7.78-7.81 (d, 1H), 7.49-7.58 (m, 2H), 7.29-7.34 (t, 1H), 6.57 (s, 2H), 4.80-4.91 (d, 2H), 3.68-3.80 (q, 2H), 3.52-3.62 (quin, 1H), 3.20-3.33 (m, 2H), 1.96-2.08 (m, 1H), 1.83-1.93 (m, 1H), 1.66 (s, 3H); MS: [M+H]=299.

EXAMPLE 143

(3S)-N-{[2-(Trifluoromethyl)phenyl]methyl}-N-(3,3,3-trifluoropropyl)pyrrolidin-3-amine fumarate $^1$H NMR (300 MHz, CD$_3$OD) δ$_H$: 7.76-7.78 (d, 1H), 7.50-7.60 (d+t, 2H), 7.32-7.37 (t, 1H), 6.58 (s, 2H), 3.75-3.89 (q, 2H), 3.48-3.59 (quin, 1H), 3.126-3.22 (m, 1H), 2.98-3.05 (dd, 1H), 2.75-2.80 (t, 2H), 2.18-2.34 (m, 2H), 2.02-2.13 (m, 1H), 1.80-1.93 (m, 1H); MS: [M+H]=341.

EXAMPLE 144

(3S)-N-(4,4,4-Trifluorobutyl)-N-{[2-(trifluoromethyl)-phenyl]methyl}pyrrolidin-3-amine fumarate $^1$H NMR (300 MHz, CD$_3$OD) δ$_H$: 7.75-7.77 (d, 1H), 7.50-7.59 (d+t, 2H), 7.31-7.40 (t, 1H), 1.65 (s, 2H), 3.73-7.86 (q, 2H), 3.48-3.59 (quin, 1H), 3.25-3.42 (m, 2H), 3.07-3.17 (m, 1H), 2.97-3.03 (m, 1H), 2.54-2.59 (t, H), 1.98-2.11 (m, 3H), 1.79-1.95 (m, 1H), 1.52 -1.62 (quin, 2H); MS: [M+H]=355.

EXAMPLE 145

(3S)-N-(Furan-2-ylmethyl)-N-{[2-(trifluoromethyl)phenyl]-methyl}pyrrolidin-3-amine D-tartrate $^1$H NMR (300 MHz, CD$_3$OD) δ$_H$: 7.83-7.86 (d, 1H), 7.49-7.58 (t+s, 2H), 7.29-7.38 (m, 2H), 6.23-6.26 (m, 1H), 6.14-6.15 (m, 1H), 4.30 (s, 2H), 3.78-3.91 (q, 2H), 3.66-3.67 (m, 2H), 3.25-3.55 (m, 3H), 2.30-3.17 (m, 2H), 2.05-2.16 (m, 1H), 1.83-1.96 (m, 1H); MS: [M+H]=325.

EXAMPLE 146

(3S)-N-(3-Methylbutyl)-N-{[2-(trifluoromethyl)phenyl]-methyl}pyrrolidin-3-amine D-tartrate $^1$H NMR (300 MHz, CD$_3$OD) δ$_H$: 7.67-7.70 (d,1H), 7.35-7.45 (d+t, 2H), 7.16-7.21 (t, 1H), 4.16-4.18 (s, 2H), 3.57-3.71 (q, 2H), 3.35-3.45 (quin, 1H), 3.14-3.21 (m,2H), 2.97-3.04 (m, 1H), 2.84-2.91 (m,1H), 2.35-2.40 (m, 2H), 1.86-1.97 (m, 1H), 1.66-1.79 (m, 1H), 1.24-1.37 (sept, 1H), 1.08-1.16 (m, 2H), 0.59-0.62 (d, 6H); MS: [M+H]=315.

EXAMPLE 147

(3S)-N-[3-(Methylthio)propyl]-N-{[2-(trifluoromethyl)-phenyl]methyl}pyrrolidin-3-amine D-tartrate $^1$H NMR (300 MHz, CD$_3$OD) δ$_H$: 7.90-7.92 (d,1H), 7.61-7.70 (d+t, 2H), 7.41-7.46 (t, 1H), 4.42 (s, 2H), 3.84-3.97 (q, 2H), 3.59-3.69 (quin, 1H), 3.38-3.47 (m, 2H), 3.19-3.29 (m, 1H), 3.09-3.16 (m, 1H), 2.70-2.77 (dt, 2H), 2.48-2.52 (t, 2H), 2.08-2.21 (m, 1H), 1.89-2.08 (s+m, 4H), 1.69-1.79 (quin, 2H); MS: [M+H]=333.

EXAMPLE 148

(3S)-N-(2,2-Dimethylpropyl)-N-{[2-(trifluoromethyl)-phenyl]methyl}pyrrolidin-3-amine D-tartrate $^1$H NMR (300 MHz, CD$_3$OD) δ$_H$: 8.10-8.12 (d, 1H), 7.65-7.70 (t, 2H), 7.41-7.46 (t, 1H), 4.41 (s, 2H), 4.01 (s, 2H), 3.50-3.62 (quin, 1H), 3.31-3.43 (m, 2H), 3.04-3.20 (m, 2H), 2.50 (s, 2H), 2.06-2.17 (m, 1H), 1.85-1.99 (m, 1H), 0.96 (s, 9H): MS: [M+H]=315.

EXAMPLE 149

N-(Phenylmethyl)-N-[(3S)-pyrrolidin-3-yl]-N-{[2-(trifluoromethyl)phenyl]methyl}amine fumarate $^1$H NMR (300 MHz, CD$_3$OD) δ$_H$: 7.93-7.96 (d, 1H), 7.60-7.68 (q, 2H), 7.23-7.44 (m, 6H), 6.69 (s, 2H), 3.83-3.94 (s, 2H), 3.61-3.80 (m, 3H), 3.32-3.44 (m, 2H), 3.08-3.25 (m, 2H), 1.99-2.22 (m, 2H); MS: [M+H]=335.

EXAMPLE 150

(3S)-N-[(4-Fluorophenyl)methyl]-N-{[2-(trifluoromethyl)-phenyl]methyl}pyrrolidin-3-amine fumarate $^1$H NMR (300 MHz, CD$_3$OD) δ$_H$: 7.90-8.00 (d, 1H), 7.59-7.67 (q, 2H), 7.31-7.44 (m, 3H), 7.02-7.08 (t, 2H), 6.71 (s, 2H), 3.88 (s, 2H), 3.56-3.77 (m, 3H), 3.31-3.52 (m, 2H), 3.15-3.26 (m, 2H), 1.99-2.22 (m, 2H); MS: [M+H]353.

EXAMPLE 151

(3S)-N-{[2-(Ethyloxy)phenyl]methyl}-N-{[2-(trifluoromethyl)phenyl]methyl}pyrrolidin-3-amine fumarate $^1$H NMR (300 MHz, CD$_3$OD) δ$_H$: 7.84-7.87 (d, 1H), 7.52-7.64 (m, 2H), 7.18-7.39 (m, 3H), 6.85-6.96 (m, 2H), 6.70 (s, 2H), 4.06-4.13 (q, 2H), 3.95-3.97 (s,2H), 3.61-3.86 (m, 3H), 3.61-3.51 (m,4H), 2.04-2.20 (m,2H), 1.42-1.46 (t,3H); MS: [M+H]=379.

EXAMPLE 152

(3S)-N-[(2-Chlorophenyl)methyl]-N-{[2-(trifluoromethyl)-phenyl]methyl}pyrrolidin-3-amine fumarate $^1$H NMR (300 MHz, CD$_3$OD) $\delta_H$: 7.84-7.87 (d,1H), 7.62-7.64 (d, 1H), 7.50-7.57 (m,2H), 7.35-7.40 (m, 2H), 7.20-7.29 (m, 2H), 6.69 (s, 2H), 3.88-3.97 (m, 4H), 3.65-3.76 (quin, 1H), 3.38-3.47 (m, 2H), 3.18-3.28 (m, 2H), 2.05-2.26 (m, 2H); MS: [M+H]=369.

EXAMPLE 153

(3S)-N-[(2-Fluorophenyl)methyl]-N-{[2-(trifluoromethyl)-phenyl]methyl}pyrrolidin-3-amine fumarate $^1$H NMR (300 MHz, CD$_3$OD) $\delta_H$: 7.83-7.86 (d, 1H), 7.62-7.65 (d, 1H), 7.54-7.65 (t, 1H), 7.36-7.45 (m, 2H), 7.25-7.32 (m, 1H), 7.04-7.15 (m, 2H), 6.69 (s,2H), 3.92 (bs, 2H), 3.76-3.88 (q, 2H), 3.75-3.64 (quin, 21H), 3.37-3.46 (m, 2H), 3.18-3.27 (m, 2H), 2.01-2.24 (m, 2H); MS: [M+H]=353.

EXAMPLE 154

(3S)-N-{[2-(Methyloxy)phenyl]methyl}-N-{[2-(trifluoromethyl)phenyl]methyl}pyrrolidin-3-amine fumarate $^1$H NMR (300 MHz, CD$_3$OD) $\delta_H$: 7.85-7.87 (d, 1H), 7.61-7.64 (d, 1H), 7.52-7.58 (t, 1H), 7.21-7.40 (m,3H), 6.81-6.97 (m, 2H), 6.69 (s, 2H), 3.61-3.97 (m, 8H), 3.16-3.44 (m, 4H), 1.20-2.21 (m, 2H); MS: [M+H]=365.

EXAMPLE 155

(3S)-N,N-bis {[2-(Trifluoromethyl)phenyl]methyl}-pyrrolidin-3-amine fumarate $^1$H NMR (300 MHz, CD$_3$OD) $\delta_H$: 7.90-7.92 (d, 2H), 7.66-7.69 (d, 2H), 7.59-7.64 (t, 2H), 7.40-7.45 (t, 2H), 6.69 (s, 2H), 3.91 (s, 4H), 3.62-3-74 (quin, 1H), 3.36-3.46 (m, 2H), 3.16-3.26 (m, 2H), 2.02-2.24 (m, 2H); MS: [M+H]=403.

EXAMPLE 156

(3S)-N-(2-Ethylbutyl)-N-{[2-(trifluoromethyl)-phenyl]methyl}pyrrolidin-3-amine, D-tartrate $^1$H NMR (300 MHz, CD$_3$OD): $\delta_H$7.94-7.92 (d, 1H), 7.72-7.69 (m, 2H), 7.48-7.43 (t, 1H), 4.44 (s, 2H), 3.96-3.84 (m, 2H), 3.71-3.60 (m, 1H), 3.46-3.38 (m, 2H), 3.28-3.18 (m, 1H), 3.15-3.08 (m, 1H), 2.49-2.47 (m, 2H), 2.20-2.10 (m, 1H), 2.05-1.91 (m, 1H), 1.54-1.24 (m, 5H), 0.90-0.83 (t, 6H); MS: [M+H]=329.

EXAMPLE 157

(3S)-N-{[2-(Trifluoromethyl)phenyl]methyl}-N-(3,3,3-trifluoropropyl)pyrrolidin-3-amine, D-tartrate $^1$H NMR (300 MHz, CD$_3$OD): $\delta_H$ 7.93-7.90 (d, 1H), 7.74-7.64 (m, 2H), 7.51-7.46 (t, 1H), 4.44 (s, 2H), 4.02-3.89 (m, 2H), 3.73-3.62 (m, 1H), 3.50-3.42 (m, 2H), 3.36-3.23 (m, 1H), 3.18-3.12 (dd, 1H), 2.94-2.89 (m, 2H), 2.48-2.32 (m, 2H), 2.24-2.15 (m, 1H), 2.07-1.94 (m, 1H); MS: [M+H]=341.

EXAMPLE 158

(3S)-N-(4,4,4-Trifluorobutyl)-N-{[2-(trifluoromethyl)-phenyl]methyl}pyrrolidin-3-amine, D-tartrate $^1$H NMR (300 MHz, CD$_3$OD): $\delta_H$7.92-7.89 (d, 1H), 7.73-7.64 (m, 2H), 7.50-7.45 (t, 1H), 4.44 (s, 2H), 4.00-3.87 (m, 2H), 3.73-3.63 (m, 1H), 3.49-3.41-(m, 2H), 3.32-3.25 (m, 1H), 3.22-3.11 (dd, 1H), 2.73-2.69 (m, 2H), 2.24-2.09 (m, 3H), 2.06-1.93 (m, 1H), 1.76-1.66 (m, 2H); MS: [M+H]=355.

EXAMPLE 159

(3S)-N-Ethyl-N-{[2-(trifluoromethyl)-phenyl]methyl}-pyrrolidin-3-amine, D-tartrate

MS: [M+H]=273.

The following Examples were prepared from 1,1-dimethylethyl (3S)-3-aminopyrrolidine-1-carboxylate by reductive alkylation with two equivalents of the appropriate benzaldehyde and subsequent deprotection as described above for Example 53.

EXAMPLE 160

(3S)-N,N-bis-[(2-Chloro-4-fluorophenyl)methyl]-pyrrolidin-3-amine D-tartrate $^1$H NMR (300 MHz, d6-DMSO) $\delta_H$: 1.83-2.13 (m, 2H), 3.00-3.17 (m, 2H), 3.22-3.36 (m, 2H), 3.51-3.59 (m, 1H), 3.68-3.78 (m, 4H), 3.87 (s, 2H), 7.14 (td, 2H), 7.34 (dd, 2H), 7.51 (dd, 2H); MS: [M+H]=371/373.

EXAMPLE 161

(3S)-N,N-bis-[(2,4-Dichlorophenyl)methyl]-pyrrolidin-3-amine D-tartrate $^1$H NMR (300 MHz, d6-DMSO) $\delta_H$: 1.81-1.97 (m, 1H), 1.99-2.12 (m, 1H), 2.99-3.15 (m, 2H), 3.21-3.35 (m, 2H), 3.50-3.60 (m, 1H), 3.69-3.80 (m, 4H), 3.86 (s, 2H), 7.35 (dd, 2H), 7.48-7.52 (m, 4H); MS: [M+H]=403/405/407.

EXAMPLE 162

1-{[(3,5-Dichlorophenyl)methyl][(3S)-pyrrolidin-3-yl]amino}-2-methylpropan-2-ol D-tartrate To a solution of 1,1-dimethylethyl (3S)-3-([(3,5-dichlorophenyl)methyl]amino)pyrrolidine-1-carboxylate (1.11 g, 3.2 mmol) in ethanol (30 mL) was added isobutylene oxide (1 mL, 11.2 mmol) and water (10 mL). The reaction mixture was heated to reflux. After 2 hours additional isobutylene oxide (5 mL, 56.1 mmol) was added, and a similar amount again after 3 days. After a total of 4 days at reflux no further reaction was observed (LC-MS), so the reaction was halted. The cooled reaction mixture was concentrated in vacuo and then redissolved in methanol. The crude product was absorbed onto a cationic ion exchange resin (Isolute™ SCX-2) and the basic fraction recovered from the column by elution with 2N ammonia in methanol. The eluate was concentrated in vacuo and the residue redissolved in dichloromethane/trifluoroacetic acid (2:1) and stirred at room temperature overnight. The reaction mixture was concentrated in vacuo and redissolved in methanol, and again purified on a cationic ion exchange resin cartridge (Isolute™ SCX-2). The recovered basic fractions were further purified by UV guided prep-LC and the desired compound collected from the acidic preparative-LC mobile phase via a cationic ion exchange resin as described above. The residue was dissolved in hot cyclohexane and to this was added an equimolar amount of D-tartaric acid dissolved in a minimal amount of hot isopropanol. The solution was allowed to crystallise overnight, and the resulting solid was filtered off and dried in vacuo, to yield the title compound as a white crystalline solid. $^1$H NMR (300 MHz, d6-DMSO) $\delta_H$: 1.07 (s, 6H), 1.65 (m, 1H), 1.90 (m, 1H), 2.40 (s, 2H), 2.78-2.99 (m, 2H), 3.14 (m, 2H), 3.46 (m, 1H), 3.72-3.90 (m, 4H), 7.46 (s, 3H). MS: [M+H]=317/319/321.

The following Examples were similarly prepared as described above for Example 162:

EXAMPLE 163

1-{[(2,4-Dichlorophenyl)methyl][(3S)-pyrrolidin-3-yl]amino}-2-methylpropan-2-ol L-tartrate

MS: [M+H]=317/319/321.

EXAMPLE 164

1-{{[4-Fluoro-2-(trifluoromethyl)phenyl]methyl}[(3S)-pyrrolidin-3-yl]amino}-2-methylpropan-2-ol D-tartrate

MS: [M+H]=335.

EXAMPLE 165

1-{[(2-Chloro-4-fluorophenyl)methyl][(3S)-pyrrolidin-3-yl]amino}-2-methylpropan-2-ol D-tartrate

MS: [M+H]=301/303.

EXAMPLE 166

1-{[(2-Chloro-6-fluorophenyl)methyl][(3S)-pyrrolidin-3-yl]amino}-2-methylpropan-2-ol L-tartrate a) 1,1-Dimethylethyl (3S)-3-({[2-chloro-6-fluoro-phenyl]methyl}amino)pyrrolidine-1-carboxylate.

To 1,1-dimethylethyl (3S)-3-aminopyrrolidine-1-carboxylate (1.06 g, 5.8 mmol) and 2-chloro-6-fluoro-benzaldehyde (0.95 g, 5.9 mmol) in dichloroethane (10 mL) was added sodium triacetoxyborohydride (3.69 g, 17.4 mmol) in DMF (2 mL). The mixture was left to stir for 3 days at room temperature. To the reaction mixture was added water. After stirring for 10 mins, the chlorinated layer was isolated and purified by flash chromatography on silica, eluting with ethyl acetate/isohexane (20:80 to 40:60), to give the title compound as an oil. MS: [M+H]=329.

b) 1,1-Dimethylethyl (3S)-3-{[(2-chloro-6-fluoro-phenyl)methyl][2-(methoxy)-2-oxoethyl]amino}pyrrolidine-1-carboxylate.

To a solution of 1,1-dimethylethyl (3S)-3-({[2-chloro-6-fluorophenyl]methyl}amino)pyrrolidine-1-carboxylate (0.30 g, 0.81 mmol) in acetonitrile, under nitrogen and at room temperature, was added methyl bromoacetate (0.09 mL, 0.97 mmol), sodium hydrogen carbonate (0.34 g, 4.05 mmole) and potassium iodide (0.07 g, 0.40 mmol). This was left to stir overnight at room temperature. Additional acetonitrile (2 mL) and methyl bromoacetate (0.09 mL, 0.97 mmole) were added, and the reaction mixture heated to 60° C. After 2 h further methyl bromoacetate (0.97 mL, 0.97 mmol) was added. After 2.5 h further methyl bromoacetate (1.84 mL, 1.94 mmol) was added and the temperature increased to 80° C. After 2 hours the reaction mixture was allowed to cool, filtered and purified by flash chromatography on silica, eluting with ethyl acetate/isohexane (0:100 to 30:70), to give the title compound as an oil. MS: [M+H]=443.

c) 1,1-Dimethylethyl (3S)-3-[[(2-chloro-6-fluorophenyl)methyl]((2-hydroxy-2-methypropyl)amino]pyrrolidine-1-carboxylate.

To a solution of 1,1-dimethylethyl (3S)-3-{[(2-chloro-6-fluorophenyl)methyl][2-(methoxy)-2-oxoethyl]amino}-pyrrolidine-1-carboxylate (0.24 g, 0.60 mmol) in dry THF (2 mL), under nitrogen and at −10° C., was added a solution of methyl magnesium bromide in toluene/THF (1.4M solution, 4.28 mL, 5.99 mmol) dropwise over 2 mins. After 3 hours water (50 mL) was added to the reaction mixture followed by ammonium chloride (0.3 g). The resulting mixture was extracted with diethyl ether (3×50 mL). The combined ethereal extracts were washed with brine (50 mL), then dried over sodium sulphate. Concentration in vacuo yielded a pale yellow oil. MS: [M+H]=401.

d) 1-{[(2-Chloro-6-fluorophenyl)methyl][(3S)-pyrrolidin-3-yl]amino}-2-methylpropan-2-ol L-tartrate.

1,1-Dimethylethyl (3S)-3-[[(2-chloro-6-fluorophenyl)-methyl]((2-hydroxy-2-methypropyl)amino]pyrrolidine-1-carboxylate (0.23 mg, 0.57 mmol), trifluoroacetic acid (0.43 mL, 5.74 mmol) and dichloromethane (5 mL) were stirred at room temperature for 3.5 h. The solution was evaporated in vacuo to give an oil. This was redissolved in methanol and filtered through a cationic ion exchange resin (Isolute™ SCX-2). The basic components were isolated by elution with 2N ammonia in methanol. The eluate was evaporated in vacuo and the resultant oil converted to the L-tartrate acid salt (crystallisation from methanol/ethyl acetate/diethyl ether), to give the title compound as a white solid. $^1$H NMR (300 MHz, CD$_3$OD): $\delta_H$ 7.40-7.29 (m, 2H), 7.17-7.11 (t, 1H), 4.44 (s, 2H), 4.04-3.3.93 (m, 3H), 3.53-3.22 (m, 4H), 2.67-2.52 (q, 2H), 2.25-2.17 (m, 2H), 1.01 (s, 3H), 0.94 (s, 3H); MS: [M+H]=301.

The following Examples were similarly prepared as described above for Example 166:

EXAMPLE 167

1-{[(2-Phenyl-5-fluorophenyl)methyl][(3S)-pyrrolidin-3-yl]amino}-2-methylpropan-2-ol L-tartrate $^1$H NMR (300 MHz, CD$_3$OD): $\delta_H$ 7.61-7.58 (d, 1H), 7.50-7.39 (m, 3H), 7.31-7.22 (m, 3H), 7.10-7.05 (t, 1H), 4.44 (s, 2H), 3.90-3.76 (m, 2H), 3.68-3.60 (m, 1H), 3.35-3.30 (m, 1H), 3.20-3.05 (m, 2H), 3.00-2.92 (m, 1H), 2.53-2.43 (m, 2H), 1.90-1.68 (m, 2H), 1.19-1.18 (m, 6H); MS: [M+H]=343.

EXAMPLE 168

1-{{[2-(Trifluoromethyl)phenyl]methyl}[(3S)-pyrrolidin-3-yl]amino}-2-methylpropan-2-ol L-tartrate

MS: [M+H]=317.

EXAMPLE 169

N-(2-Methylpropyl)-N-(4-methylbenzyl)-pyrrolidin-3-amine a) To a suspension of 4-nitrophenyl carbonate resin (1.56 g, 1.5 mmol) in DMF (15 mL) was added 3-trifluoro-acetamidopyrrolidine hydrochloride (0.98 g, 4.5 mmol) and N,N-diisopropylethylamine (1.56 mL, 9 mmol). The mixture was agitated gently for 3 hours, then filtered and washed with DMF (2×5 mL), methanol (3×50 mL) and THF (4×50 mL).

b) To a suspension of the resin prepared in step (a) in THF (27 mL) was added a solution of lithium hydroxide hydrate (315 mg, 7.5 mmol) in water (3 mL). The mixture was agitated gently for 22 hours, then filtered, washed with THF (40 mL), THF/water (1:1 v/v, 40 mL), THF (3×40 mL) and methanol (4×40mL), and dried in vacuo at 40° C.

c) Aliquots (47 mg, 0.05 mmol) of the resin prepared in step (b) were dispensed into a Titan 24-well Filter Plate (Radleys) fitted with 5 μm PTFE frits. The bottom of the filter plate was closed with a PTFE seal retained by a Combi-Clamp (Radleys). To each well was added a 0.5M solution of a substituted benzaldehyde in trimethylorthoformate (1.0 mL, 0.5 mmol), exemplified here by 4-methylbenzaldehyde. The top of the plate was closed with a PTFE seal retained by the Combi-Clamp and the whole assembly agitated by orbital shaking for 66 hrs. After removal of the seals the reactions were filtered under a slight vacuum and washed with TMOF (3×2.5 mL) and DMF (3×2.5 mL).

d) The bottom of the filter plate was closed with a PTFE seal retained by a Combi-Clamp. To each well was added DMF/acetic acid (9:1 v/v, 0.5 mL) and a 1.0M solution of sodium cyanoborohydride in DMF/acetic acid (9:1 v/v, 0.5 mL, 0.5 mmol). The top of the plate was closed with a PTFE seal retained by the Combi-Clamp and the whole assembly agitated by orbital shaking for 23 hrs. After removal of the seals the reactions were filtered under a slight vacuum and washed with DMF (4×2.5 mL).

e) The bottom of the filter plate was closed with a PTFE seal retained by a Combi-Clamp. To each well was added DMF (0.5 mL), a 1.0M solution of an aldehyde in DMF (0.5 mL, 0.5 mmol) (exemplified here by 2-methyl-propanaldehyde) and a 0.5M solution of sodium triacetoxyborohydride in DMF (0.5 mL, 0.25 mmol). The top of the plate was closed with a PTFE seal retained by the Combi-Clamp and the whole assembly agitated by orbital shaking for 23 hours. After removal of the seals the reactions were filtered under a slight vacuum and washed with DMF (2.5 mL), ethanol (2×2.5 mL) and DCM (4×2.5 mL).

f) The bottom of the filter plate was closed with a PTFE seal retained by a Combi-Clamp. To each well was added a TFA/H$_2$O mixture (95:5 v/v, 1 mL). The top of the plate was closed with a PTFE seal retained by the Combi-Clamp and the whole assembly agitated by orbital shaking for 6 hours. After removal of the seals the reactions were filtered under a slight vacuum and washed with DCM (2×2 mL). Appropriate filtrates and washings were combined and volatile components removed by vacuum evaporation. Each residue was dissolved in methanol (1 mL) and the solutions applied to methanol-washed SCX-2 cation-exchange cartridges (0.5 g/2.5 mL) (Jones Chromatography). After draining under gravity the cartridges were washed with methanol (2.5 mL) and the products then eluted using a 2M solution of ammonia in methanol (2.5 mL). Removal of volatile components by vacuum evaporation gave the desired products.

By this means was prepared N-(2-methylpropyl)-N-(4-methylbenzyl)-pyrrolidin-3-amine.

$^1$H NMR δ$_H$ (300 MHz CDCl$_3$): 7.23-7.20 (2H, d), 7.11-7.09 (2H, d), 3.63-3.49 (2H, q), 3.36-3.25 (1H, m), 3.00-2.86 (2H, m), 2.84-2.72 (2H, m), 2.33 (3H, s), 2.22-2.20 (2H, d), 1.84-1.63 (3H, m), 0.88-0.85 (6H, dd); [M+H]=247.

The following Examples were similarly prepared, as described above for Example 169, using the appropriate substituted benzaldehyde in step (c) and the appropriate aldehyde in step (e):

EXAMPLE 170

N-(2-Methylpropyl)-N-(4-chlorobenzyl)-pyrrolidin-3-amine

MS: [M+H]=267/269.

EXAMPLE 171

N-(2-Methylpropyl)-N-(4-methoxybenzyl)-pyrrolidin-3-amine

MS: [M+H]=263

EXAMPLE 172

N-(2-Methylpropyl)-N-(3,4-dichlorobenzyl)-pyrrolidin-3-amine

MS: [M+H]=301/303/305.

EXAMPLE 173

N-(2-Methylpropyl)-N-(2-trifluoromethylbenzyl)-pyrrolidin-3-amine

MS: [M+H]=301

EXAMPLE 174

N-Cyclohexylmethyl-N-benzyl-pyrrolidin-3-amine

MS: [M+H]=273

EXAMPLE 175

N-Cyclohexylmethyl-N-(4-methoxybenzyl)-pyrrolidin-3-amine

MS: [M+H]=303

EXAMPLE 176

N-Cyclohexylmethyl-N-(4-methylbenzyl)-pyrrolidin-3-amine

MS: [M+H]=287

EXAMPLE 177

N-Cyclohexylmethyl-N-(3,4-dichlorobenzyl)-pyrrolidin-3-amine

MS: [M+H]=341/343/345.

EXAMPLE 178

N-Cyclopropylmethyl-N-(4-chlorobenzyl)-pyrrolidin-3-amine

MS: [M+H]=265/267.

EXAMPLE 179

N-Cyclopropylmethyl-N-(4-methoxybenzyl)-pyrrolidin-3-amine

MS: [M+H]=261

EXAMPLE 180

N-Cyclopropylmethyl-N-(3,4-dichlorobenzyl)-pyrrolidin-3-amine

MS: [M+H]=299/301/303.

EXAMPLE 181

N-Cyclopropylmethyl-N-(2-trifluoromethylbenzyl)-pyrrolidin-3-amine

MS: [M+H]=299

EXAMPLE 182

N-Butyl-N-benzyl-pyrrolidin-3-amine

MS: [M+H]=233

EXAMPLE 183

N-Butyl-N-(4-chlorobenzyl)-pyrrolidin-3-amine

MS: [M+H]=267/269.

EXAMPLE 184

N-Butyl-N-(4-methoxybenzyl)-pyrrolidin-3-amine

MS: [M+H]=263

EXAMPLE 185

N-Butyl-N-(4-methylbenzyl)-pyrrolidin-3-amine

MS: [M+H]=247

EXAMPLE 186

N-Butyl-N-(3,4-dichlorobenzyl)-pyrrolidin-3-amine

MS: [M+H]=301/303/305.

EXAMPLE 187

N-Butyl-N-(2-trifluoromethylbenzyl)-pyrrolidin-3-amine

MS: [M+H]=301

EXAMPLE 188

(3S)-N-[(3R)-Tetrahydrofuran-3-yl]-N-{[2-(trifluoromethyl)phenyl]methyl}pyrrolidin-3-amine L-tartrate a) (3S)-Tetrahydrofuran-3-yl 4-methylbenzenesulfonate.

To a stirred solution of (3S)-tetrahydrofuran-3-ol (1.76 g, 20 mmol) dissolved in dry pyridine (20 mL) was added 4-methylbenzenesulfonyl chloride (4.19 g, 22 mmol). The mixture was stirred at room temperature for 4 h, then was diluted with ethyl acetate and washed with aqueous citric acid. The organic extracts were washed with brine, dried (MgSO$_4$), filtered and evaporated in vacuo. The crude product was purified by flash chromatography on silica, eluting with ethyl acetate/cyclohexane (0:100 to 30:70), to yield the title compound as a white solid.

b) 1,1-Dimethylethyl (3S)-3-[(3R)-tetrahydrofuran-3-ylamino]pyrrolidine-1-carboxylate.

A mixture of 1,1-dimethylethyl (3S)-3-amino-pyrrolidine-1-carboxylate (0.95 g, 5.1 mmol), (3S)-tetrahydrofuran-3-yl 4-methylbenzenesulfonate (0.90 g, 3.7 mmol) and anhydrous potassium carbonate (0.53 g, 3.8 mmol) was stirred and heated at 100° C. for 2 days. The reaction mixture was cooled and extracted from water into ethyl acetate. The organic extracts were dried (MgSO$_4$), filtered and evaporated in vacuo. The crude product was purified by flash chromatography on silica, eluting with methanol/ethyl acetate (0:100 to 30:70), to yield the title compound as an oil.

c) 1,1-Dimethylethyl (3S)-3-((3R)-tetrahydrofuran-3-yl{[2-(trifluoromethyl)phenyl]methyl}amino)pyrrolidine-1-carboxylate.

A mixture of 1,1-dimethylethyl (3S)-3-[(3R)-tetrahydrofuran-3-ylamino]pyrrolidine-1-carboxylate (0.20 g, 0.78 mmol), 2-(trifluoromethyl)benzyl bromide (0.22 g, 0.94 mmol) and anhydrous potassium carbonate (0.16 g, 1.17 mmol) in acetonitrile was heated at reflux for 3 days. The reaction was extracted from water into ethyl acetate, and the combined organic extracts dried (MgSO$_4$), filtered and evaporated in vacuo. The crude product was purified by flash chromatography on silica, eluting with ethyl acetate/cyclohexane (20:80 to 40:60), to yield the title compound as an oil.

d) (3S)-N-[(3R)-Tetrahydrofuran-3-yl]-N-{[2-(trifluoromethyl)phenyl]methyl}pyrrolidin-3-amine L-tartrate.

To a stirred solution of 1,1-dimethylethyl (3R)-3-((3R)-tetrahydrofuran-3-yl{[2-(trifluoromethyl)phenyl]-methyl}amino)pyrrolidine-1-carboxylate (0.12 g, 0.29 mmol) in dichloromethane (4 mL) was added trifluoroacetic acid (2 mL). After stirring at room temperature for 3 h the solvent was removed in vacuo and the crude product taken up in methanol. This solution was absorbed onto a cationic ion exchange resin (Isolute™ SCX-2) and the basic components recovered from the column by elution with 2N ammonia in methanol. The eluate was evaporated, taken up again in methanol and L-tartaric acid (1 equivalent) added. The solvent was removed in vacuo and the resultant gum triturated with diethyl ether to yield the title compound as a pink microcrystalline solid. $^1$H NMR (300 MHz, CD$_3$OD) $\delta_H$: 7.82 (d, 1H), 7.57 (d, 1H), 7.53 (t, 1H), 7.32 (t, 1H), 4.31 (s, 2H), 3.92-3.82 (m, 3H), 3.70-3.47 (m, 5H), 3.37-3.22 (m, 2H), 3.17-3.03 (m, 1H), 2.94 (dd, 1H), 2.12-1.96 (m, 2H), 1.85-1.67 (m, 2H); MS: [M+H]=315.

EXAMPLE 189

(3S)-N-[(3S)-Tetrahydrofuran-3-yl]-N-{[2-(trifluoromethyl)phenyl]methyl}pyrrolidin-3-amine L-tartrate Prepared as described above for Example 188, from (3R)-tetrahydrofuran-3-ol. $^1$H NMR (300 MHz, CD$_3$OD) $\delta_H$: 7.81 (d, 1H), 7.57 (d, 1H), 7.53 (t, 1H), 7.32 (t, 1H), 4.30 (s, 2H), 3.95-3.80 (m, 3H), 3.71-3.50 (m, 5H), 3.34-3.22 (m, 2H), 3.17-3.05 (m, 1H), 2.89 (dd, 1H), 2.14-1.95 (m, 2H), 1.89-1.73 (m, 2H); MS: [M+H]=315.

The following Examples were prepared as described above for Examples 188 and 189, from the appropriate enantiomer of tetrahydrofuran-3-ol and the substituted benzyl bromide:

EXAMPLE 190

(3S)-N-([1,1'-Biphenyl]-2-ylmethyl)-N-[(3R)-tetrahydrofuran-3-yl]pyrrolidin-3-amine L-tartrate $^1$H NMR (300 MHz, CD$_3$OD) δ$_H$: 7.63 (d, 1H), 7.49-7.26 (m, 5H), 7.19 (dd, 1H), 4.44 (s, 2H), 3.95-3.85 (m, 1H), 3.70 (bs, 2H), 3.66-3.47 (m, 5H), 3.33-3.05 (m, 3H), 2.87 (dd, 1H), 2.06-1.86 (m, 2H), 1.82-1.62 (m, 2H); MS: [M+H]=323.

EXAMPLE 191

(3S)-N-([1,1'-Biphenyl]-2-ylmethyl)-N-[(3S)-tetrahydrofuran-3-yl]pyrrolidin-3-amine L-tartrate $^1$H NMR (300 MHz, CD$_3$OD) δ$_H$: 7.62 (d, 1H), 7.50-7.23 (m, 5H), 7.19 (dd, 1H), 4.47 (s, 2H), 3.95-3.84 (m, 1H), 3.76 (d, 1H), 3.65 (d, 1H), 3.65-3.44 (m, 5H), 3.37-3.27 (m, 1H), 3.20-3.07 (m, 2H), 2.86-2.76 (m, 1H), 2.03-1.69 (m, 4H); MS: [M+H]=323.

EXAMPLE 192

(3S)-N-[(2-Chloro-6-fluorophenyl)methyl]-N-[(3R)-tetrahydrofuran-3-yl]pyrrolidin-3-amine L-tartrate $^1$H NMR (300 MHz, CD$_3$OD) δ$_H$: 7.28-7.14 (m, 2H), 7.00 (m, 1H), 4.30 (s, 2H), 3.98-3.88 (m, 1H), 3.88-3.78 (m, 3H), 3.68 (m, 1H), 3.56-3.40 (m, 3H), 3.40-3.28 (m, 1H), 3.28-3.05 (m, 3H), 2.08-1.93 (m, 3H), 1.90-1.76 (m, 1H); MS: [M+H]=299/301.

EXAMPLE 193

(3S)-N-[(2-Chloro-6-fluorophenyl)methyl]-N-[(3S)-tetrahydrofuran-3-yl]pyrrolidin-3-amine L-tartrate $^1$H NMR (300 MHz, CD$_3$OD) δ$_H$: 7.39-7.25 (m, 2H), 7.11 (m, 1H), 4.42 (s, 2H), 4.10-3.98 (m, 1H), 3.94 (dd, 2H), 3.91-3.74 (m, 2H), 3.74-3.52 (m, 3H), 3.52-3.41 (m, 1H), 3.33-3.17 (m, 3H), 2.24-2.00 (m, 4H); MS: [M+H]=299/301.

EXAMPLE 194

(3S)-N-[(Tetrahydrofuran-3-yl)methyl]-N-{[2-(trifluoromethyl)phenyl]methyl}pyrrolidin-3-amine L-tartrate a) 1,1-Dimethylethyl (3S)-3-[(tetrahydrofuran-3-yl)methylamino]pyrrolidine-1-carboxylate.

A mixture of 1,1-dimethylethyl (3S)-3-amino-pyrrolidine-1-carboxylate (1.86 g, 10 mmol), tetrahydrofuran-3-carboxaldehyde (2.0 g, 10 mmol) and anhydrous magnesium sulfate (5.0 g) in dichloroethane (15 mL) for 10 mins, then sodium triacetoxyborohydride (4.2 g, 20 mmol) was added in portions over 30 mins. The reaction mixture was left to stir for 3 days. The reaction mixture was diluted with water and extracted into dichloromethane. The organic extracts were washed with water, dried (MgSO$_4$), filtered and evaporated in vacuo. The crude product was purified by flash chromatography on silica, eluting with methanol/chloroform (0:100 to 10:90), to yield the title compound as an oil.

b) 1,1-Dimethylethyl (3S)-3-{[(tetrahydrofuran-3-yl)methyl]{[2-(trifluoromethyl)phenyl]methyl}-amino}pyrrolidine-1-carboxylate.

To a stirred solution of 1,1-dimethylethyl (3S)-3-[(tetrahydrofuran-3-yl)methylamino]pyrrolidine-1-carboxylate (0.54 g, 2 mmol) and 2-(trifluoromethyl)-benzaldehyde (0.52 g, 3 mmol) in dichloroethane (20 mL) was added sodium triacetoxyborohydride (0.85 g, 4 mmol). The reaction mixture was stirred at room temperature for 18 h, then quenched by addition of 2M sodium hydroxide. After stirring for 30mins, the mixture was extracted into ethyl acetate, and the combined organic extracts washed with brine, dried (MgSO$_4$), filtered and evaporated in vacuo. The crude product was purified by flash chromatography on silica, eluting with ethyl acetate/ cyclohexane (10:90 to 30:70), to yield the title compound as an oil.

c) (3S)-N-[(Tetrahydrofuran-3-yl)methyl]-N-{[2-(trifluoromethyl)phenyl]methyl}pyrrolidin-3-amine L-tartrate.

1,1-Dimethylethyl (3S)-3-{[(tetrahydrofuran-3-yl)methyl]{[2-(trifluoromethyl)phenyl]methyl}-amino}pyrrolidine-1-carboxylate was deprotected and purified as described above in Example 188 d). $^1$H NMR (300 MHz, CD$_3$OD) δ$_H$: 7.75 (dd, 1H), 7.58 (d, 1H), 7.53 (t, 1H), 7.33 (t, 1H), 4.30 (s, 2H), 3.81 (bt, 2H), 3.75-3.47 (m, 4H), 3.42 (dd, 1H), 3.35-3.21 (m, 2H), 3.16-3.03 (m, 1H), 3.04-2.92 (m, 1H), 2.55-2.40 (m, 2H), 2.36-2.20 (m, 1H), 2.09-1.80 (m, 1H), 1.90-1.76 (m, 2H), 1.57-1.42 (m, 1H); MS: [M+H]=329.

EXAMPLE 195

(3S)-N-(2-Methylpropyl)-N-{[3-phenylpyrid-2-yl]methyl}-pyrrolidin-3-amine, L-tartrate a) (3-Phenylpyrid-2-yl)methanol.

To 3-phenylpyridine-2-carboxylic methyl ester (2.00 g, 9.38 mmol) in THF, at 0° C. under nitrogen, was added lithium borohydride (0.13 g, 5.85 mmol) in portions over 30 mins. The mixture was allowed to warm to room temperature and left to stir overnight. The mixture was quenched with 2N sodium hydroxide solution (10 mL) and extracted with ethyl acetate (2×50 mL). The combined extracts were dried (Na$_2$SO$_4$) and concentrated in vacuo to give an oil. This was purified by flash chromatography on silica, eluting with ethyl acetate/isohexane (0:100 to 40:60), to give the title compound as an oil. MS: [M+H]=186.

b) 3-Phenylpyridine-2-carbaldehyde.

To oxalyl chloride in dichloromethane (2M solution, 1.59 mL, 2.97 mmol) under nitrogen at −55° C. was added DMSO (0.38 mL, 5.40 mmol) in dichloromethane (0.5 mL), followed by (3-phenylpyrid-2-yl)methanol (0.50 g, 2.70 mmol) in dichloromethane (1.25 mL). After 15 mins, triethylamine (1.88 mL, 13.50 mmol) was added. After a further 15 minutes, the mixture was allowed to warm to room temperature. On reaching room temperature, water (20 mL) was added. This was extracted with dichloromethane (20 mL). The dichloromethane was washed with water (20 mL), brine (20 mL), dried (Na$_2$SO$_4$) and concentrated in vacuo to give the title compound as an oil. MS: [M+H]184.

c) 1,1-Dimethylethyl (3S)-3-({[3-phenylpyrid-2-yl]methyl}amino)pyrrolidine-1-carboxylate.

Sodium triacetoxyborohydride (0.37 g, 1.76 mmol) in DMF (1 mL) was added to a stirred solution 1,1-dimethylethyl (3S)-3-aminopiperidine-1-carboxylate (0.25 g, 1.47 mmol) and 3-phenylpyridine-2-carbaldehyde (0.27 g, 1.47 mmol) in 1,2-dichloroethane (4 mL). After stirring under nitrogen at room temperature for 1 day, the reaction mixture was diluted with methanol (6 mL) and absorbed onto a cationic ion exchange resin (Isolute™ SCX-2). After washing the cartridge with methanol (25 mL), the basic components were isolated by elution with 2N ammonia in methanol and the eluate evaporated to give an oil. This was purified by flash chromatography on silica, eluting with methanol/dichloromethane (0:100 to 30:70), to give the title compound as an oil. MS: [M+H]=354.

d) 1,1-Dimethylethyl (3S)-3-((2-methylpropyl){[3-phenylpyrid-2-yl]methyl}amino)pyrrolidine-1-carboxylate.

Sodium triacetoxyborohydride (0.25 g, 1.19 mmol) in DMF (1 mL) was added to a stirred solution of 1,1-dimethylethyl (3S)-3-({[3-phenylpyrid-2-yl]methyl}amino)-pyrrolidine-1-carboxylate (0.14 g, 0.40 mmol) and isobutyraldehyde (0.11 mL, 1.19 mmol) in 1,2-dichloroethane (4 mL). After stirring under nitrogen at room temperature for 1 day, the reaction mixture was diluted with methanol (6 mL) and absorbed onto a cationic ion exchange resin (Isolute™ SCX-2). After washing the cartridge with methanol (25 mL), the basic components were isolated by elution with 2N ammonia in methanol and the eluate evaporated to give an oil. MS: [M+H]=410.

e) (3S)-N-(2-Methylpropyl)-N-{[3-phenylpyrid-2-yl]methyl}pyrrolidin-3-amine, L-tartrate.

1,1-Dimethylethyl (3S)-3-((2-methylpropyl){[3-phenylpyrid-2-yl]methyl}amino)pyrrolidine-1-carboxylate (0.136 g, 0.335 mmol), trifluoroacetic acid (1 mL) and dichloromethane (4 mL) were stirred at room temperature for 1 day. The solution was evaporated in vacuo to give an oil. This was redissolved in methanol and filtered through a cationic ion exchange resin (Isolute™ SCX-2). The basic components were isolated by elution with 2N ammonia in methanol. The eluate was evaporated in vacuo and the resultant oil converted to the L-tartaric acid salt (triturated with diethyl ether), to give the title compound as a white solid. $^1$H NMR (300 MHz, CD$_3$OD): $\delta_H$ 8.58-8.56 (dd, 1H), 7.71-7.68 (dd, 1H), 7.53-7.38 (m, 6H), 4.43 (s, 2H), 3.87 (s, 2H), 3.56-3.47 (m, 1H), 3.38-3.30 (m, 1H), 3.24-3.12 (m, 2H), 2.99-2.93 (dd, 1H), 2.26-2.14 (m, 2H), 2.02-1.91 (m, 1H), 1.88-1.74 (m, 1H), 1.22-1.09 (m, 1H), 1.22-1.09 (m, 6H); MS: [M+H]=310.

The following Example was similarly prepared, as described above for Example 195:

EXAMPLE 196

(3S)-N-(Cyclohexyl)-N-{[2-(3-phenyl)pyridyl]methyl}-pyrrolidin-3-amine, L-tartrate $^1$H NMR (300 MHz, CD$_3$OD): $\delta_H$ 8.62-8.60 (dd, 1H), 7.73-7.70 (dd, 1H), 7.57-7.38 (m, 6H), 4.43 (s, 2H), 4.01-3.88 (m, 2H), 3.78-3.69 (m, 1H), 3.41-3.33 (m, 1H), 3.28-3.19 (m, 1H), 3.14-3.00 (m, 2H), 2.49-2.41 (m, 1H), 2.04-1.86 (m, 2H), 1.72-1.54 (m, 4H), 1.44-1.40 (m, 1H), 1.15-0.87 (m, 5H); MS: [M+H]=336.

EXAMPLE 197

(3S)-N-(2-Methylpropyl)-N-{[2-(3-pyridyl)-phenyl]methyl}pyrrolidin-3-amine, L-tartrate a) 1,1-Dimethylethyl (3S)-3-(2-methylpropyl amino)-pyrrolidine-1-carboxylate.

1,1-Dimethylethyl (3S)-3-aminopyrrolidine-1-carboxylate (2.00 g, 11.6 mmol), isobutyraldehyde (1.07 mLg, 11.6 mmol), 10% palladium on carbon (0.23 g) and methanol (120 mL) were hydrogenated at 60 psi for 2 h using a Parr hydrogenator. The catalyst was filtered off and the filtrate evaporated in vacuo to give the title compound as an off-white solid. MS: [M+H]=243.

b) 2-(3-Pyridyl)benzaldehyde.

To Pd(PPh$_3$)$_4$ (0.085 g, 0.07 mmol) in acetonitrile (6 mL), under nitrogen, was added water (2 mL) followed by 2-formylphenylboronic acid (0.55 g, 3.68 mmol), 3-bromopyridine (0.36 mL, 3.68 mmol) and potassium carbonate (2.69 g, 22.07 mmol). After stirring for 3 days at 60° C., the reaction mixture was purified by flash chromatography on silica, eluting with ethyl acetate/isohexane (10:90 to 30:70), to give the title compound as an oil. MS: [M+H]=184.

c) 1,1-Dimethylethyl (3S)-3-((2-methylpropyl){[2-(3-pyridyl)phenyl]methyl}amino)pyrrolidine-1-carboxylate.

Sodium triacetoxyborohydride (0.35 g, 1.64 mmol) in DMF (1 mL) was added to a stirred solution of 1,1-dimethylethyl (3S)-3-(2-methylpropylamino)pyrrolidine-1-carboxylate and 2-(3-pyridyl)benzaldehyde (0.265 g, 1.09 mmol) in 1,2-dichloroethane (4 mL). After stirring under nitrogen at room temperature for 1 day, the reaction mixture was purified by flash chromatography on silica, eluting with ethyl acetate/isohexane (0:100 to 40:60), to give the title compound as an oil. MS: [M+H]=410.

d) (3S)-N-(2-Methylpropyl)-N-{[2-(3-pyridyl)-phenyl]methyl}pyrrolidin-3-amine, L-tartrate.

1,1-Dimethylethyl (3S)-3-((2-methylpropyl){2-(pyridyl-methyl)phenyl]methyl}amino)pyrrolidine-1-carboxylate (0.139 mg, 0.335 mmol), trifluoroacetic acid (4 mL) and dichloromethane (10 mL) were stirred at room temperature for 1 day. The solution was evaporated in vacuo to give an oil. This was redissolved in methanol and filtered through a cationic ion exchange resin (Isolute™ SCX-2). The basic components were isolated by elution with 2N ammonia in methanol. The eluate was evaporated in vacuo and the resultant oil converted to the L-tartaric acid salt (crystallisation from ethanol/ether), to give the title compound as a white solid. $^1$H NMR (300 MHz, CD$_3$OD): $\delta_H$ 8.58 (m, 2H), 7.90-7.87 (m, 1H), 7.66-7.55 (m, 2H), 7.49-7.39 (m, 2H), 7.29-7.26 (m, 1H), 4.44 (s, 2H), 3.75-3.58 (m, 2H), 3.55-3.44 (m, 1H), 3.38-3.30 (m, 1H), 3.21-3.10 (m, 2H), 2.89-2.82(dd, 1H), 2.21-2.19 (d, 2H), 1.94-1.69 (m, 2H), 1.54-1.41 (m, 1H), 0.80-0.75 (m, 6H); MS: [M+H]=310.

EXAMPLE 198

(3S)-N-(2-Methylpropyl)-N-{[2-(1-pyrazolyl)phenyl]-methyl}pyrrolidine-3-amine, L-tartrate a) 1,1-Dimethylethyl (3S)-3-((2-methylpropyl){[2-(1-pyrazolyl)phenyl]methyl}amino)pyrrolidine-1-carboxylate.

To copper iodide (1.4 mg, 0.007 mmol), potassium carbonate (0.098 g, 0.802 mmol) and pyrazole (0.099 g, 1.46 mmol), under nitrogen in DMF (1.5 mL), was added (3S)-3-(2-methylpropyl){[(2-bromophenyl)methyl]amino}-pyrrolidine-1-carboxylate (0.300 g, 0.729 mmol). The reaction mixture was sealed in a 10 mL microwave tube and heated in a microwave oven (100 watt power) to 160° C. for 10 minutes, then at 170° C. for 10 minutes, then finally at 200° C. (150 watt power) for 10 minutes. To the reaction mixture was added water (5 mL). This was extracted with dichloromethane (3×2 mL). The combined extracts were purified by flash chromatography on silica, eluting with ethyl acetate/isohexane (0:100 to 40:60), to give the title compound as an oil. MS: [M+H]=399.

b) (3S)-N-(2-Methylpropyl)-N-{[2-(1-pyrazolyl)phenyl]-methyl}pyrrolidine-3-amine, L-tartrate.

1,1-Dimethylethyl (3S)-3-((2-methylpropyl){[2-(1-pyrazolyl)phenyl]methyl}amino)pyrrolidine-1-carboxylate was deprotected as described above in Example 197 d). $^1$H NMR (300 MHz, CD$_3$OD): $\delta_H$ 7.91-7.90 (d, 1H), 7.79-7.75 (m, 2H), 7.57-7.43 (dd, 1H), 6.59-6.57 (m, 1H), 4.43 (s, 2H), 3.69-3.48 (m, 3H), 3.40-3.32 (m, 1H), 3.27-3.12 (m, 2H), 2.96-2.89 (dd, 1H), 2.25-2.23 (d, 2H), 2.02-1.92 (m, 1H), 1.88-1.74 (m, 1H), 1.70-1.57 (m, 1H), 0.90-0.87 (m, 6H); MS: [M+H]=299.

EXAMPLE 199

(3S)-N-Propyl-N-{[2-(trifluoromethyl)phenyl]methyl}-pyrrolidin-3-amine, L-tartrate Method A a) 1,1-Dimethylethyl (3S)-3-((propyl){[2-(trifluoromethyl)phenyl]methyl}amino)pyrrolidine-1-carboxylate.

Sodium triacetoxyborohydride (22.55 g, 106.4 mmol) was added to a stirred solution of 1,1-dimethylethyl (3S)-3-({[2-(trifluoromethyl)phenyl]methyl}amino)pyrrolidine-1-carboxylate (36.66 g, 106.4 mmol), propionaldehyde (7.74 mL, 106.4 mmol) and 1,2-dichloroethane (180 mL). After stirring under nitrogen at room temperature for 1 hour, the reaction mixture was diluted with dichloromethane (10 mL) and washed with 2N sodium hydroxide, then with water. The organic phases were combined and the solvent removed in vacuo. The resultant oil was purified by flash chromatography on silica, eluting with ethyl acetate/cyclohexane (10:90 to 40:60), to give the title compound as an oil. MS: [M+H]=387.

b) (3S)-N-Propyl-N-{[2-(trifluoromethyl)phenyl]methyl}-pyrrolidin-3-amine, L-tartrate.

1,1-Dimethyl (3S)-3-propyl{[2-(trifluoromethyl)-phenyl]methyl}amino)pyrrolidine-1-carboxylate (23.1 g, 59.8 mmol), TFA (45 mL) and DCM (150 mL) were stirred at room temperature for 1 day. The solution was evaporated in vacuo to give an oil. This was redissolved in methanol and filtered through a cationic ion exchange resin (Isolute™ SCX-2). The basic components were isolated by elution with 2N ammonia in methanol. The eluate was evaporated in vacuo and the resultant oil converted to the L-tartaric acid salt to give, after recrystallisation from hot isopropanol, the title compound as a white solid. $^1$H NMR (300 MHz, CD$_3$OD): $\delta_H$ 7.97-7.92(d, 1H), 7.68-7.59 (m, 2H), 7.44-7.42(t, 1H), 4.41 (s, 2H), 3.96-3.82 (AB, 2H), 3.69-3.59 (m, 1H), 3.45-3.3.37 (m, 2H), 3.29-3.2 (m, 1H), 3.15-3.08 (m, 1H), 2.59-2.54 (m, 2H), 2.18-2.09 (m, 1H), 2.03-1.89 (m, 1H), 1.55-1.43 (m, 2H), 0.90-0.85 (t, 3H); MS: [M+H]=287.

Method B a) 1,1-Dimethylethyl (3S)-3-({[2-(trifluoromethyl)phenyl]methyl}amino)pyrrolidine-1-carboxylate.

In a 2L reactor equiped with a 6 blade pitched agitator and a PT100 thermometer was placed 1,1-dimethylethyl (3S)-3-aminopyrrolidine-1-carboxylate (316.6 g, 1.7 mol, 1 equivalent). 2-trifluorobenzaldehyde (301.9 g, 1.73 mol, 1.02 eq. ) was added over 2 h 30 min. The mixture was agitated at 250 rpm. The temperature reached 30° C. and the imine product precipitated partially. Equilibrium moved 98% to the right after 2 h 30 min (followed by $^1$H NMR). The mixture was rotavaporated with 100 ml toluene to remove water. In a 20L double jacketed reactor equipped with overhead stirring (anchor type), the imine preformed above was dissolved in THF (3L -0.05% w/v water). Powdered NaBH(OAc)$_3$ (Callery, 756 g, 3.57 mol, 2.1 eq. ) was added in small fractions over 20 mins. The mixture was agitated after addition for 3 h 40 min. The reaction was quenched with 3L water and 1.2L NaOH 30% (Roland), then 2L toluene was added. The organic phase (yellow, 6.5L) was separated from the aqueous lower phase (transparent, 6L). The organic upper phase was washed with 3L water, dried with brine (2L) then MgSO$_4$ and then filtered before rotavaporation to yield 585 g of crude oil. $^1$H NMR revealed that the product was a 50/50 mixture of imine/amine. Thus, in the same 20L reactor equipped this time with a 3 blade 45° impeller, was placed the imine/amine mixture (580 gr, 1.69 mol, 1 eq. ) dissolved in 0.5L THF (Roland). A suspension of NaBH(OAc)$_3$ (778 gr, 3.67 mol, 2.1 eq. ) in 2.3L of THF (Roland) was added. After 7 h, a further 100 g of NaBH(OAc)$_3$ was added. 1 hr later the reaction was quenched with 3.5L water. Then 1.5L NaOH 30% (Roland) was added to give a pH=14. Then 2L toluene was added. The two phases were separated then the organic upper phase was washed with 6.5L water, dried with 5L brine and filtered to remove Teflon particules from the agitator. The product was azeotropically dried by rotavaporation and traces of toluene were removed from the oil with 0.5L isopropyl alcohol to yield the title compound (487 g) as a slightly yellow oil.

b) 1,1-Dimethylethyl (3S)-3-((propyl){[2-(trifluoromethyl)phenyl]methyl}amino)pyrrolidine-1-carboxylate.

Into a 20L double jacketed reactor equiped with a dropping funnel, a 3 blade 45° impeller, a PT100 thermometer, and a bubbler was placed 1,1-Dimethylethyl (3S)-3-({[2-(trifluoromethyl)phenyl]methyl}amino)pyrrolidine-1-carboxylate (487 g, 1.41 mol, 1 eq.), THF (Roland, 3L), AcOH glacial (Merk p.a., 84.8 g, 1.41 mol, 1 eq.) and NaBH(OAc)$_3$ (Callery, 597 g, 2.82 mol, 2 eq.). Propanal (Acros 99%+, 98.7 g, 1.7 mmol, 1.2 eq) was added over 30 mins at room temperature. The reaction reached 36° C. at the end of the addition. After 4 h, the reaction was complete. The mixture was agitated overnight then quenched with 1L demineralised H$_2$O and neutralised with NaOH (Roland, 30%, 1300 ml) until a pH=14 was achieved. The temperature reached 39° C. After extraction with toluene (Roland, 800 ml) and separation of both phases (organic upper phase (5L) yellow transparent—aqueous lower phase (2.5L) transparent) the organic phase was washed with demineralised H$_2$O (5L) and brine (5L). The product was azeotropically dried by rotavaporation and isopropyl alcohol (400 ml) was used to remove traces of toluene in the oil. 515 g of the title compound as a yellow oil was obtained.

c) (3S)-N-Propyl-N-{[2-(trifluoromethyl)phenyl]methyl}-pyrrolidin-3-amine.

Into a 20 L double jacketed reactor equiped with a 3 blade 45° impeller, a PT100 thermometer, and a refrigerator was place MeOH (Roland, 2.5L), 1,1-Dimethylethyl (3S)-3-((propyl){[2-(trifluoromethyl)phenyl]methyl}amino)pyrrolidine-1-carboxylate (510 g, 1.32 mol, 1 eq.) and HCl 6N (Merck 37% p.a. diluted 2×, 600 ml, 3.6 mol, 3.6 eq.). The mixture was refluxed for 2 h 30 min and observed to turn orange. Another 500 ml HCl 6N was added in small fractions during the reflux then the mixture was allowed to stand at room temperature overnight. Then the mixture was concentrated to 1.5L, neutralised with NaOH (Roland, 30%, 1.1L) and extracted with toluene (Roland, 1L). The two phases were separated and the organic phase was washed twice with demineralised H$_2$O (2×2 L), dried with brine (2L) and rotavaporated. 200 ml isopropyl alcohol was used to remove traces of toluene from the oil. 403 g of the title compound as an orange oil is obtained.

d) (3S)-N-Propyl-N-{[2-(trifluoromethyl)phenyl]methyl}-pyrrolidin-3-amine, L-tartrate.

Into a 10 L double jacketed reactor equiped with a 3 blade 45° impeller, a refrigerator, a bubbler and a PT100 thermometer was placed (3S)-N-Propyl-N-{[2-(trifluoromethyl)phenyl]methyl}-pyrrolidin-3-amine (330 g, 1.15 mol, 1 eq), isopropyl alcohol (Roland, 5L), and L(+)-tartaric acid (176.2 g, 1.15 mol, 1 eq. ). The mixture was heated to dissolution of the tartaric acid then allowed to cool overnight. Precipitation occurred at T>50° C. The mixture was filtered, washed 3× with isopropyl alcohol to a total volume of 2.5L isopropyl alcohol (Roland). The filter cake (volume=1030 cm3, 726 g) was dried at 45° C. under vacuum over night to yield 412 g of the title compound.

The following Examples were similarly prepared as described above for Example 199 (Method A), by reductive alkylation of the appropriate pyrrolidine carboxylate with the appropriate aldehyde and subsequent deprotection:

EXAMPLE 200

(3S)-N-{5-fluoro-2-(trifluoromethyl)phenyl]methyl}-N-propylpyrrolidin-3-amine D-tartrate $^1$H NMR (300 MHz, CD$_3$OD) $\delta_H$: 0.91 (t, 3H), 1.45-1.58 (m, 2H), 1.90-2.03 (m, 1H), 2.13-2.23 (m, 1H), 2.57-2.62 (m, 2H), 3.10-3.17 (m, 1H), 3.22-3.30 (m, 1H), 3.40-3.48 (m, 2H), 3.68 (quintet, 1H), 3.91 (q, 2H), 4.43 (s, 2H), 7.17 (t, d, 1H), 7.70-7.87 (m, 2H); MS: [M+H]=305.

EXAMPLE 201

(3S)-N-(Pyridin-3-ylmethyl)-N-{[2-(trifluoromethyl)-phenyl]methyl}pyrrolidin-3-amine, L-tartrate $^1$H NMR (300 MHz, CD$_3$OD): $\delta_H$ 8.41-8.40 (d, 1H), 8.29-8.27 (d, 1H), 7.76-7.74 (d, 2H), 7.54-7.48 (m, 2H), 7.28-7.24 (m, 2H), 4.30 (s, 2H), 3.79-3.76 (m, 2H), 3.71-3.60 (m, 2H), 3.58-3.52 (m, 1H), 3.36-3.22 (m, 2H), 3.14-3.07 (m, 2H), 2.11-1.92 (m, 2H); MS: [M+H]=336.

EXAMPLE 202

(3S)-N-[(4-Fluoro[1,1'-biphenyl]-2-methyl]-N-(pyridin-2-ylmethyl)pyrrolidin-3-amine, L-tartrate $^1$H NMR (300 MHz, CD$_3$OD): $\delta_H$ 8.35-8.32 (d, 1H), 7.65-7.51 (t, 1H), 7.48-7.00 (m, 9H), 6.91-6.76 (t, 1H), 4.31 (s, 2H), 3.67-3.44 (m, 4H), 3.41-3.20 (m, 1H), 3.18-2.92 (m, 4H), 1.89-1.69 (m, 2H); MS: [M+H]=362.

EXAMPLE 203

(3S)-N-[(4-Fluoro[1,1'-biphenyl]-2-methyl]-N-(pyridin-3-ylmethyl)pyrrolidin-3-amine, L-tartrate $^1$H NMR (300 MHz, CD$_3$OD): $\delta_H$ 8.28-8.26 (m, 2H), 7.59-7.56 (d, 1H), 7.36-7.05 (m, 8H), 6.93-6.87 (t, 1H), 4.32 (s, 2H), 3.62-3.50 (m, 4H), 3.45-3.34 (m, 1H), 3.27-3.01 (m, 3H), 2.98-2.83 (m, 1H), 1.97-1.73 (m, 2H); MS: [M+H]=362.

EXAMPLE 204

(3S)-N-[(2-Chloro-6-fluorophenyl)methyl]-N-(pyridin-2-ylmethyl)pyrrolidine-3-amine, L-Tartrate $^1$H NMR (300 MHz, CD$_3$OD): $\delta_H$ 8.37-8.35 (d, 1H), 7.69-7.63 (t, 1H), 7.39-7.37 (d, 1H), 7.25-7.14 (m, 3H), 7.01-6.97 (t, 1H), 4.43 (s, 2H), 3.98-3.96 (m, 2H), 3.88-3.87 (m, 2H), 3.81-3.70 (m, 1H), 3.49-3.42 (m, 2H), 3.36-3.21 (m, 2H), 2.26-2.09 (m, 2H); MS: [M+H]=320.

EXAMPLE 205

(3S)-N-[(2-Chloro-6-fluorophenyl)methyl]-N-(pyridin-4-ylmethyl)pyrrolidine-3-amine, L-tartrate $^1$H NMR (300 MHz, CD$_3$OD): $\delta_H$ 8.30-8.29 (d, 1H), 8.20-8.18 (d, 1H), 7.61-7.59 (d, 1H), 7.18-7.03 (m, 3H), 6.91-6.84 (m, 1H), 4.33 (s, 2H), 3.82 (s, 2H), 3.76-3.61 (m, 3H), 3.40-3.32 (m, 2H), 3.19-3.11 (m, 2H), 2.16-2.04 (m, 2H); MS: [M+H]=320.

EXAMPLE 206

(3S)-N-[(2-Chloro-6-fluorophenyl)methyl]-N-(pyridin-3-ylmethyl)pyrrolidine-3-amine, L-tartrate $^1$H NMR (300 MHz, CD$_3$OD): $\delta_H$ 8.30-8.29 (d, 1H), 8.20-8.18 (d, 1H), 7.61-7.59 (d, 1H), 7.18-7.03 (m, 3H), 6.91-6.84 (m, 1H), 4.33 (s, 2H), 3.82 (s, 2H), 3.76-3.61 (m, 3H), 3.40-3.32 (m, 2H), 3.19-3.11 (m, 2H), 2.16-2.04 (m, 2H); MS: [M+H]=320.

EXAMPLE 207

(3S)-N-(Pyridin-2-ylmethyl)-N-{[2-(trifluoromethyl)-phenyl]methyl}pyrrolidin-3-amine, L-tartrate

MS: [M+H]=336.

The compounds of the present invention are inhibitors of the uptake of one or more monoamines selected from serotonin, norepinephrine and dopamine. They work by selectively inhibiting one or more of the biogenic amine (serotonin, norepinephrine and dopamine) transporter proteins. Their selectivity profiles may be determined using the assays described below (see also J. Gobel, D. L. Saussy and A. Goetz, J. Pharmacol. Toxicolo. (1999), 42, 237-244). Compounds of formula (I) and their pharmaceutically acceptable salts preferably exhibit a $K_i$ value less than 500 nM at one or more of these monoamine transporter proteins as determined using the scintillation proximity assay as described below. The compounds of formula (I) exemplified above and their pharmaceutically acceptable salts exhibit a $K_i$ value less than 200 nM at one or more of these monoamine transporter proteins as determined using the assays described below. Preferred compounds of formula (I) and their pharmaceutically acceptable salts exhibit a $K_i$ value less than 100 nM at one or more of these monoamine transporter proteins. More preferred compounds of formula (I) and their pharmaceutically acceptable salts exhibit a $K_i$ value less than 50 nM at one or more of these monoamine transporter proteins. Especially preferred compounds of formula (I) and their pharmaceutically acceptable salts exhibit a $K_i$ value less than 20 nM at one or more of these monoamine transporter proteins. Preferably, compounds of the present invention which selectively inhibit one of the three biogenic amine transporters do so relative to the other two transporters by a factor of at least five, more preferably by a factor of at least ten. For example, a NET selective inhibitor has a ratio $K_i(SERT)/K_i(NET)$ and a ratio $K_i(DAT)/K_i(NET)$ greater than or equal to five, preferably greater than or equal to ten. Preferably, compounds of the present invention which selectively inhibit two of the three biogenic amine transporters do so relative to the other transporter by a factor of at least five, more preferably by a factor of at least ten. For example, a NET/SERT selective inhibitor has a ratio $K_i(DAT)/K_i(NET)$ and a ratio $K_i(DAT)/K_i(SERT)$ greater than or equal to five, preferably greater than or equal to ten Biogenic amine transporters control the amount of neurotransmitters in the synaptic cleft. Inhibition of the respective transporter leads to a rise in that neurotransmitter. Inhibition of the individual transporters can be studied by a simple competitive binding assay using selective radioligands for the individual expressed human transporter site. Compounds may be compared for selectivity and potency on the human norepinephrine transporter (hNET), the h-serotonin transporter (hSERT) and the h-dopamine transporter (hDAT) using membranes prepared from HEK293 cells expressing the respective transporter site.

Advantageously, the compounds of the present invention also have a reduced interaction (both as substrate and inhibitor) with the liver enzyme Cytochrome P450 (CYP2D6). That is to say, they preferably exhibit less than 75% metabolism via the CYP2D6 pathway according to the CYP2D6 substrate assay described below and they preferably exhibit an IC50 of >6 µM according to the CYP2D6 inhibitor assay described below.

Generation of Stable Cell-lines Expressing the Human Dopamine, Norepinephrine and Serotonin Transporters Standard molecular cloning techniques were used to generate stable cell-lines expressing the human dopamine, norepinephrine and serotonin transporters. The polymerase chain reaction (PCR) was used in order to isolate and amplify each of the three full-length cDNAs from an appropriate cDNA library. Primers for PCR were designed using the following published sequence data:

Human dopamine transporter: GenBank M95167. Reference: Vandenbergh D J, Persico A M and Uhl G R. *A human dopamine transporter cDNA predicts reduced glycosylation, displays a novel repetitive element and provides racially-dimorphic TaqI RFLPs*. Molecular Brain Research (1992) volume 15, pages 161-166.

Human norepinephrine transporter: GenBank M65105. Reference: Pacholczyk T, Blakely, R D and Amara S G. *Expression cloning of a cocaine-and antidepressant-sensitive human noradrenaline transporter*. Nature (1991) volume 350, pages 350-354.

Human serotonin transporter: GenBank L05568. Reference: Ramamoorthy S, Bauman A L, Moore K R, Han H, Yang-Feng T, Chang A S, Ganapathy V and Blakely R D. *Antidepressant-and cocaine-sensitive human serotonin transporter: Molecular cloning, expression, and chromosomal localization*. Proceedings of the National Academy of Sciences of the USA (1993) volume 90, pages 2542-2546.

The PCR products were cloned into a mammalian expression vector (eg pcDNA3.1 (Invitrogen)) using standard ligation techniques. The constructs were then used to stably transfect HEK293 cells using a commercially available lipofection reagent (Lipofectamine™—Invitrogen) following the manufacture's protocol.

Norepinephrine Binding Assay

The ability of compounds to compete with [³H]-Nisoxetine for its binding sites on cloned human norepinephrine membranes has been used as a measure of its ability to block norepinephrine uptake via its specific transporter.

Membrane Preparation

Cell pastes from large scale production of HEK-293 cells expressing cloned human noradrenaline transporters were homogenised in 4 volumes 50 mM Tris. HCl containing 300 mM NaCl and 5mM KCl, pH 7.4. The homogenate was centrifuged twice (40,000 g, 10 min, 4° C.) with pellet resuspension in 4 volumes Tris. HCl buffer after the first spin and 8 volumes after the second spin. The suspended homogenate was centrifuged (100 g, 10 min, 4° C.) and the supernatant kept and re-centrifuged (40,000 g, 20 min, 4° C.). The pellet was resuspended in Tris. HCl buffer containing the above reagents along with 10% w/v sucrose and 0.1 mM phenylmethylsulfonyl fluoride (PMSF). The membrane preparation was stored in aliquots (1 ml) at −80° C. until required. The protein concentration of the membrane preparation was determined using a bicinchoninic acid (BCA) protein assay reagent kit (available from Pierce).

[³H]-Nisoxetine Binding Assay

Each well of a 96well microtitre plate was set up to contain the following:

| | |
|---|---|
| 50 µl | 2 nM [N-methyl-³H]-Nisoxetine hydrochloride (70-87 Ci/mmol, from NEN Life Science Products) |
| 75 µl | Assay buffer (50 mM Tris•HCl pH 7.4 containing 300 mM NaCl and 5 mM KCl) |
| 25 µl | Test compound, assay buffer (total binding) or 10 µM Desipramine HCl (non-specific binding) |
| 50 µl | Wheatgerm agglutinin coated poly(vinyltoluene) (WGA PVT) SPA Beads (Amersham Biosciences RPNQ0001) (10 mg/ml) |
| 50 µl | Membrane (0.2 mg protein per ml.) |

The microtitre plates were incubated at room temperature for 10 hours prior to reading in a Trilux scintillation counter. The results were analysed using an automatic spline fitting programme (Multicalc, Packard, Milton Keynes, UK) to provide Ki values for each of the test compounds.

Serotonin Binding Assay

The ability of a test compound to compete with [³H]-citalopram from its binding sites on cloned human serotonin membranes has been used as a measure of its ability to block serotonin uptake via its specific transporter (Ramamoorthy, S., Giovanetti, E., Qian, Y., Blakely, R., (1998) J. Biol. Chem. 273,2458).

Membrane Preparation

The preparation of membrane is essentially similar to that for the norepinephrine transporter containing membrane described above. The membrane preparation was stored in aliquots (1 ml) at −70° C. until required. The protein concentration of the membrane preparation was determined using BCA protein assay reagent kit.

[³H]-Citalopram Binding Assay

Each well of a 96well microtitre plate was set up to contain the following:

| | |
|---|---|
| 50 µl | 2 nM [³H]-Citalopram (60-86 Ci/mmol, Amersham Biosciences) |
| 75 µl | Assay buffer (50 mM Tris•HCl pH 7.4 containing 150 mM NaCl and 5 mM KCl) |
| 25 µl | Diluted compound, assay buffer (total binding) or 100 µM Fluoxetine (non-specific binding) |
| 50 µl | WGA PVT SPA Beads (40 mg/ml) |
| 50 µl | Membrane preparation (0.4 mg protein per ml) |

The microtitre plates were incubated at room temperature for 10 hours prior to reading in a Trilux scintillation counter. The results were analysed using an automatic spline fitting programme (Multicalc, Packard, Milton Keynes, UK) to provide Ki (nM) values for each of the test compounds.

Dopamine Binding Assay

The ability to compete with [$^3$H]-WIN35,428 for its binding sites on human cell membranes containing cloned human dopamine transporter has been used as a measure of its ability to block dopamine uptake via its specific transporter (Ramamoorthy et al 1998 supra).

Membrane Preparation.

Is essentially the same as for membranes containing cloned human serotonin transporter as described above.

[$^3$H]-WIN35,428 Binding Assay

Each well of a 96 well microtitre plate was set up to contain the following:

| | |
|---|---|
| 50 µl | 4 nM [$^3$H]-WIN35, 428428 (84-87 Ci/mmol, from NEN Life Science Products) |
| 75 µl | Assay buffer (50 mM Tris•HCl pH 7.4 containing 150 mM NaCl and 5 mM KCl) |
| 25 µl | Diluted compound, assay buffer(total binding) or 100 µM Nomifensine (non-specific binding) |
| 50 µl | WGA PVT SPA Beads (10 mg/ml) |
| 50 µl | Membrane preparation (0.2 mg protein per ml.) |

The microtitre plates were incubated at room temperature for 120 minutes prior to reading in a Trilux scintillation counter. The results were analysed using an automatic spline fitting programme (Multicalc, Packard, Milton Keynes, UK) to provide Ki values for each of the test compounds.

CYP2D6 Assays

Cytochrome P450 2D6 (CYP2D6) is a mammalian enzyme which is commonly associated with the metabolism of around 30% pharmaceutical compounds. Moreover, this enzyme exhibits genetic polymorphism, resulting in the presence of both normal and poor metabolizers in the population. A low involvement of CYP2D6 in the metabolism of compounds (i.e. the compound being a poor substrate of CYP2D6) is desirable in order to reduce any variability from subject to subject in the pharmacokinetics of the compound. Also, compounds with a low inhibitor potential for CYP2D6 are desirable in order to avoid drug-drug interactions with co-administered drugs that are substrates of CYP2D6. Compounds may be tested both as substrates and as inhibitors of this enzyme by means of the following assays.

CYP2D6 Substrate Assay

Principle:

This assay determines the extent of the CYP2D6 enzyme involvement in the total oxidative metabolism of a compound in microsomes. Preferred compounds of the present invention exhibit less than 75% total metabolism via the CYP2D6 pathway.

For this in vitro assay, the extent of oxidative metabolism in human liver microsomes (HLM) is determined after a 30 minute incubation in the absence and presence of Quinidine, a specific chemical inhibitor of CYP2D6. The difference in the extent of metabolism in absence and presence of the inhibitor indicates the involvement of CYP2D6 in the metabolism of the compound.

Materials and Methods:

Human liver microsomes (mixture of 20 different donors, mixed gender) were acquired from Human Biologics (Scottsdale, Ariz., USA). Quinidine and β-NADPH (β-Nicotinamide Adenine Dinucleotide Phosphate, reduced form, tetrasodium salt) were purchased from Sigma (St Louis, Mo., USA). All the other reagents and solvents were of analytical grade. A stock solution of the test compound (TC) was prepared in a mixture of Acetonitrile/Water to reach a final concentration of acetonitrile in the incubation below 0.5%.

The microsomal incubation mixture (total volume 0.1 mL) contained the TC (4 µM), β-NADPH (1 mM), microsomal proteins (0.5 mg/mL), and Quinidine (0 or 2 µM) in 100 mM sodium phosphate buffer pH 7.4. The mixture was incubated for 30 minutes at 37° C. in a shaking waterbath. The reaction was terminated by the addition of acetonitrile (75 µL). The samples were vortexed and the denaturated proteins were removed by centrifugation. The amount of TC in the supernatant was analyzed by liquid chromatography/mass spectrometry (LC/MS) after addition of an internal standard. A sample was also taken at the start of the incubation (t=0), and analysed similarly.

Analysis of the TC was performed by liquid chromatography/mass spectrometry. Ten µL of diluted samples (20 fold dilution in the mobile phase) were injected onto a Spherisorb CN Column, 5 µM and 2.1 mm×100 mm (Waters corp. Milford, Mass., USA). The mobile phase consisting of a mixture of Solvent A/Solvent B, 30/70(v/v) was pumped (Alliance 2795, Waters corp. Milford, Mass., USA) through the column at a flow rate of 0.2 ml/minute. Solvent A and Solvent B were a mixture of ammonium formate $5.10^{-3}$ M pH 4.5/methanol in the proportions 95/5 (v/v) and 10/90 (v/v), for solvent A and solvent B, respectively. The TC and the internal standard were quantified by monitoring their molecular ion using a mass spectrometer ZMD or ZQ (Waters-Micromass corp, Manchester, UK) operated in a positive electrospray ionisation.

The extent of CYP2D6 involvement (% of CYP2D6 involvement) was calculated comparing the extent of metabolism in absence and in presence of quinidine in the incubation.

The extent of metabolism without inhibitor (%) was calculated as follows:

$$\frac{(TC \text{ response in samples without inhibitor})_{time\,0} - (TC \text{ response in samples without inhibitor})_{time\,30}}{(TC \text{ response in samples without inhibitor})_{time\,0}} \times 100$$

The extent of metabolism with inhibitor (%) was calculated as follows:

$$\frac{(TC \text{ response in samples without inhibitor})_{time\,0} - (TC \text{ response in samples with inhibitor})_{time\,30}}{(TC \text{ response in samples without inhibitor})_{time\,0}} \times 100$$

where the TC response is the area of the TC divided by the area of the internal standard in the LC/MS analysis chromatogram, time0 and time30 correspond to the 0 and 30 minutes incubation time.

The % of CYP2D6 involvement was calculated as follows:

$$\frac{(\% \text{ extent of metabolism without inhibitor}) - (\% \text{ extent of metabolism with inhibitor})}{\% \text{ extent of metabolism without inhibitor}} \times 100$$

CYP2D6 Inhibitor Assay

Principle:

The CYP2D6 inhibitor assay evaluates the potential for a compound to inhibit CYP2D6. This is performed by the measurement of the inhibition of the bufuralol 1'-hydroxylase activity by the compound compared to a control. The 1'-hydroxylation of bufuralol is a metabolic reaction specific to CYP2D6. Preferred compounds of the present invention exhibit an IC$_{50}$ higher than 6 µM for CYP2D6 activity, the IC$_{50}$ being the concentration of the compound that gives 50% of inhibition of the CYP2D6 activity.

Material and Methods:

Human liver microsomes (mixture of 20 different donors, mixed gender) were acquired from Human Biologics (Scottsdale, Ariz.). β-NADPH was purchased from Sigma (St Louis, Mo.). Bufuralol was purchased from Ultrafine (Manchester, UK). All the other reagents and solvents were of analytical grade.

Microsomal incubation mixture (total volume 0.1 mL) contained bufuralol 10 µM, β-NADPH (2 mM), microsomal proteins (0.5 mg/mL), and the test compound (TC) (0, 5, and 25 µM) in 100 mM sodium phosphate buffer pH 7.4. The mixture was incubated in a shaking waterbath at 37° C. for 5 minutes. The reaction was terminated by the addition of methanol (75 µL). The samples were vortexed and the denaturated proteins were removed by centrifugation. The supernatant was analyzed by liquid chromatography connected to a fluorescence detector. The formation of the 1'-hydroxybufuralol was monitored in control samples (0 µM TC) and in the samples incubated in presence of the TC. The stock solution of TC was prepared in a mixture of Acetonitrile/Water to reach a final concentration of acetonitrile in the incubation below 1.0%.

The determination of 1'Hydroxybufuralol in the samples was performed by liquid chromatograhy with fluorimetric detection as described below. Twenty five µL samples were injected onto a Chromolith Performance RP-18e column (100 mm×4.6 mm) (Merck KGAa, Darmstadt, Germany). The mobile phase, consisting of a mixture of solvent A and solvent B whose the proportions changed according the following linear gradient, was pumped through the column at a flow rate of 1 ml/min:

| Time (minutes) | Solvent A (%) | Solvent B (%) |
|---|---|---|
| 0 | 65 | 35 |
| 2.0 | 65 | 35 |
| 2.5 | 0 | 100 |
| 5.5 | 0 | 100 |
| 6.0 | 65 | 35 |

Solvent A and Solvent B consisted of a mixture of 0.02 M potassium dihydrogenophosphate buffer pH3/methanol in the proportion 90/10 (v/v) for solvent A and 10/90 (v/v) for solvent B. The run time was 7.5 minutes. Formation of 1'-hydroxybufuralol was monitored by fluorimetric detection with extinction at λ252 nm and emission at λ302 nm.

The IC$_{50}$ of the TC for CYP2D6 was calculated by the measurement of the percent of inhibition of the formation of the 1'-hydroxybufuralol in presence of the TC compared to control samples (no TC) at a known concentration of the TC.

The percent of inhibition of the formation of the 1'-hydroxybufuralol is calculated as follows:

$$\frac{(1' - \text{hydroxybufuralol formed without inhibitor}) - (1' - \text{hydroxybufuralol formed with inhibitor})}{(1' - \text{hydroxybufuralol area formed without inhibitor})} \times 100$$

The IC$_{50}$ is calculated from the percent inhibition of the formation of the 1'-hydroxybufuralol as follows (assuming competitive inhibition):

$$\frac{TC \text{ Concentration} \times (100 - \text{Percent of inhibition})}{\text{Percent of inhibition}}$$

The IC$_{50}$ estimation is assumed valid if inhibition is between 20% and 80% (Moody G C, Griffin S J, Mather A N, McGinnity D F, Riley R J. 1999. Fully automated analysis of activities catalyzed by the major human liver cytochrome P450 (CYP) enzymes: assessment of human CYP inhibition potential. Xenobiotica, 29(1): 53-75).

The invention claimed is:

1. A compound of formula (I):

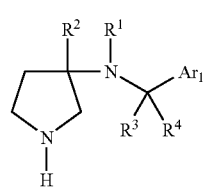

wherein
R$^1$ is n-propyl, 1-methylethyl, 2-methylpropyl, or 3,3-dimethylpropyl;
R$^2$, R$^3$ and R$^4$ are each independently selected from hydrogen or C$_1$-C$_2$ alkyl; and
Ar$_1$ is a phenyl group which is optionally substituted with 1, 2 or 3 substituents each independently selected from halo, trifluoromethyl and C$_1$-C$_4$ alkyl and/or with 1 substituent selected from phenyl, phenyl substituted with 1, 2 or 3 halo substituents, pyridinyl, pyrazolyl, phenoxy and phenoxy substituted with 1, 2 or 3 halo substituents; pyridinyl; or pyridinyl substituted with 1, 2 or 3 substituents each independently selected from halo, trifluoromethyl and C$_1$-C$_4$ alkyl and/or with 1 substituent selected from phenyl and phenyl substituted with 1, 2 or 3 halo substituents;
or a pharmaceutically acceptable salt thereof.

2. The compound of claim 1, wherein R$^2$, R$^3$, and R$^4$ are each hydrogen.

3. The compound of claim 1, wherein —Ar$_1$ is phenyl or phenyl substituted with 1, 2 or 3 substituents each independently selected from halo, trifluoromethyl and C$_1$-C$_4$ alkyl and/or with 1 substituent selected from phenyl, phenyl substituted with 1, 2 or 3 halo substituents, pyridinyl, pyrazolyl, phenoxy and phenoxy substituted with 1, 2 or 3 halo substituents.

4. A pharmaceutical composition, comprising a compound of claim 1 or a pharmaceutically acceptable salt thereof, or 3-[(phenylmethyl)-(3S)-3-pyrrolidinylamino]-propanenitrile or a pharmaceutically acceptable salt thereof, together with a pharmaceutically acceptable diluent or carrier.

5. A method for treating attention-deficit hyperactivity disorder (ADHD), comprising administering to a patient in need thereof an effective amount of a compound of claim 1 which selectively inhibits the reuptake of norepinephrine over serotonin and dopamine, or a pharmaceutically acceptable salt thereof.

* * * * *